US009045414B2

(12) United States Patent
Burdack et al.

(10) Patent No.: US 9,045,414 B2
(45) Date of Patent: Jun. 2, 2015

(54) PYRROLIDIN-2-ONES

(75) Inventors: Christoph Burdack, Munich (DE); Cedric Kalinski, Munich (DE); Vladimir Khazak, Princeton, NJ (US); Gunther Ross, Munich (DE); Lutz Weber, Germering (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 13/351,914

(22) Filed: Jan. 17, 2012

(65) Prior Publication Data

US 2012/0122839 A1 May 17, 2012

Related U.S. Application Data

(62) Division of application No. 12/560,051, filed on Sep. 15, 2009, now Pat. No. 8,119,623.

(60) Provisional application No. 61/096,964, filed on Sep. 15, 2008.

(30) Foreign Application Priority Data

Sep. 15, 2008 (EP) .................................... 08016236

(51) Int. Cl.

| | |
|---|---|
| ***C07D 401/14*** | (2006.01) |
| ***C07D 403/04*** | (2006.01) |
| ***C07D 403/14*** | (2006.01) |
| ***C07D 409/14*** | (2006.01) |
| ***C07D 487/10*** | (2006.01) |
| ***A61K 31/404*** | (2006.01) |
| ***A61K 31/4439*** | (2006.01) |
| ***A61K 31/454*** | (2006.01) |
| ***A61K 31/496*** | (2006.01) |
| ***A61K 31/5377*** | (2006.01) |
| ***A61K 31/551*** | (2006.01) |
| ***C07D 207/277*** | (2006.01) |
| ***C07D 401/06*** | (2006.01) |
| ***C07D 401/12*** | (2006.01) |
| ***C07D 409/12*** | (2006.01) |

(52) U.S. Cl.

CPC .......... *C07D 207/277* (2013.01); *C07D 487/10* (2013.01); *C07D 401/06* (2013.01); *C07D 401/12* (2013.01); *C07D 401/14* (2013.01); *C07D 403/04* (2013.01); *C07D 403/14* (2013.01); *C07D 409/12* (2013.01); *C07D 409/14* (2013.01)

(58) Field of Classification Search

None

See application file for complete search history.

(56) References Cited

U.S. PATENT DOCUMENTS

| | | | | |
|---|---|---|---|---|
| 3,361,759 | A | 1/1968 | Anthony et al. | |
| 4,219,560 | A | 8/1980 | Houlihan | |
| 5,574,044 | A * | 11/1996 | Thompson et al. | 514/316 |
| 2009/0029963 | A1 * | 1/2009 | Aebi et al. | 514/210.2 |

FOREIGN PATENT DOCUMENTS

| | | | |
|---|---|---|---|
| EP | 1 180 513 | A | 2/2002 |
| WO | WO 2008/005268 | A | 1/2008 |

OTHER PUBLICATIONS

Burdzhiev et al. Z. Naturforsch. 2008, 63b, 313-320.*
Suto et al. J. Heterocyclic Chem., 29, 1441 (1992).*
"Guidance for Industry: Q3C—Tables and List," U.S. DHHS/FDA/CDER/CBER, Nov. 2003, Revision 1.*
"Guidance for Industry: Q3C—Tables and List." US DHHS, FDA, CDER, CBER, Nov. 2003. Revision 1.*
Zhang et al., Chem. Commun., 2008, pp. 4837-4839.*
Peterson et al., Angew. Chem. Int. Ed., 2009, 48, pp. 6328-6331.*
Burchak et al. Russian Chemical Bulletin, International Edition, vol. 51, No. 7, pp. 1308-1318, Jul. 2002.*

(Continued)

*Primary Examiner* — Alicia L Otton
(74) *Attorney, Agent, or Firm* — Frommer Lawrence & Haug LLP; Ronald R. Santucci

(57) ABSTRACT

The present invention provides compounds of formula (I) or (Ia) which are ligands binding to the HDM2 protein, inducing apoptosis and inhibiting proliferation, and having therapeutic utility in cancer therapy and prevention.

(I)

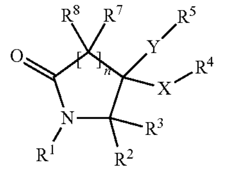

(Ia)

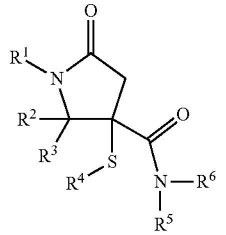

Compounds of formula (I) or (Ia) can be used as therapeutics for treating stroke, myocardial infarction, ischemia, multi-organ failure, spinal cord injury, Alzheimer's Disease, injury from ischemic events and heart valvular degenerative disease. Moreover, compounds of formula (I) or (Ia) can be used to decrease the side effects from cytotoxic cancer agents, radiation and to treat viral infections.

13 Claims, No Drawings

(56) References Cited

OTHER PUBLICATIONS

Sell et al., J. Org. Chem., 1995, 60, p. 1077-1080.*
International Search Report issued by the European Patent Office for corresponding international application PCT/EP2009/006670, mailed Nov. 13, 2009.
Written Opinion of the International Searching Authoity issued by the European Patent Office for corresponding international application PCT/EP2009/006670, mailed Nov. 13, 2009.
Imamura, Shinichi et al., "CCR5 Antagonists as Anti-HIV-1 Agents. 1. Synthesis and Biological Evaluation of 5-Oxopyrrolidine-3-carboxamide Derivative", *Chem. Pharm. Bull.*, 52(1), 2004, pp. 63-73.
Wei, Jingqiang et al.: "Diastereoselective Synthesis of γ-Lactams by a One-Pot, Four-Component Reaction", *Organic Letters,* 2007, vol. 9, No. 20, pp. 4077-4080.
Ng, Pul Yee et al.: "Cycloaddition Reactions of Imines with 3-Thiosuccinic Anhydrides: Synthesis of the Tricylic Core of Martinellic Acid", *Organic Letters*, 2006, vol. 8, No. 18, pp. 3999-4002.
Ng, Pui Yee et al.: "Synthesis of Diverse Lactam Carboxamides Leading to the Discovery of a New Transcription-Factor Inhibitor", *Angew. Chem. Int. Ed.*, 2007, 46, pp. 5352-5355.
Henning, Wilhelm et al.: "MDM2 Is a Target of Simian Virus 40 in Cellular Transformation and during Lytic Infection", *Journal of Virology*, vol. 71, No. 10, Oct. 1997, pp. 7609-7618.
Galatin, Peter S. et al.: "A Nonpeptidic Sulfonamide Inhibits the p53-mdm2 Interaction and Activates p53-Dependent Transcription in mdm-2-Overexpressing Cells", *J.Med.Chem.*, 47, 2004, pp. 4163-4165.
Danovi, Davide et al.: "Amplification of Mdmx (or Mdm4) Directly Contributes to Tumor Formation by Inhibiting p53 Tumor Suppressor Activity", *Molecular and Cellular Biology*, vol. 24, No. 13, Jul. 2004, pp. 5835-5843.
Bres, Vanessa et al.: "A non-proteolytic role for ubiquitin in Tat-mediated transactivation of the HIV-1 promoter", *Nature Cell Biology*, vol. 5, No. 8, Aug. 2003, pp. 754-761 plus supplemental pp. 24-25 and supplemental figure sheets S1-S4.
Vousden, Karen H. et al.: "Live or Let Die: The Cell's Response to p53", *Nature Reviews*, vol. 2, Aug. 2002, pp. 594-604.
Zhao, Jianhua et al.: "The initial evaluation of non-peptidic small-molecule HDM2 inhibitors based on p53-HDM2 complex structure", *Cancer Letters*, 183, 2002, pp. 69-77.
Vassilev, Lyubomir T. et al.: "In Vivo Activation of the p53 Pathway by Small-Molecule Antagonists of MDM2", *Sciencexpress*, Jan. 2, 2004, 8 pages.
Momand, Jamil et al.: "The MDM2 gene amplification database", *Nucleic Acids Research*, vol. 26, No. 15, 1998, pp. 3453-3459.
Popowicz, Grzegorz M. et al.: Molecular Basis for the Inhibition of p53 by Mdmx, *Cell Cycle*, vol. 6, Issue 19, pp. 2386-2392, Oct. 1, 2007.
Larusch, Gretchen A. et al.: "Nutlin3 Blocks Vascular Endothelial Growth Factor Induction by Preventing the Interaction between Hypoxia Inducible Factor 1α and Hdm2", *Cancer Res 2007*, 67, 2, Jan. 15, 2007, pp. 450-454.
Grasberger, Bruce L. et al.: "Discovery and Cocrystal Structure of Benzodiazepinedione HDM2 Antagonist That Activate p53 in Cells", *J. Med. Chem.*, 48, 2005, pp. 909-912.
Juven-Gershon, Tamar et al.: "The Mdm2 Oncoprotein Interacts with the Cell Fate Regulator Numb", *Molecular and Cellular Biology*, vol. 18, No. 7, Jul. 1998, pp. 3974-3982.
Yang, Hai Liang et al.: "Adenovirus-mediated E2F-1 Gene Transfer Inhibits MDM2 Expression and Efficiently Induces Apoptosis in MDM2-overexpressing Tumor Cells", *Clinical Cancer Research*, vol. 5, Aug. 1999, pp. 2242-2250.
Zhang, Zhuo et al.: "MDM2 Is a Negative Regulator of p21 $^{WAF1/CIP1}$, Independent of p53", *The Journal of Biological Chemistry*, vol. 279, No. 16, Apr. 16, 2004, pp. 16000-16006.
Moule, Madeleine G. et al.: "Role for PP2A in ARF signaling to p53", *PNAS*, vol. 101, No. 39, pp. 14063-14066, Sep. 28, 2004.
Efeyan, Alejo et al.: "Induction of p53-Dependent Senescence by the MDM2 Antagonist Nutlin-3a in Mouse Cells of Fibroblast Origin", *Cancer Res 2007*, 67, (15), Aug. 1, 2007, pp. 7350-7357.
Zhang, Zhuo et al.: "Antisense therapy targeting MDM2 oncogene in prostate cancer: Effects on proliferation, apoptosis, multiple gene expression, and chemotherapy", *PNAS*, vol. 100, No. 20, Sep. 30, 2003, pp. 11636-11641.
O'Shea, Clodagh C. et al.: "Modulation of the ARF-p53 Pathway by the Small DNA Tumor Viruses", *Cell Cycle*, 4:3, Mar. 2005, pp. 449-452.
Machida, Keigo et al.: "Hepatitis C virus induces a mutator phenotype: Enhanced mutations of immunoglobulin and prooncogenes", *PNAS*, vol. 101, No. 12, Mar. 23, 2004, pp. 4262-4267.
Wei, Jingquing, "Diastereoselective Synthesis of y-Lactams by a One-Pot, Four-Component Reaction", *Organic Letters*, 9(20) 2007,pp. 4077-4080.
Wang, Xiang, "Small-Molecule Reagants for Cellular Pull-Down Experiments", *Bioconjugate Chem*, 2008 19(3), pp. 585-587.
Golub et al. Science (1999), vol. 286 531-537.
Lala et al. Cancer and Metastasis Reviews (1998), 17(1), 91-106.
Morissette et al. Advanced Drug Delivery Reviews 2004, 56, 275-300.
Vippagunta et al., abstract, Vippagunta, Sudha R. "Crystalline Solids" Advanced Drug Delivery Reviews 48(2001); 3-26.
Ng, Pui Yee, Cycloaddition Reactions of Imines with 3-Thiosuccinic Anhydrides:Synthesis of the Tricyclic Core of Marinellic Acid. Organic Letters 8(18) (2006) pp. 3999-4002.

* cited by examiner

PYRROLIDIN-2-ONES

This application claims priority benefits of U.S. Provisional Patent Application No. 61/096,964 filed Sep. 15, 2008 and European Patent Application No. EP 08 016 236.5 filed Sep. 15, 2008, the disclosures of both are hereby incorporated by reference.

BACKGROUND OF THE INVENTION

MDM2 (also known as HDM2) plays a central role in regulating and influencing important cell-signalling pathways. HDM2 is known to interact with a range of different proteins that control cell cycle progression, cellular apoptosis, proliferation and survival.

Thus, amongst other proteins, HDM2 binds to the tumor suppressor protein p53 and targets this protein for ubiquitination and degradation; facilitate translocation of p53 from the nucleus to cytosole and further translocation to the proteosomes. Thereby, HDM2 prevents transactivation of p53 target genes that are implicated in the regulation of cell cycle and apoptosis. The p53 protein is a potent cell cycle inhibitor that prevents propagation of permanently damaged cell clones by the induction of growth arrest or apoptosis, resulting in the protection against development of cancer by guarding cellular and genomic integrity.

Both p53 as well as HDM2 can be associated with cancer: about 50% of all human tumors harbor a mutation or deletion in the p53 gene that impairs normal p53 function. In many cancers with wild-type p53, HDM2 is overexpressed, disabling the normal p53 function (Momand et al. *Nucleic Acids Res.* 1998, 26, 3453-3459).

The HDM2 gene has a p53-responsive promoter element and elevated levels of p53 that translocate to the nucleus induce expression of HDM2. Induction of HDM2 by p53 forms an autoregulatory feedback loop, ensuring low levels of both HDM2 and p53 in normally proliferating cells (Vousden and Lu *Nature Reviews Cancer* 2002, 2, 594-604). However, in many cancers this normal ratio of HDM2 to p53 is changed and misregulated.

Inhibiting the interaction of HDM2 with p53 in cells with wild-type p53 should lead to an increase of p53 levels in the nucleus, facilitating cell cycle arrest and/or apoptosis and restoring the tumor suppressor role of p53. The feasibility of this strategy has been shown by the use of different macromolecular tools for inhibition of HDM2-p53 interaction (e.g. antibodies, antisense oligonucleotides, peptides).

Besides p53, a number of proteins have been found to interact with HDM2, performing either affectors (regulating HDM2 functions) or effectors (regulated by HDM2). Totally about 20 interacting with HDM2 proteins have been described (Ganguli and Wasylyk, *Mol. Cancer. Research,* 2003, v.1, 1027-1035), Zhu et al. *Mol. Cell,* 2009, 35, 316-326). Among them, HDM2 binds to the tumor suppressor pRB, as well as E2F-1 (Yang et al. *Clinical Cancer Research* 1999, 5, 2242-2250).

E2F-1 is a transcription factor that regulates S phase entry and has been shown to cause apoptosis in some cell types when overexpressed. HDM2 binds to E2F through a conserved binding region at p53, activating E2F-dependent transcription of cyclin A, and suggesting that HDM2 small molecule ligands or antagonists might have also anti-tumor effects in cells independent of their role of restoring p53 function.

HDM2 can associate in vitro and in vivo with the mammalian Numb protein. The association occurs through the N-terminal domain of HDM2, which is the region also involved in p53 binding. The Numb protein is involved in the regulation of cell fate and in a variety of developmental processes, most notably in the nervous system. Through its interaction with Numb, HDM2 may influence processes such as differentiation and survival. This could also contribute to the altered properties of tumor cells, which overexpress HDM2 (Juven-Gershon et al. *Mol. Cell. Biol.* 1998, 18, 3974-3982).

Similarly, small molecules that block the HDM2 interaction with p53 also block the interaction of HDM2 with hypoxia inducible factor 1α (HIF-1α), a protein that induces vascular endothelial growth factor (VEGF) under normoxic or hypoxic conditions. As VEGF is proangiogenic, inhibition of HDM2 by small molecules will also prevent blood vessel formation to cancer metastases and primary tumors (G. A. LaRusch et al. *Cancer Res.* 2007, 67, 450-454).

There is also evidence that HDM2 has a direct role in the regulation of p21, a cyclin-dependent kinase inhibitor. The inhibition of HDM2 with anti-HDM2 antisense oligonucleotide or Short Interference RNA targeting HDM2 significantly elevates p21 protein levels in p53 null PC3 cells. In contrast, overexpression of HDM2 diminishes p21 levels by shortening the p21 half-life, an effect reversed by HDM2 antisense inhibition. HDM2 facilitates p21 degradation independent of ubiquitination and the E3 ligase function of HDM2. Instead, HDM2 promotes p21 degradation by facilitating binding of p21 with the proteasomal C8 subunit. The p21 and HDM2 bind through 180—the 298 amino acids region of the HDM2 protein (Zhang et al. *J. Biol. Chem.* 2004, 279, 16000-16006).

There is also evidence for a malfunctioning HDM2 regulation having effect on a proper p53 function and causing cancer, beyond mutated p53 or overexpression of HDM2. Thus, when E2F signals the growth of a cancer, P14ARF is dispatched to break down HDM2, freeing p53 to kill the cancer cell. In certain cancers P14ARF is lacking (Moule et al. *Proc. Natl. Acad. Sci. U.S.A.* 2004, 101, 14063-6). P14ARF binds to HDM2 and promotes the rapid degradation of HDM2. ARF-mediated HDM2 degradation is associated with HDM2 modification and concurrent p53 stabilization and accumulation.

Small molecule HDM2 inhibitors also induce senescence dependent on the presence of functional p53, whereas cells lacking p53 were completely insensitive (A. Efeyan, A. Ortega-Molina, S. Velasco-Miguel, D. Herranz, L. T. Vassilev, M. Serrano, *Cancer Res.* 2007, 67, 7350-7357).

The validity of inhibiting HDM2 as a therapeutic concept has been first demonstrated by antisense HDM2 inhibitors that exhibit significant antitumor activity in multiple human cancer models with various p53 statuses (Zhang et al. *Proc. Natl. Acad. Sci, USA.* 2003, 100, 11636-11641).

Small molecule antagonists of the HDM2 protein interactions may therefore offer a viable approach towards cancer therapy, either as single agents or in combination with a broad variety of other anti-tumour therapies.

There is also growing evidence that HDM2 plays an important role in viral infections. First, it is known that viruses rely on changing normal p53 signalling (O'shea and Fried M. *Cell Cycle* 2005; Machida et al. *Proc. Natl. Acad. Sci. U.S.A.* 2004, 23, 101, 4262-7).

Second, HDM2 directly interacts with viral proteins, for example HDM2 is a target of simian virus 40 in cellular transformation and during lytic infection (Henning et al. *J. Virol,* 1997, 71, 7609-7618). Furthermore, the HDM2 protein, like p53, becomes metabolically stabilized in SV40-transformed cells. This suggests the possibility that the specific targeting of HDM2 by SV40 is aimed at preventing HDM2-directed proteasomal degradation of p53 in SV40- infected and -transformed cells, thereby leading to metabolic stabilization of p53 in these cells. A trimeric LT-p53-HDM2 complex is formed with simian virus 40 large tumour antigen (LT) in SV40-transformed cells.

The human immunodeficiency virus type 1 (HIV-1) encodes a potent transactivator, Tat. HDM2 has been shown to interact with Tat and mediating its ubiquitination in vitro and in vivo. In addition, HDM2 is a positive regulator of Tat-mediated transactivation, indicating that the transcriptional properties of Tat are stimulated by ubiquitination (Bres et al. *Nat Cell Biol.* 2003, 5, 754-61).

Small molecule inhibitors of the HDM2 interaction have been reported and show pro-apoptotic effects in in vitro models and an antitumor effect in animal models of cancer. Thus, benzodiazepines have been used as a chemical scaffold to achieve HDM2 inhibitory activity (Grasberger et al. *J. Med. Chem.* 2005, 48, 909-912; Parks et al. *Bioorganic & Medicinal Chemistry Letters* 2005, 15, 765-770). Similarly, imidazolines (Vassilev et al. *Science* 2004, 303, 844-848), isoindolones (Hardeastle et al. *Bioorganic & Medicinal Chemistry Letters* 2005, 15, 1515-1520), norbornanes (Zhao et al. *Cancer Letters* 2002, 183, 69-77) and sulfonamides (Galatin and Abraham *J. Med. Chem.* 2004, 47, 4163-4165) have been reported as small molecule HDM2 inhibitors.

It has also been reported that HDM2 ligands have a cytoprotective effect. Thus, HDM2 inhibitors can be employed in methods of inducing cytoprotection and are useful to protect non-target cells against the harmful effects of chemotherapeutic agents. The amount of HDM2 inhibitor that provides such an effect can be about 5 to about 10 fold lower than the amount needed to induce apoptosis (Koblish et al. WO03095625, METHOD FOR CYTOPROTECTION THROUGH HDM2 AND HDM2 INHIBITION, 2003 Nov. 20).

Pyrrolidin-2-ones have already been described as therapeutically useful compounds to treat viral infections (U.S. Pat. No. 6,509,359, PYRROLIDIN-2-ONE COMPOUNDS AND THEIR USE AS NEURAMINIDASE INHIBITORS, 1999 Mar. 25), to inhibit factor Xa for the treatment of cardiovascular disorders (U.S. Pat. No. 7,226,929, Pyrrolidin-2-one derivatives as inhibitors of factor Xa, 2006 Mar. 17; Watson et al., Design and Synthesis of Orally Active Pyrrolidin-2-one-Based Factor Xa Inhibitors, Bioorganic & Medicinal Chemistry Letters 2006, 16, 3784-3788), as inhibitors of 11βHSD1 for the treatment of diabetes (WO/2005/108360, PYRROLIDIN-2-ONE AND PIPERIDIN-2-ONE DERIVATIVES AS 11-BETA HYDROXYSTEROID DEHYDROGENASE INHIBITORS, 2005 Apr. 29). Pyrrolidin-2-ones are scaffolds for established therapeutic compounds such as rolipram, an antidepressant agent and oxiracetam, piracetam or nebracetam, being nootropic drugs for the Alzheimer's disease. These compounds have low toxicity, good pharmaco-kinetic properties and render the chemical class of pyrrolidin-2-ones an interesting scaffold for new drug candidates.

MDMX (also known as MDM4 or HDMX) is a relative of MDM2 that was identified on the basis of its ability to physically interact with p53. An increasing body of evidence, including recent genetic studies, suggests that MDMX also acts as a key negative, independent regulator of p53. Aberrant expression of MDMX may contribute to tumor formation and is observed for example in gliomas, breast cancers, retinoblastomas and in a large subset of cervical and ovarian cancer cell lines. A systemic analysis of 500 human tumors (Danovi et al, MCB, 2004) of HDMX expression in primary tumors of different origins revealed a broad spectrum of human cancers with HDMX overexpression such as breast cancer, colon cancer, lung cancer, prostate cancer, stomach cancer, testis cancer, larynx cancer, uterus cancer, melanoma, and sarcoma.

Specific MDMX antagonists should therefore be developed as a pharmaceutical product to ensure activation of 'dormant' p53 activity in tumors that retain wild-type p53.

Although MDMX is highly homologous to MDM2, it does not possess ubiquitin ligase capability and its expression level is not p53 dependent. It was shown that MDMX could inhibit p53 transcriptional activity even stronger than MDM2 and both proteins cooperate in the inactivation of p53. Therefore, to achieve full activation of p53 in tumor cells, compounds that exhibit dual specificity for MDMX and MDM2 may be superior over MDM2 or MDMX specific binders alone.

The 3-dimensional structure of human MDMX protein bound to optimized p53 peptides have been solved by Kallen et al., *JBC,* 2009, 284, 8812-8821. The crystal structure of humanized zebra fish MDMX to p53 peptide by Popowicz et al., Cell Cycle 6:19, 2386-2392, 1 Oct. 2007 reveals that the principle features of the p53 and MDM2 interaction are preserved in the p53/MDMX complex and that "hybrid" MDM2/MDMX inhibitors could be developed. Thus, the structures of p53/MDMX and p53/MDM2 complexes show that both MDMX and MDM2 utilize the same p53-binding motif and many of the same residues for binding to p53. The overall shape of the binding sites is similar in terms of general shape and orientation of hydrophobic binding pockets, but the exact sizes respectively depths of these pockets are somewhat different. Thus, in MDMX, the hydrophobic cleft on which the p53 peptide binds appears slightly more flexible than in MDM2.

SUMMARY OF THE INVENTION

In one embodiment of the present invention, novel small molecules are described that bind to HDM2 and/or MDMX, are inhibitors of HDM2 and/or MDMX mediated biology and can be used as novel therapeutic agents, especially for the treatment of cancer and/or viral infections.

The present invention provides at least one compound selected from formula (I), (Ia), (Ic), (Id), (Ie) or (If) and pharmaceutically acceptable salts and esters thereof. Such a compound preferably is a ligand binding to HDM2 and/or MDMX protein, inducing apoptosis and inhibiting proliferation, and having therapeutic utility in cancer therapy and prevention. This therapeutic effect can be achieved by using one or more compounds of formula (I), (Ia), (Ic), (Id), (Ie) or (II) alone or in combination with other agents that are used to treat or prevent cancer.

One or more compounds of formula (I), (Ia), (Ic), (Id), (Ie) or (If) can also be used to treat or prevent cancer e.g. by protecting non-cancer cells from the deleterious effects of cytotoxic cancer treating drugs or radiotherapy. In such a treatment, a combination of either an antineoplastic agent or radiotherapy and a cytoprotective amount of at least one compound of formula (I), (Ia), (Ic), (Id), (Ie) or (If), and preferably one or more pharmaceutically acceptable excipients are used. Preferably, the compound of formula (I), (Ia), (Ic), (Id), (Ie) or (If) (also called HDM2 and/or MDMX ligand herein) is administered prior to, concurrently or after administration of the antineoplastic agent. Additionally, the HDM2 and/or MDMX inhibitor can be administered continuously or at repeated regular intervals.

A compound selected from compounds of formula (I), (Ia), (Ie), (Id), (Ic) or (If) can e.g. be used as a therapeutic agent in methods of treating stroke, myocardial infarction, ischemia, multi-organ failure, spinal cord injury, Alzheimer's Disease, injury from ischemic events, heart valvular degenerative disease or decreasing the side effects from cytotoxic agents, such as hair loss or cardio toxicity induced by doxorubicin or paclitaxel.

A compound selected from compounds of formula (I), (Ia), (Ic), (Id), (Ie) or (If) of the present invention can further be used to treat viral infections, especially in a pharmaceutical combination comprising a known antiviral compound.

Further, the present invention is directed to a pharmaceutical composition comprising a cytoprotective amount of a compound of formula (I), (Ia), (Ic), (Id), (Ie) or (If), and one or more pharmaceutically acceptable excipients that is applied before, concomitantly and or subsequent to the treatment of a patient with a cytotoxic cancer treatment such as radiation or a cytotoxic antineoplastic agent.

DETAILED DESCRIPTION OF THE INVENTION

The present invention provides one or more compounds of formula (I), (Ia), (Ic), (Id), (Ie) or (If) that are preferably small molecule ligands of the HDM2 and/or MDMX protein and prevent or reduce binding of other proteins to HDM2 and/or MDMX.

In in vitro cell-based assays, one or more compounds of the present invention inhibit the interaction of the HDM2 and/or MDMX protein with the p53 protein. In such cell-based assays, such compounds demonstrate mechanistic activity such as induction of apoptosis and inhibition of proliferation. Incubation of cancer cells with one or more compounds of formula (I), (Ia), (Ic), (Id), (Ie) or (If) leads to an accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with missing p53 at comparable compound concentrations. Therefore, the activity of HDM2 and/or MDMX antagonists is likely linked to its mechanism of action. These compounds are therefore potent and selective anticancer agents.

The present invention provides one or more compounds of formula (I)

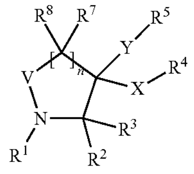

(I)

wherein

V is C═O, C═S or $CH_2$ (especially C═O);

X is sulphur, oxygen or a group of formula $CH_2$, $CR^{4b}R^{4c}$, NH, $NR^{4b}$, SO or $SO_2$ or a bond;

Y is a group of formula $CONR^6$, $CH_2NR^6$, CO, COO, $CH_2O$, $SO_2NR^6$, $NR^6CO$, $NR^6SO_2$, $NR^{5a}CONR^6$, $NR^6COO$, $OCONR^6$, $CONR^5NR^6$, $CONR^{5a}OR^6$, $CH_2CO$ $CH_2CONR^6$, $CH_2COO$, $COCR^{5a}R^6$ or a bond;

n is 1, 2, 3 or 0;

$R^1$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^2$ is a hydrogen atom or an alkyl, alkenyl, alkynyl, heteroalkyl, aryl, heteroaryl, cycloalkyl, alkylcycloallcyl, heteroalkylcycloalkyl, heterocycloalkyl, aralkyl or heteroaralkyl radical;

$R^3$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^4$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4b}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4c}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^5$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{5a}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^6$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

the residues $R^7$ are independently from each other a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

the residues $R^8$ are independently from each other a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

or two of the radicals $R^1$, $R^2$, $R^3$, $R^4$, $R^{4b}$, $R^{4c}$, $R^5$, $R^{5a}$, $R^6$, $R^7$ and $R^8$ together are part of an optionally substituted cycloalkyl, heterocycloalkyl, alkylcycloalkyl, heteroalkylcycloalkyl, heteroaryl, aralkyl or heteroarylalkyl ring system;

or a pharmaceutically acceptable salt, ester, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or CO such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom). The expression heteroalkyl furthermore refers to a carboxylic acid or to a group derived from a carboxylic acid, such as, for example, acyl, acylalkyl, alkoxy-carbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially 0 and/or N). The term $C_1$-$C_4$ heteroalkyl refers to a heteroalkyl group containing from 1 to 4 carbon atoms and 1, 2 or 3 heteroatoms selected from O, S and/or N (especially 0 and/or N). Furthermore, the term heteroalkyl refers to groups in which one or more hydrogen atoms have been replaced by a halogen atom (preferably F or Cl).

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$, $R^a$—CO—O—$Y^a$, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$, $R^a$—CS—O—$Y^a$, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—N($R^b$)—$Y^a$—, $R^a$—CO—S—$Y^a$—, $R^a$—S—CO—N($R^b$)—$Y^a$, $R^a$—N($R^b$)—CO—S—$Y^a$—, $R^a$—S—CO—O—$Y^a$—, $R^a$—O—CO—S—$Y^a$—, $R^a$—S—CO—S—$Y^a$, $R^a$—S—CS—$Y^a$, —$R^a$—CS—S—$Y^a$, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^a$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-pro-pyloxy, isopropyloxy, butoxy, tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexanone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups in which one or more hydrogen atoms have been replaced by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). The expression heteroaryl refers furthermore to groups in which one or more hydrogen atoms have been replaced by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indene. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced by fluorine, chlorine, bromine or iodine atoms or by OH, SH, =S, $NH_2$, $N_3$ or $NO_2$ groups.

The expression "optionally substituted" especially refers to groups in which one, two, three or more hydrogen atoms have been replaced by fluorine, chlorine, bromine or iodine atoms or by OH, =O, SH, $NH_2$, =NH, $N_3$ or $NO_2$ groups. This expression refers furthermore to groups that are substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Preferred substituents are F, Cl, Br, Me, OMe, CN or $CF_3$.

Preferably, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted, Preferred are compounds of formula (I) wherein the radicals $R^5$ and $R^6$ together are part of an optionally substituted heterocycloalkyl, heteroalkylcycloalkyl, heteroaryl or heteroarylalkyl ring system, and/or wherein $R^2$ and $R^3$ together are part of an optionally substituted cycloalkyl, alkylcycloalkyl, heteroalkylcycloalkyl, heterocycloalkyl, aralkyl or heteroaralkyl ring system.

Preferred are compounds of formula (I) wherein X is sulphur, oxygen, NH, $CH_2$, SO, $SO_2$, especially sulphur.

Further preferred are compounds of formula (I) wherein Y is a group of formula $CONR^6$.

Further preferred are compounds of formula (I) wherein n is 0 or 1, especially 1.

Further preferred are compounds of formula (I) wherein $R^7$ is hydrogen.

Moreover preferred are compounds of formula (I) wherein $R^8$ is hydrogen.

Especially preferred are compounds of formula (Ia)

(Ia)

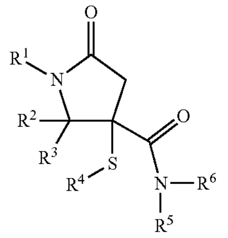

wherein $R^1$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^2$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^3$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^4$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^5$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^6$ is a hydrogen atom or an alkyl, alkenyl, alkynyl, heteroalkyl, aryl, heteroaryl, cycloalkyl, alkylcycloalkyl, heteroalkyleycloalkyl, heterocycloalkyl, aralkyl or heteroaralkyl radical;

or the radicals $R^5$ and $R^6$ together are part of an optionally substituted heterocycloalkyl, heteroalkylcycloalkyl, heteroaryl or heteroarylalkyl ring system, and/or $R^2$ and $R^3$ together are part of an optionally substituted cycloalkyl, alkylcycloalkyl, heterocycloalkyl, heteroalkylcycloalkyl, aralkyl or heteroaralkyl ring system;

or a pharmaceutically acceptable salt, ester, solvate or hydrate or a pharmaceutically acceptable formulation thereof.

Further preferred are compounds of formula (I) or (Ia), wherein $R^1$ is a cycloalkyl, alkylcycloalkyl, heterocycloalkyl, heteroalkylcycloalkyl, aryl, heteroaryl, aralkyl or heteroaralkyl radical.

Further preferred are compounds of formula (I) or (Ia), wherein $R^1$ is an aryl, heteroaryl, aralkyl or heteroaralkyl radical.

Further preferred are compounds of formula (I) or (Ia), wherein $R^1$ is a group of formula -A-Ar or -A-Cy (especially -A-Ar) wherein A is a bond, $C_1$-$C_4$ alkyl (especially a bond, $CH_2$ or $CH(CH_3)$) or $C_1$-$C_6$ heteroalkyl (e.g. $CH(CH_2N(CH_3)_2)$), or wherein A is a group of formula —$CHR^{1a}$— wherein $R^{1a}$ is a $C_1$-$C_6$ heteroalkyl group, Cy is an optionally substituted $C_3$-$C_7$ cycloalkyl group or an optionally substituted heterocycloalkyl group containing from 3 to 7 ring atoms and Ar is an optionally substituted (e.g. by 1, 2 or 3 substituents) phenyl ring or an optionally substituted (e.g. by 1, 2 or 3 substituents) heteroaryl ring containing 5 or 6 ring atoms (especially including from 1 to 3 heteroatoms selected from O, S and N), especially preferably Ar is an optionally substituted phenyl or an optionally substituted pyridyl residue (e.g. a 4-bromobenzyl residue). Preferred substituents are F, Cl, Br, CN, $CH_3$, $OCH_3$ and $CF_3$.

Further preferred are compounds of formula (I) or (Ia), wherein $R^1$ is a group of formula -A-Ar wherein A is a bond or $C_1$-$C_4$ alkyl (especially a bond, $CH_2$ or $CHCH_3$) and Ar is an optionally substituted (e.g. by 1, 2 or 3 substituents) phenyl ring or an optionally substituted (e.g. by 1, 2 or 3 substituents) heteroaryl ring containing 5 or 6 ring atoms (especially containing from 1 to 3 heteroatoms selected from O, S and N), especially preferably Ar is an optionally substituted phenyl or an optionally substituted pyridyl residue (e.g. a 4-bromobenzyl residue).

Especially preferably, $R^1$ is a group of formula -A-phenyl (especially —$CH_2$-phenyl) which is optionally substituted, preferably by one or two halogen atoms selected from F, Cl and Br and wherein A is preferrably a group of formula —$CHR^{1a}$— wherein $R^{1a}$ is a $C_1$-$C_6$ heteroalkyl group (e.g. COOH, $CH_2COOH$)

Further preferred, $R^1$ is cyclopropylmethyl, picolyl, phenylbenzyl or phenoxybenzyl, all of which may optionally be substituted.

Further preferred are compounds of formula (I) or (Ia), wherein $R^2$ is hydrogen.

Further preferred are compounds of formula (I) or (Ia), wherein $R^3$ is $C_1$-$C_6$ alkyl, an aryl (especially phenyl), heteroaryl, aralkyl or heteroaralkyl residue, all of which may be substituted (e.g. by 1, 2 or 3 substituents). Especially preferably, $R^3$ is an optionally substituted phenyl group, an optionally substituted benzyl group or an optionally substituted heteroaryl residue having 1 or 2 rings and from 5 to 10 ring atoms (especially 2 rings and a total of 9 ring atoms) including 1, 2, 3 or 4 heteroatoms selected from O, S and N (especially N). Preferred substituents are F, Cl, Br, $C_1$-$C_4$ alkyl groups (e.g. $CH_3$) and $C_1$-$C_6$ heteroalkyl groups (e.g. $CH_2SO_3^-$, $(CH_2)_5NH_2$).

Further preferred are compounds of formula (I) or (Ia), wherein $R^3$ has the following structure

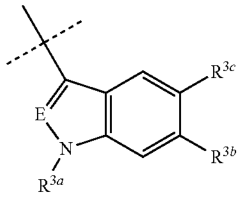

wherein E is N or CH, $R^{3a}$ is H, $C_1$-$C_6$ alkyl or $C_1$-$C_6$ heteroalkyl (especially H or $CH_3$), $R^{3b}$ is H, F, Cl, Br, $CH_3$, $OCH_3$ or $CF_3$ and $R^{3c}$ is H, F, Cl, Br, $CH_3$, $OCH_3$ or $CF_3$ (especially preferably, E is CH, $R^{3a}$ is H, $R^{3b}$ is Cl and $R^{3c}$ is H).

Further preferred are compounds of formula (I) or (Ia), wherein $R^3$ is an aryl (especially phenyl), heteroaryl, aralkyl or heteroaralkyl residue, all of which may be substituted (e.g. by 1, 2 or 3 substituents); especially preferably, $R^3$ is an optionally substituted heteroaryl residue having 1 or 2 rings and from 5 to 10 ring atoms (especially 2 rings and a total of 9 ring atoms) including 1, 2, 3 or 4 heteroatoms selected from O, S and N (especially N).

Further preferred are compounds of formula (I) or (Ia), wherein $R^3$ has the following structure

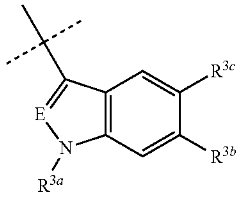

wherein F is N or CH, $R^{ia}$ is H or $CH_3$, $R^{3b}$ is F, Cl or Br and $R^{3c}$ is H, F, Cl or Br (especially preferably, E is CH, $R^{3a}$ is H, $R^{3b}$ is $C^1$ and $R^{Rc}$ is H).

Further preferred, $R^2$ and $R^3$ together are part of an optionally substituted heterocycloalkyl or heteroaralkyl ring. Moreover preferred, $R^2$ and $R^3$ together are part of a group having the following structure:

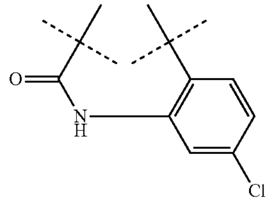

Further preferred are compounds of formula (I) or (Ia), wherein $R^4$ is $C_1$-$C_6$ alkyl, $C_2$-$C_6$ alkenyl, optionally substituted $C_1$-$C_4$ alkyl-$C_3$-$C_7$ cycloalkyl, an optionally substituted phenyl ring, an optionally substituted benzyl group or an optionally substituted heteroaryl ring having 5 or 6 ring atoms including from 1 to 3 heteroatoms selected from O, S and N (e.g. pyridyl). Especially preferably, $R^4$ is a phenyl ring which is substituted by 1 or 2 substituents, preferably selected from F, Br, Cl, I, $NO_2$, methyl or cyanide (e.g. 4-methylphenyl), or an unsubstituted phenyl ring. Moreover preferably, $R^4$ is phenyl or 4-methylphenyl.

Further preferred are compounds of formula (I) or (Ia), wherein $R^4$ is $C_1$-$C_6$ alkyl or an optionally substituted phenyl ring or an optionally substituted heteroaryl ring having 5 or 6 ring atoms and containing from 1 to 3 heteroatoms selected from O, S and N. Especially preferably, $R^4$ is a phenyl ring which is substituted by 1 or 2 substituents, preferably selected from F, Br, Cl, I, methyl or cyanide (e.g. 4-methylphenyl).

Further preferred are compounds of formula (I) or (Ia), wherein $R^5$ is an alkyl, heteroalkyl, heterocycloalkyl, heteroalkylcycloalkyl or heteroaralkyl group, all of which groups may be substituted.

Further preferred are compounds of formula (I) or (Ia), wherein $R^5$ is selected from the following groups: $C_1$-$C_6$ alkyl; heteroalkyl containing 1-6 carbon atoms and 1, 2 or 3 heteroatoms selected from O, S and N; heteroalkylcycloalkyl comprising a $C_1$-$C_4$ alkyl group or a $C_1$-$C_4$ heteroalkyl group and an optionally substituted heterocycloalkyl group containing 5 or 6 ring atoms and 1, 2 or 3 heteroatoms selected from O, S and N; heteroaralkyl comprising a $C_1$-$C_4$ alkyl group or a $C_1$-$C_4$ heteroalkyl group and an optionally substituted heteroaryl group containing 5 or 6 ring atoms including 1, 2 or 3 heteroatoms selected from O, S and N; optionally substituted heteroaryl containing 5 or 6 ring atoms including 1, 2 or 3 heteroatoms selected from O, S and N; and optionally substituted heterocycloalkyl containing 5 or 6 ring atoms and 1, 2 or 3 heteroatoms selected from O, S and N.

Further preferred are dimers of compounds of formulas (I) and/or (Ia) that are linked via a heteroalkyl, heteroalkylcycloalkyl or a heteroaralkyl group, preferably via $R^5$.

Further preferred are compounds of formula (I) or (Ia), wherein $R^5$ is $C_1$-$C_6$ alkyl; heteroalkyl containing 1-6 carbon atoms and 1, 2 or 3 heteroatoms selected from O, S, N; heteroalkylcycloalkyl comprising a $C_1$-$C_4$ alkyl group and an optionally substituted heterocycloalkyl group containing 5 or 6 ring atoms and 1, 2 or 3 heteroatoms selected from O, S and N; heteroaralkyl comprising a $C_1$-$C_4$ alkyl group and an optionally substituted heteroaryl group containing 5 or 6 ring atoms and 1, 2 or 3 heteroatoms selected from O, S and N.

Further preferred are compounds of formula (I) or (Ia), wherein $R^6$ is hydrogen or $C_1$-$C_4$ alkyl, especially hydrogen.

Further preferred are compounds of formula (I) or (Ia), wherein $R^5$ and $R^6$ together with the nitrogen atom to which they are bound form an optionally substituted (e.g. by 1, 2 or 3 substituents) heterocycloalkyl ring containing 4, 5, 6 or 7 ring atoms and 1, 2 or 3 heteroatoms selected from O, S and N.

Moreover preferred, $R^5$ and $R^6$ together with the nitrogen atom to which they are bound form the following group:

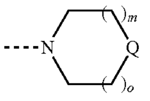

Therein, m is 0, 1 or 2; o is 0, 1 or 2; the sum of m and o is preferably from 0 to 3; Q is N—$R^{6x}$, $CR^{6y}R^{6z}$, C═O, —CO—$NR^{6x}$—, —$NR^{6x}$—CO—$NR^{6y}$—, —$SO_2$—$NR^{6x}$—, —SO—$NR^{6x}$— or —O—CO—$NR^{6x}$—, wherein $R^{6x}$, $R^{6y}$ and $R^{6z}$ independently from each other are a hydrogen atom, OH, $NH_2$, SH or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical.

Preferably, Q is N—CO—$R^{6a}$, $NR^{6b}$ or $CHR^{6c}$ wherein $R^{6a}$ is $C_1$-$C_6$ alkyl, $C_1$-$C_6$ heteroalkyl, $NH_2$, optionally substituted phenyl or hydrogen; $R^{6b}$ is optionally substituted phenyl or optionally substituted heteroaryl containing 5 or 6 ring atoms including one or two heteroatoms selected from O, S or N; $R^{6c}$ is $C_1$-$C_6$ heteroalkyl, $NH_2$ or OH.

Further preferred, Q is N—CO—$NHR^{6d}$, N—$COOR^{6e}$, N—$SO_2R^{6f}$, N—$SO_2NHR^{6g}$, N—$NHCOR^{6h}$, CH—$NH_2$, CH—OH, CH—SH, CH—NH—$COR^{6i}$, CO, CONH, NHCONH, $SO_2NH$, OCONH, CH—COOH, CH—$COOR^{6j}$, CH—$COR^{6k}$ or CH—$SO_2R^{6l}$, wherein $R^{6d}$, $R^{6e}$, $R^{6f}$, $R^{6g}$, $R^{6h}$, $R^{6i}$, $R^{6j}$, $R^{6k}$ and $R^{6l}$ independently from each other are a hydrogen atom, OH, $NH_2$, SH or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical, especially hydrogen or a $C_1$-$C_6$ alkyl group or a $C_1$-$C_6$ heteroalkyl group.

Preferably, Q is N—CO—$R^{6a}$ wherein $R^{6a}$ is preferably $NH_2$, $C_1$-$C_6$ alkyl, NH—$C_1$-$C_6$ alkyl or N($C_1$-$C_6$ alkyl)$_2$.

Further preferrably, group Q contains a hydrogen bond acceptor (especially an atom or group having a lone electron pair like e.g. an electronegative atom such as fluorine, oxygen, or nitrogen).

Further preferred, o is 1 and m is 1.

Especially preferably, m is 1, o is 1 and Q is N—CO—$R^{6a}$. Thereby $R^{6a}$ is preferably $C_1$-$C_4$ alkyl or NH—$C_1$-$C_4$ alkyl (e.g. $CH_3$ or $NHCH_2CH_3$).

Especially preferred are compounds of formula (I) or (Ia), wherein $R^5$ and $R^6$ together are part of an optionally substituted (e.g. by 1, 2 or 3 substituents like e.g. ═O) piperazine ring.

Further preferred are compounds of formula (I) or (Ia), wherein $R^5$ and $R^6$ together are part of an optionally substituted (e.g. by 1, 2 or 3 substituents) heterocycloalkyl ring containing 5 or 6 ring atoms and 1, 2 or 3 heteroatoms selected from O, S and N Further preferred are compounds of formula (Ic):

(Ic)

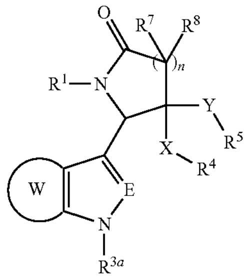

wherein W is an optionally substituted phenyl ring or an optionally substituted heteroaryl group having 5 or 6 ring atoms including 1 or 2 heteroatoms selected from O, S and N; and wherein $R^1$, $R^{1a}$, $R^4$, $R^5$, $R^7$, $R^8$, E, X, Y and n are defined as above.

Especially preferred are compounds of formula (Ie) wherein W is an optionally substituted phenyl ring (preferably substituted by 1, 2 or 3 halogen atoms selected from F, Cl and Br); $R^1$ is an optionally substituted benzyl group (preferably substituted by 1, 2 or 3 halogen atoms selected from F, Cl and Br); X is S; Y is $CONR^6$; n is 1; $R^{3a}$ is hydrogen; $R^4$ is an optionally substituted phenyl group (preferably unsubstituted or substituted by a methyl group, especially in the para position); $R^7$ and $R^8$ are hydrogen; E is CH; and $R^5$ and $R^6$ are defined as above; especially preferably, $R^5$ and $R^6$ together are part of an optionally substituted piperazine ring (especially as defined above).

Further preferred are compounds of formula (Id):

(Id)

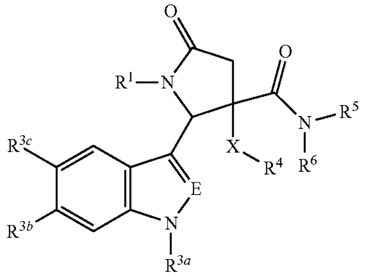

wherein $R^1$, $R^{3a}$, $R^{3b}$, $R^{3c}$, $R^4$, $R^5$, $R^6$, E and X are defined as above.

Especially preferred are compounds of formula (Id) wherein $R^1$ is an optionally substituted benzyl group (preferably substituted by 1, 2 or 3 halogen atoms selected from F, Cl and Br); X is S; $R^{3a}$ is hydrogen; $R^{3b}$ is Cl; $R^{3c}$ is hydrogen, $R^4$ is an optionally substituted phenyl group (preferably unsubstituted or substituted by a methyl group, especially in the para position); E is CH; and $R^5$ and $R^6$ are defined as above; especially preferably, $R^5$ and $R^6$ together are part of an optionally substituted piperazine ring (especially as defined above).

Further preferred are compounds of formula (Ie):

(Ie)

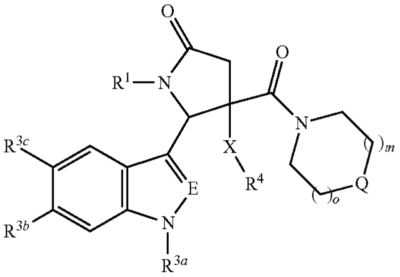

wherein $R^1$, $R^{3a}$, $R^{3b}$, $R^{3c}$, $R^4$, E, Q, m, o and X are defined as above.

Especially preferred are compounds of formula (Ie) wherein $R^1$ is an optionally substituted benzyl group (preferably substituted by 1, 2 or 3 halogen atoms selected from F, Cl and Br); X is S; $R^{3a}$ is hydrogen; $R^{3b}$ is Cl; $R^{3c}$ is hydrogen, $R^4$ is an optionally substituted phenyl group (preferably unsubstituted or substituted by a methyl group, especially in the para position); E is CH; Q is N—CO—$R^{6a}$ wherein $R^{6a}$ is preferably $C_1$-$C_6$ alkyl, NH—$C_1$-$C_6$ alkyl or N($C_1$-$C_6$ alkyl)$_2$; m is 0, 1 or 2; o is 0, 1 or 2; and the sum of m and o is preferably from 0 to 3. Especially preferably, m is 1, o is 1 and Q is N—CO—$R^{6a}$, wherein $R^{6a}$ is preferably $C_1$-$C_4$ alkyl or NH—$C_1$-$C_4$ alkyl (e.g. $CH_3$ or $NHCH_2CH_3$).

Further preferred are compounds of formula (If)

(If)

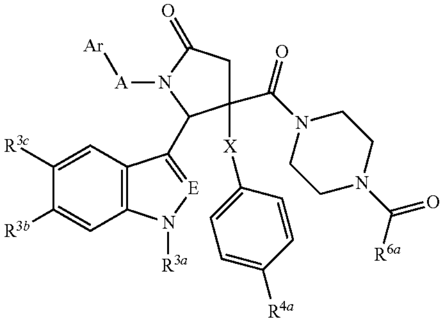

wherein A, Ar, $R^{3a}$, $R^{3b}$, $R^{3c}$, E, X, $R^{4a}$ and $R^{6a}$ are defined as above.

Especially preferred are compounds of formula (If) wherein X is S; $R^{3a}$ is hydrogen; $R^{3b}$ is Cl; $R^{3c}$ is hydrogen, $R^{4a}$ is hydrogen or a methyl group; E is CH; A is $CH_2$; Ar is phenyl which is substituted by one or two halogen atoms selected from F, Cl and Br; and $R^{6a}$ is $C_1$-$C_4$ alkyl or NH—$C_1$-$C_4$ alkyl (e.g. $CH_3$ or $NHCH_2CH_3$).

A further preferred embodiment of the present invention relates to compounds of formula (I) or (Ia), wherein $R^1$ is aryl, heteroaryl, arylalkyl or heteroarylalkyl, all of which may be substituted by F, Br, Cl, 1, methyl or cyanide, $R^2$ is hydrogen, $R^3$ is aryl, heteroaryl, arylalkyl or heteroarylalkyl, all of which may be substituted by F, Br, Cl, 1, methyl or cyanide, $R^4$ is aryl, heteroaryl, arylalkyl or heteroarylalkyl, $R^5$ and $R^6$ are independently selected from hydrogen, alkyl, heteroalkyl, aryl, alkenyl, akinyl, cycloalkyl, heterocycloalkyl, aryl, heteroaryl, arylalkyl or heteroarylalkyl, or wherein $R^5$ and $R^6$ may be part of one heteroaryl, heterocycloalkyl, heteroalkylcycloalkyl or heteroarylalkyl ring system, and wherein the other residues and groups are defined as above.

A further preferred embodiment of the present invention relates to compounds of formula (I) or (Ia), wherein $R^1$ is aryl, heteroaryl, arylalkyl or heteroarylalkyl, all of which may be substituted by F, Br, Cl, 1, methyl or cyanide, $R^2$ and $R^3$ together are part of a heteroaryl, heteroaralkyl, heterocycloalkyl or heteroalkylcycloalkyl ring system such as but not restricted to 1,3-dihydroindole, dihydro-indol-2-one, 2,3-dihydro-1H-indazole, tetrahydro-quinoline, tetrahydro-quinoline-2-one, 3,4-dihydro-1H-quinolin-2-one, 3,4-dihydro-1H-quinazolin-2-one, all of which may be substituted by F, Br, Cl, I, methyl or cyanide, $R^4$ is selected from aryl, heteroaryl, arylalkyl or heteroarylalkyl, $R^5$ and $R^6$ are independently selected from hydrogen, alkyl, heteroalkyl, aryl, alkenyl, akinyl, cycloalkyl, heterocycloalkyl, aryl, heteroaryl, arylalkyl or heteroarylalkyl, or wherein $R^5$ and $R^6$ may also be part of one heteroaryl, heterocycloalkyl, heteroalkylcycloalkyl or heteroarylalkyl ring system, and wherein the other residues and groups are defined as above.

A further preferred embodiment of the present invention relates to compounds of formula (I), (Ia), (Ic), (Id), (Ie) or (If), wherein $R^3$ and the sulfanyl group (i.e. the group carrying X) bearing the $R^4$ group are in cis position (especially when $R^2$ is H).

An especially preferred embodiment are enantiomerically pure compounds of formula (I), (Ia), (Ic), (Id), (Ie) or (If).

Further preferred is the following compound:
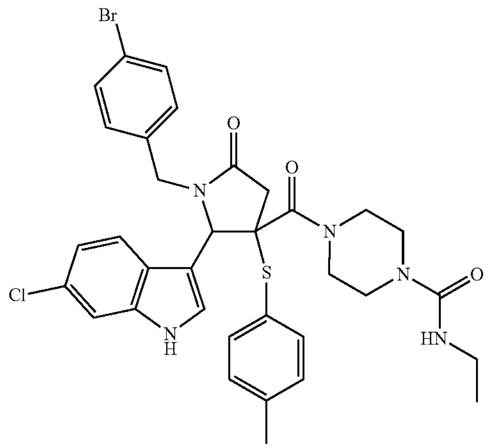
4-[1-(4-Bromo-benzyl)-2-(6-chloro-1H-indol-3-yl)-5-oxo-3-p-tolylsulfanyl-pyrrolidine-3-carbonyl]-piperazine-1-carboxylic acid ethylamide
i.e. the following diastereomers:
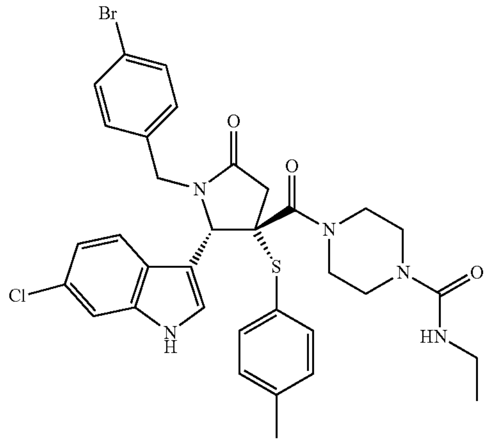
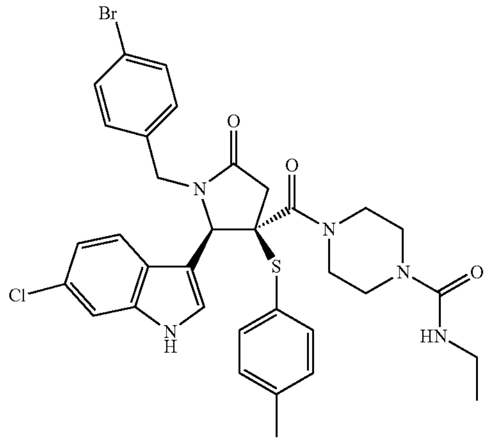
-continued
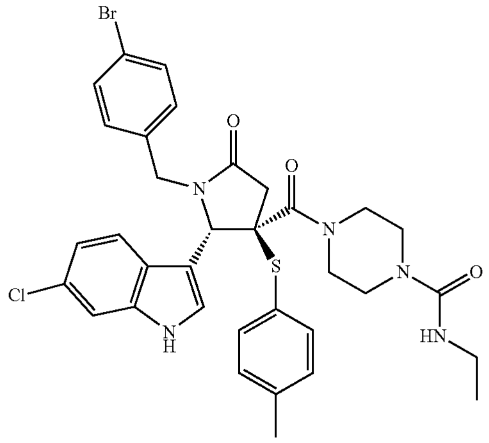
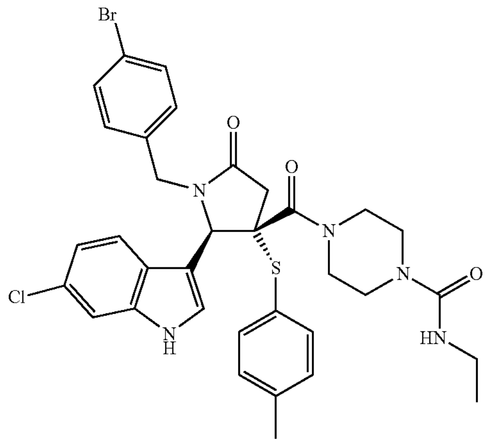
especially the following diastereomer:
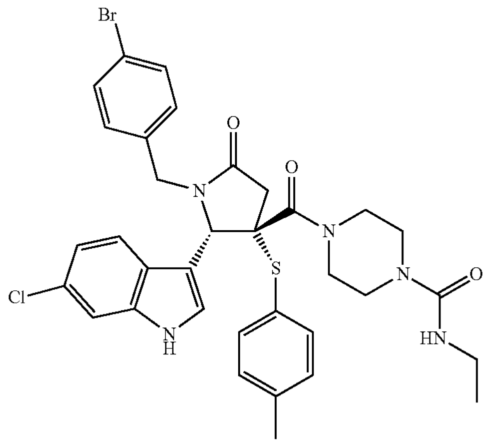
4-[1-(4-Bromo-benzyl)-2-(6-chloro-1H-indol-3-yl)-5-oxo-3-p-tolylsulfanyl-pyrrolidine-3-carbonyl]-piperazine-1-carboxylic acid ethylamide Further preferred is the following compound:
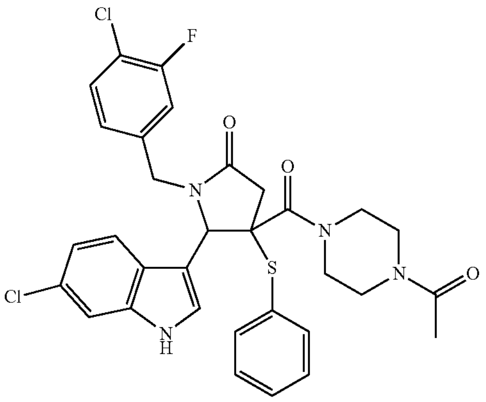
4-(4-Acetyl-piperazine-1-carbonyl)-1-(4-chloro-3-fluoro-benzyl)-5-(6-chloro-1H-indol-3-yl)-4-phenylsulfanyl-pyrrolidin-2-one
i.e. the following diastereomers:
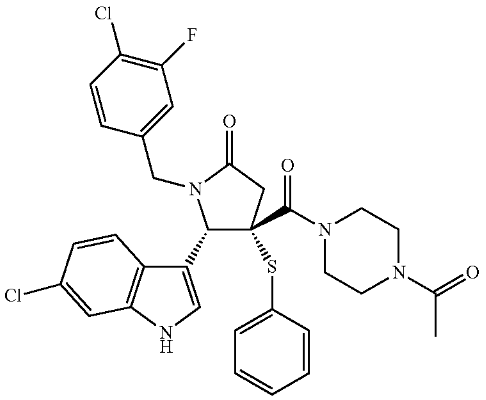 [SMILES: CC(=O)N1CCN(C(=O)[C@]2(Sc3ccccc3)CC(=O)N(Cc3ccc(Cl)c(F)c3)[C@H]2c2c[nH]c3cc(Cl)ccc23)CC1]
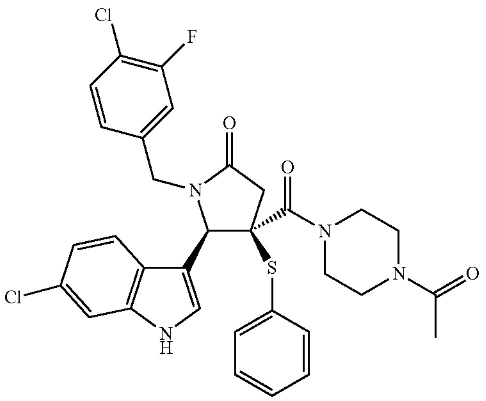
-continued
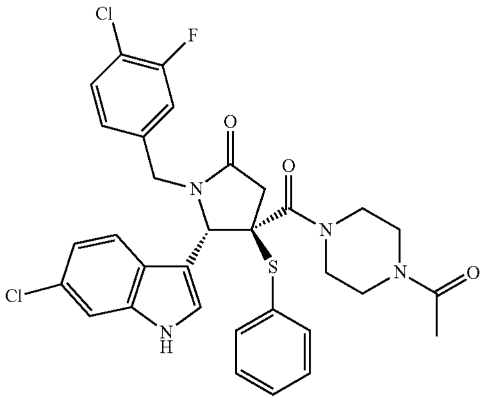
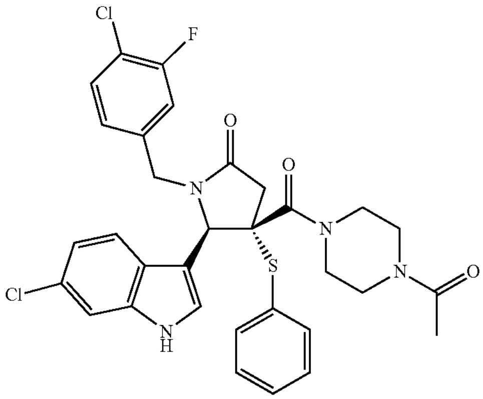
especially the following diastereomer:
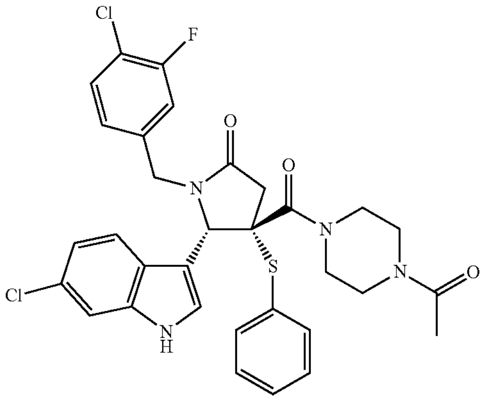

Further preferred is the following compound:

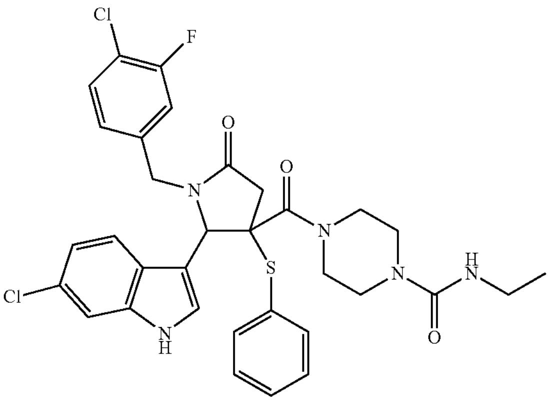

4-[1-(4-Chloro-3-fluoro-benzyl)-2-(6-chloro-1H-indol-3-yl)-5-oxo-3-phenylsulfanyl-pyrrolidine-3-carbonyl]-piperazine-1-carboxylic acid ethylamide i.e. the following diastereomers.

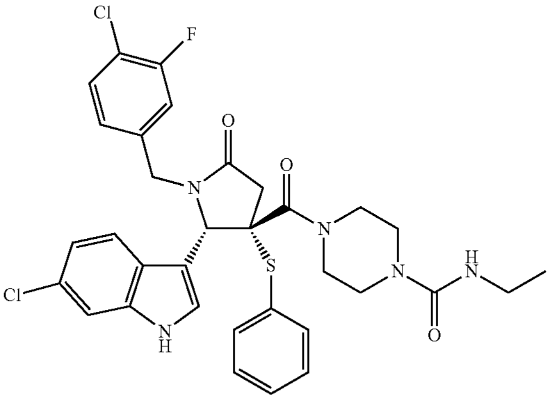 [SMILES: CCNC(=O)N1CCN(C(=O)[C@]2(Sc3ccccc3)CC(=O)N(Cc3ccc(Cl)c(F)c3)[C@H]2c2c[nH]c3cc(Cl)ccc23)CC1]

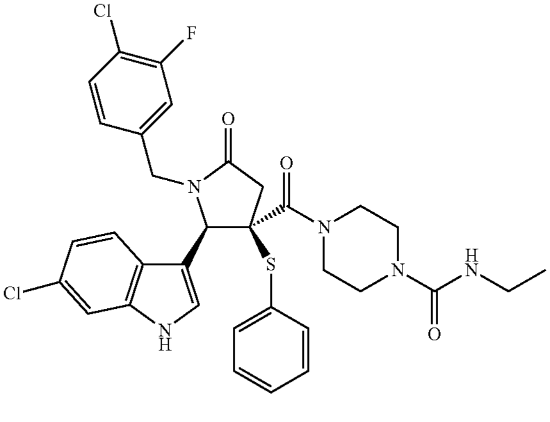

-continued

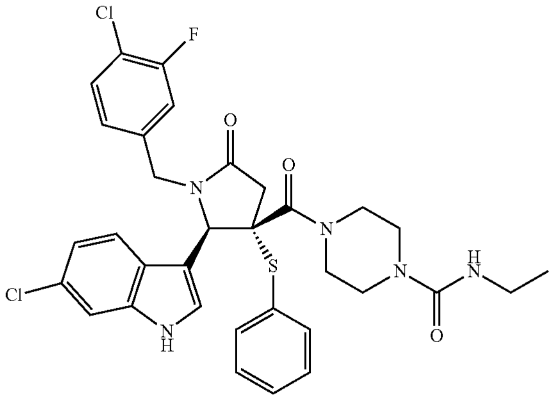

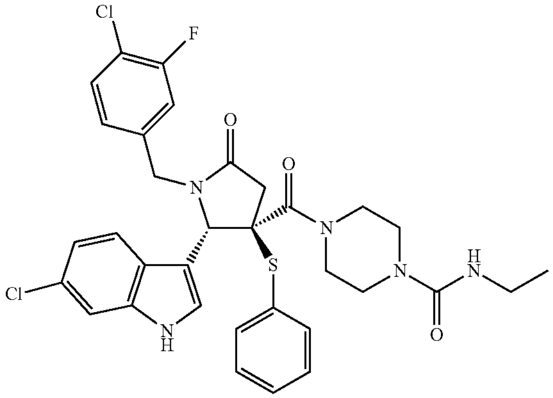

especially the following diastereomer:

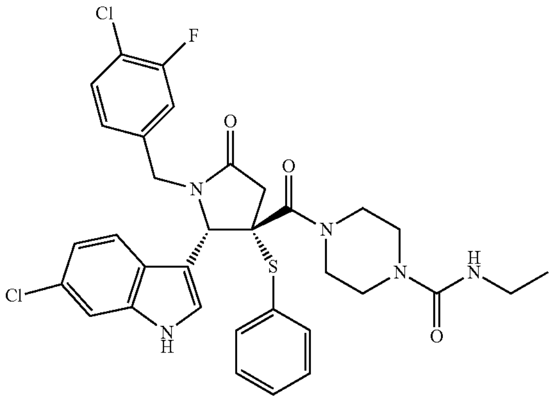

Preferably, the compounds described in:

1. Ng et al. Angew. Chem. Int. Ed. 2007, 46, 5352-5355 and
2. Ng et al. Organic Letters 2006, Vol. 8, No. 18, 3999-4002 (and supporting information thereof) are excluded from the scope of the present application and/or patent.

Further preferred, one or more of the following compounds are excluded from the present application and/or patent:

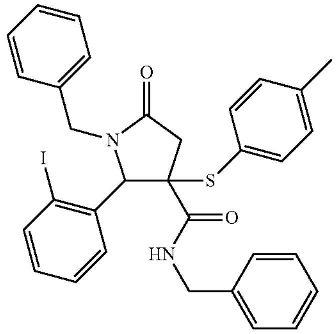
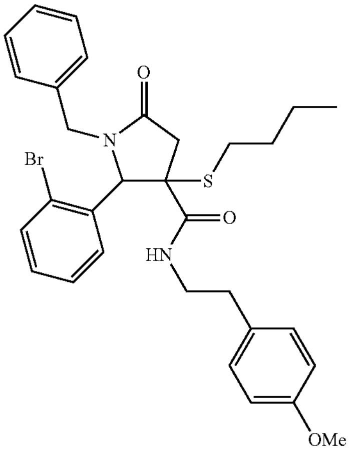
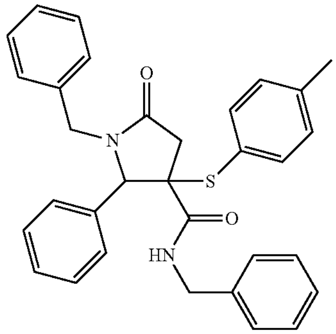
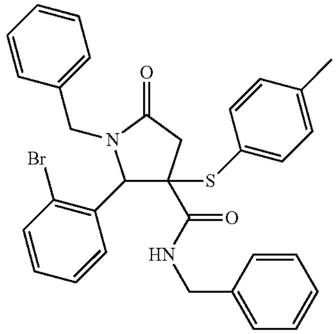
Further preferred, also the following compounds are excluded from the present application and/or patent:
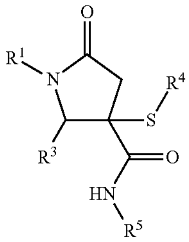
wherein $R^3$ is p-$C_6H_5CH_2OH$ (or a derivative thereof which is bound to the solid phase as described in Ng et al. Angew. Chem. Int. Ed. 2007, 46, 5352-5355), $R^1$ is selected from the following groups:
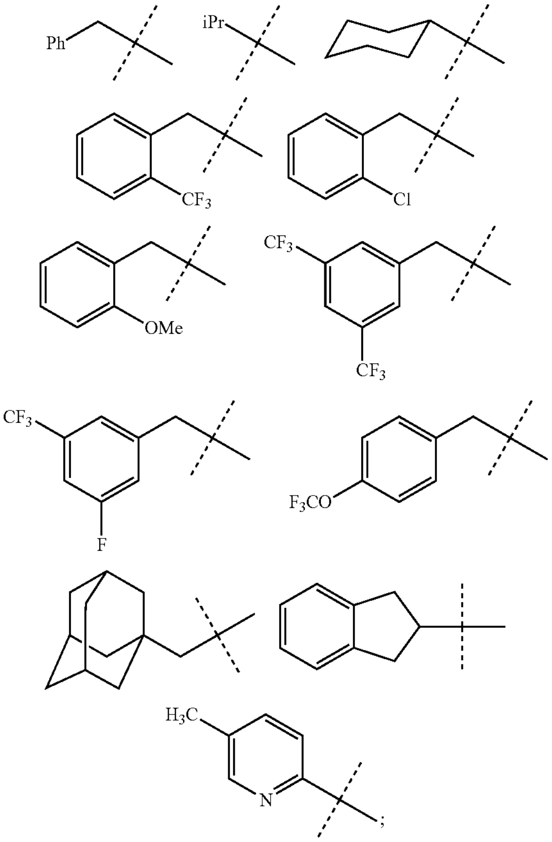
;
$R^4$ is para-$C_6H_5CH_3$ and $R^5$ is selected from the following groups:
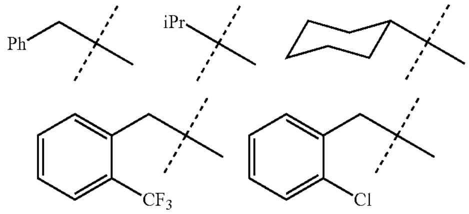

-continued

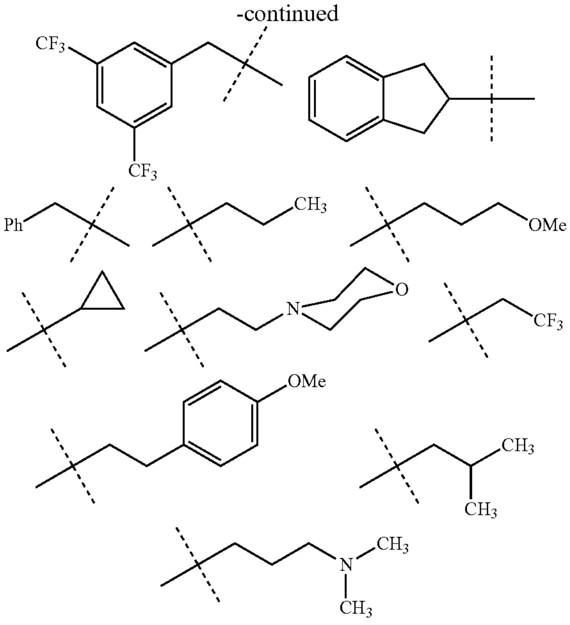

All those compounds are described in Ng et al. Angew. Chem., Int. Ed. 2007, 46, 5352-5355.

Further preferred, compounds of formula (I) or (Ia) are excluded wherein $R^3$ is p-$C_6H_5CH_2OH$ (or a derivative thereof which is bound to the solid phase as described in Ng et al. Angew. Chem. Int. Ed. 2007, 46, 5352-5355).

Further preferred, also the following compounds are excluded from the present application and/or patent (X=H, I):

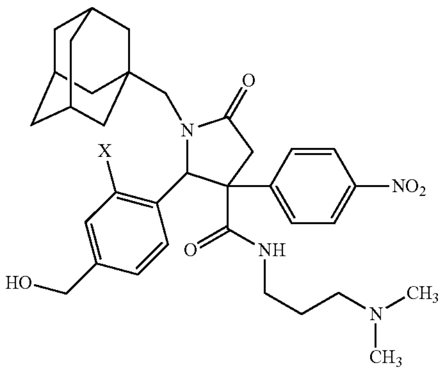

The present invention further provides pharmaceutical compositions comprising a compound of formula (I), (Ia), (Ic), (Id), (Ie) or (If) as defined herein or a pharmaceutically acceptable ester, prodrug, hydrate, solvate or salt thereof, optionally in combination with a pharmaceutically acceptable carrier.

A further preferred embodiment of the present invention relates to pharmaceutical compositions comprising one or more compounds of formula (I), (Ia), (Ic), (Id), (Ie) or (If) as defined herein or a pharmaceutically acceptable ester, prodrug, hydrate, solvate or salt thereof, optionally in combination with a pharmaceutically acceptable carrier, further comprising one or more other anti-tumor agents, wherein the anti-tumor agent is especially selected from 16-Aza-epothilone B, Aldesleukin, Amifostine, Aranose, Bevacizumab, Bleocin, Bleomycin, BMS-184476, Bortezomib, Calcitriol, Carmustine, Canertinib, Canfosfamide, Capecitabine, Carboplatin, Carmustine, Cefixime, Ceftriaxone, Celecoxib, Celmoleukin, Cetuximab, Ciclosporin, Cisplatin, Clodronate, Cyclophosphamide, Cytarabine, Deoxorubicin, Desoxyepothilone B, Diethylstilbestrol, Diflomotecan, Docetaxel, Doxorubicin, Edatrexate, Efaproxiral, EKB-569, Epirubicin, Epratuzumab, Erlotinib, Etoposide, ET-18-OCH3, Exatecan, Fludarabine, Fluorouracil, Folinic acid, Galarubicin, Gefinitib, Gemcitabine, Gemtuzumab, Gimatecan, Glufosfamide, Granisetron, Homoharringtonine, Hyaluronic acid, Ibandronate, Ibritumomab, Ifosfamide, Imatinib, Interferon alfa, Interferon alfa-2a, Interferon alfa-2b, Irinotecan, Isoflavone, Isotretinoin, Ixabepilone, Ketoconazole, Lapatinib, Leflunomide, Lenograstim, Leucovorin, Lexidronam, Linezolid, Lometrexol, Lurtotecan, MEN10755, Methotrexate, Mitomycin, Neridronate, Nimesulide, Nitroglycerin, 06-Benzyl guanine, Omeprazole, Ortataxel, Oxaliplatin, Paclitaxel, Patupilone, Pegfilgrastim, PEG-filgrastim, Pelitinib, Pemetrexed, Pentostatin, Perifosine, Plevitrexed, Polyprenoic acid, Quinupristin, Raloxifene, Raltitrexed, Ramosetron, Retinoic acid, Risedroante, Rituximab, Rofecoxib, Rubitecan, S-9788, Sabarubicin, Sargramostim, Satraplatin, SN-38, Sorafenib, Suberanilohydroxamic acid, Sutent, Tamoxifen, Taxotere, Tazarotene, Tegafur, Temozolamide, Tesmilifene, Tetrodotoxin, Thalidomide, Tipifarnib, Topotecan, Trabectedin, Trastuzumab, Traszutumab, Tretinoin, Vatalanib, Vincristine, Vinorelbine, Vinscristine, ZD-6474, Zoledronate or Zosuquidar.

In a preferred embodiment, the compounds of the present invention sensibilize cancer cells for radio and/or chemotherapy whereas they display chemoprotective and/or radioprotective activity on healthy cells. Thereby the dosage of these therapies can be better adjusted.

A further preferred embodiment of the present invention relates to a pharmaceutical composition comprising one or more compounds of formula (I), (Ia), (Ic), (Id), (Ie) or (If) as defined herein or one or more pharmaceutically acceptable esters, prodrugs, hydrates, solvates or salts thereof, optionally in combination with a pharmaceutically acceptable carrier. The pharmaceutical composition optionally comprises one or more antiviral agents. Preferably, the antiviral agent is selected from 3TC, Abacavir, Adefovir Dipivoxil, Acyclovir, Amprenavir, Amantadine, Amoxovir, AZT, Clevudine, Delavirdine, d4T, Emtricitabine, Entecavir, Famciclovir, Ganciclovir, Indinavir, Lamivudine, Nelfinavir, Nevirapine, Oseltamavir, Rimantadine, Ritonavir, Saquinavir, Septrin, Telbivudine, Tenofovir, Valacyclovir, Valtorcitabine, Valopicitabine or Zanamivir.

It is a further object of the present invention to provide a compound of formula (I), (Ia), (Ic), (Id), (Ie) or (If) as defined herein or a pharmaceutical composition as defined herein for the preparation of a medicament for the treatment of cancer and/or viral infections The compounds selected from formula (I), (Ia), (Ic), (Id), (Ie) or (If) of the present invention are e.g. HDM2 and/or MDMX ligands and show binding affinities from about 1 nM to about 100 μM to HDM2 and/or MDMX, preferably from about 1 nM to about 10 μM, especially to about 1 μM, preventing binding of p53 and other proteins, inhibition of proliferation and induction of apoptosis in cell based assays, especially in the assays described herein.

The compounds of the present invention are useful in the treatment or control of cell proliferative disorders, in particular oncological disorders. These compounds and formulations containing said compounds are useful in the treatment or control of solid tumors, such as, for example, breast, colon, lung and prostate tumors, as well as osteosarcoma, acute myeloid leukaemia, sporadic endometrial cancer, melanoma, malignant melanoma, soft tissue Sarcoma, B-cell chronic lymphocytic leukaemia, gastric cancers, cervical cancer, hepatocellular carcinoma, and colorectal cancer.

The compounds described herein are especially useful for the treatment and/or prevention of cancers associated with overexpression of HDM2 and/or MDMX.

Accordingly the compounds of the present invention are especially useful for the treatment and/or prevention of the following cancers associated with MDM2 and/or MDMX:

MDM2 is amplified in 7% of all human cancers. Gene amplification was observed in 19 tumor types, with the highest frequency observed in soft tissue tumors (20%), osteosarcomas (16%) and esophageal carcinomas (13%). Tumors which showed a higher incidence of MDM2 amplification than p53 mutation were soft tissue tumors, testicular germ cell cancers and neuro-blastomas (Momand et al, NAR, 1998). Naturally occurring polymorphism (SNP309) occurring within the MDM2 promoter leads to an increase in MDM2 transcription and translation. The overall frequency of MDM2 amplification in these human tumors was 7%. It is a common event in hematological malignancies. A list of cancers with a wild type of p53 gene that is sensitive to MDM2 inhibitors includes: B-cell CLL (chronic lymphocytic leukemia) (Coll-Muler et al, Blood, 2006), AML (Kojima et al, Blood, 2005), multiple myeloma (Shruhmer et al, Blood, 2005), neuroblastoma (Cattelani et al, CCR, 2008), Hodgkin lymphoma (Drakos et al, CCR, 2007), osteosarcoma and prostate cancer (Vassilev et al, Science, 2004), Kaposi's sarcoma (Sarek, J. Clinic, Invest., 2007), rhabdomyosarcoma (Miyachi et al, CCR, 2009), RCC (renal cell carcinoma) (Roberts et al, CR, 2009), squamous cell carcinoma and esophageal cancers (Cescon et al, CCR, 2009), cutaneous melanoma (Firoz et al, CCR, 2009), retinoblastoma (Laurie et al, Nature, 2006). There are evidences that pancreatic cancer with wild type p53 gene could be sensitive to MDM2 inhibitors as well (submitted for publication).

TABLE 1

Summary of MDM2 gene amplification frequencies from 28 human tumors (Momand et al, NAR, 1998).

| Tumor type | MDM2 amplification ($n^a$) (%) | References |
|---|---|---|
| Brain tumors | 6.7 (239) | 57-60 |
| Astrocytomas | 8.1 (37) | 57, 60 |
| Glioblastomas | 6.8 (191) | 57, 58, 60 |
| Medulloblastomas | 0 (8) | 59 |
| Other | 0 (3) | 60 |
| Breast carcinomas | 5.9 (1774) | 61-65 |
| Cervical carcinomas | 1.1 (88) | 19, 66 |
| Esophageal carcinomas | 13 (96) | 14, 67 |
| Leukemias/lymphomas | 0 (304) | 68-70 |
| Hepatoblastomas | 0 (38) | 71 |
| Lung | 5.7 (88) | 72-74 |
| Lung cancers (NSCLC) | 6.0 (83) | 72, 74 |
| Lung (not specified) | 0 (5) | 73 |
| Nasopharyngeal carcinomas | 2.1 (46) | 75 |
| Neuroblastoma | 2.0 (51) | 76-78 |
| Osteosarcomas | 16 (207) | 3, 79-82 |
| Ovarian carcinomas | 3.1 (190) | 64, 83 |
| Pancreatic carcinomas | 0 (25) | 84 |
| Soft tissue tumors | 20 (479) | 3, 36, 76, 79, 80, 85-90 |
| Ewing's sarcomas | 10 (30) | 85 |
| Leiomyosarcomas | 0 (46) | 79, 86, 88 |
| Lipomas (benign) | 30 (43) | 80, 86 |
| Liposarcomas | 29 (87) | 3, 79, 80, 87, 89 |

TABLE 1-continued

Summary of MDM2 gene amplification frequencies from 28 human tumors (Momand et al, NAR, 1998).

| Tumor type | MDM2 amplification ($n^a$) (%) | References |
|---|---|---|
| Malignant fibrous histiocytomas | 21 (163) | 3, 79, 80, 86, 90 |
| Malignant Schwannomas | 19 (16) | 79 |
| Sarcomas (non-specific)[b] | 13 (85) | 36, 76 |
| Various[c] | 33 (9) | 76, 79, 86 |
| Testicular tumors | 4.6 (64) | 91, 92 |
| Thyroid carcinomas | 0 (22) | 93 |
| Urothelial carcinomas | 2.2 (137) | 94, 95 |
| Wilms' tumors | 0 (40) | 76 |

Total number of tumor samples analyzed was 3889 and the average MDM2 gene amplification frequency was 7.2%.
[a]Number of samples analyzed.
[b]Sarcomas of soft tissue origin that were not specified.
[c]Soft tissue tumors that did not fall into the listed classes. The number of samples was less than five in any individual class.

Human MDMX gene maps in chromosomal region 1q32, which is frequently amplified in human cancers. It has been documented in 4% of gliomas (Riemenschneider, C R 1999) and 5% breast cancers (Danovi et al, MCB, 2004). Recently, ~60% of retinoblastomas (Laurie, Nature 2006) have been found to bear HDMX overexpression. Moreover, HDMX gene was found overexpressed in a large subset of cervical and ovarian cancer cell lines (Ramos, C R 2001). A systemic analysis of HDMX expression in primary tumors of different origins revealed broad spectrum of human cancers with HDMX overexpression

TABLE 1

Summary of HDMX gene amplification frequencies from 500 human tumors (Danovi et al, MCB, 2004).

| Tumor type | Total | HDMX overexpressed |
|---|---|---|
| Breast cancer | 218 | 41 |
| Colon cancer | 27 | 5 |
| Lung cancer | 88 | 16 |
| Prostate cancer | 25 | 0 |
| Stomach cancer | 14 | 6 |
| Testis cancer | 11 | 3 |
| Larynx cancer | 13 | 3 |
| Uterus cancer | 13 | 2 |
| Melanoma | 14 | 2 |
| Sarcoma | 10 | 0 |

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I), (Ia), (Ic), (Id), (Ie) or (If) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I), (Ia), (Ic), (Id), (Ie) or (If) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I), (Ia), (Ic), (Id), (Ie) or (If). Compounds of formula (I), (Ia), (Ic), (Id), (Ie) or (If) may be solvated, especially hydrated. The hydratization/hydration may occur during the process of production or as a consequence of the hygroscopic nature of the initially water free compounds of formula (I), (Ia), (Ic), (Id), (Ie) or (If). The solvates and/or hydrates may e.g. be present in solid or liquid form.

It should be appreciated that certain compounds of formula (I), (Ia), (Ic), (Id), (Ic) or (If) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I), (Ia), (Ic), (Id), (Ie) or (If) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

The therapeutic use of compounds according to formula (I), (Ia), (Ic), (Id), (Ie) or (If), their pharmacologically acceptable salts, solvates and hydrates, respectively, as well as formulations and pharmaceutical compositions also lie within the scope of the present invention.

The pharmaceutical compositions according to the present invention comprise at least one compound of formula (I), (Ia), (Ic), (Id), (Ie) or (If) as an active ingredient and, optionally, carrier substances and/or adjuvants.

The present invention also relates to pro-drugs which are composed of a compound of formula (I), (Ia), (Ic), (Id), (Ie) or (If) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), (Ia), (Ic), (Id), (Ie) or (If), carrying a hydroxy group (—OH): a sulfate, a phosphate (—$OPO_3$ or —$OCH_2OPO_3$) or an ester of an amino acid. Especially preferred are pro-drugs of the hydroxy group of a compound of formula (I), (Ia), (Ic), (Id), (Ie) or (If).

As mentioned above, therapeutically useful agents that contain compounds of formula (I), (Ia), (Ic), (Id), (Ie) or (If), their solvates, salts or formulations are also comprised in the scope of the present invention. In general, compounds of formula (I), (Ia), (Ic), (Id), (Ie) or (If) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdential, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The compounds of the present invention can be prepared according to the following procedure:

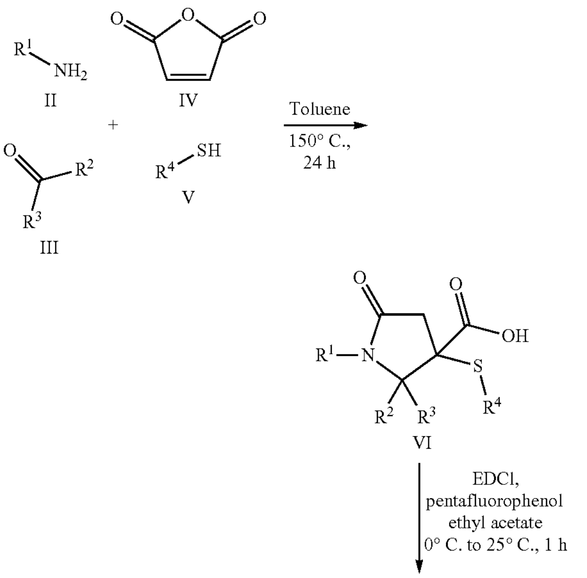

-continued

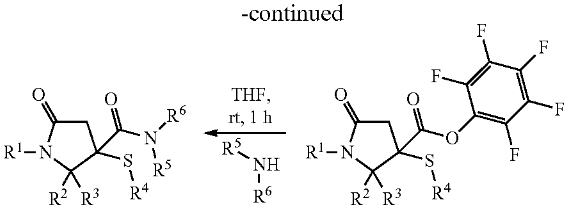

I VIII VII

The synthesis of the 4-sulfanyl-pyrrolidin-2-one scaffold is based on a four-component reaction (4CR) between a primary amine (H), an aldehyde or ketone (III) with maleic anhydride (IV), and a thiol (V). The reaction is preferably performed in toluene at reflux with a stoichiometric amount of the starting materials, according to J. Wei, J. T. Shaw *Org. Lett* 2007, 9, 4077. The resulting 4-sulfanyl-pyrrolidin-2-one (VI) is formed in acceptable to good yields as a diastereoisomeric mixture. Generally, the two diastereoisomers are separated and isolated by preparative HPLC-chromatography. The final 4-sulfanyl-pyrrolidin-2-one amide of formula (I), (Ia), (Ic), (Id), (Ie) or (10 was obtained via aminolysis using amine (VIII) of the corresponding pentafluorophenyl esters of formula (VII) that were synthesized according to M. Bodanszky, A. Bodanszky. The practice of Peptide Synthesis 2nd Edition, p 102, Springer-Verlag Berlin Heidelberg New York (1994). These compounds of formula (I), (Ia), (Ic), (Id), (Ie) or (If) can be further modified such as the conversion into esters or salts from acids, salts from amines or by cleaving off protecting groups found in substituents $R^1$ to $R^6$.

Further compounds of formula (I) wherein n is 0 can be prepared following the procedures described in:

1) M. R, Linder, J. Podlech, Organic Letters 2001, Vol. 3, No. 12, 1849-1851;

2) J. Podlech, M. R. Linder, J. Org. Chem. 1997, 62, 5873-5883;

3) J. Cesar, M. Soliner Dolene, Tetrahedron Letters 42 (2001) 7099-7102.

The reaction procedures described herein may also be carried out in the presence of a chiral catalyst like e.g. proline-derived catalysts (as e.g. described in www.organic-chemistry.org/Highlights/2007/25March.shtm) in order to obtain the corresponding enantiomerically pure compounds.

EXAMPLES

The present invention encompasses the following Examples:

Example 1

General Procedure for the Synthesis of 5-oxo-3-sulfanyl-pyrrolidin-3-carboxamides (I)

Maleic anhydride (IV, 1 mmol), a thiol (V, 1 mmol), aldehyde or ketone (III, 1 mmol) and amine (II, 1 mmol) in toluene (8 mL) were heated to 150° C. in a sealed tube for 24 hours, After cooled to room temperature, the solution was concentrated in vacuo. Purification on silica gel using an eluent (ethyl acetate: methanol=9:1 to 1:1) yielded compounds of formula (VI) as a diastereoisomeric mixture. Afterwards, the two diastereoisomers were separated by preparative HPLC chromatography. Preparative separations were usually performed with an acetonitrile-water eluent (+0.1% formic acid) on a RP Polaris C18 column (length: 250 mm, diameter: 21 mm; particle size: 5 μm). Generally, good separations were observed (retention times of the two cis/trans diasteroisomers differed by 1 to 2 minutes) by using isocratic systems (70% acetonitrile: 30% water).

To a suspension of 1-(3-dimethylaminopropyl)-3-ethylcarbodiimide hydrochloride EDCI (1.5 mmol) in 8 mL ethyl acetate was added pentafluorophenol (3 mmol) at 0° C.

After 10 minutes, 5-oxo-pyrrolidine-3-carboxylic acid VI (1 mmol) was added at 0° C. and the reaction mixture was stirred for 1 hour at room temperature. After evaporation of the solvent, the crude product was purified by chromatography on silica gel (ethyl acetate:hexane=1:2) to yield the corresponding 5-oxo-pyrrolidine-3-carboxylic acid pentafluorophenyl ester VII as a colourless oil.

To a suspension of 5-oxo-pyrrolidine-3-carboxylic acid pentafluorophenyl ester VII (0.5 mmol) in 2 mL dry THF was added the desired amine VIII (0.5 mmol) at room temperature. The reaction mixture was stirred for 1 hour at room temperature. Afterwards, 20 mL methylene chloride were added. The resulting organic layer was washed with 20 mL of a saturated aqueous solution of sodium hydrogencarbonate, dried over magnesium sulfate and the solvent was removed in vacuo. Finally, the crude product was purified by chromatography on silica gel with a suitable eluent to afford the desired 5-oxo-pyrrolidine-3-carboxamide I as a white solid.

Example 2

According to the general procedure in example 1, the following compounds were prepared:

2.1 cis-2-(6-chloro-1-methyl-1H-indol-3-yl)-1-[(4-chlorophenyl)methyl]-3-[(4-methylphenyl)sulfanyl]-5-oxo-N-(pyridin-2-ylmethyl)pyrrolidine-3-carboxamide. Molecular Formula=C34H30Cl2N4O2S. Molecular Weight=629.599. $[M+H]^+$ observed=629.1. Isolated yield 34.08%.

2.2 trans-2-(6-chloro-1-methyl-1H-indol-3-yl)-1-[(4-chlorophenyl)methyl]-3-[(4-methylphenyl)sulfanyl]-5-oxo-N-(pyridin-2-ylmethyl)pyrrolidine-3-carboxamide, Molecular Formula=C34H30Cl2N4O2S. Molecular Weight=629.599, $[M+H]^+$ observed=629.1. Isolated yield 3.78%.

2.3 trans-2-(6-chloro-1-methyl-1H-indol-3-yl)-1-[(4-chlorophenyl)methyl]-3-[(4-methylphenyl)sulfanyl]-5-oxo-N-(thiophen-2-ylmethyl)pyrrolidine-3-carboxamide. Molecular Formula=C33H29Cl2N3O2S2. Molecular Weight=634.638. $[M+H]^+$ observed=656.0. Isolated yield 3.04%.

2.4 cis-2-(6-chloro-1-methyl-1H-indol-3-yl)-1-[(4-chlorophenyl)methyl]-3-[(4-methylphenyl)sulfanyl]-5-oxo-N-(thiophen-2-ylmethyl)pyrrolidine-3-carboxamide. Molecular Formula=C33H29Cl2N3O2S2, Molecular Weight=634.638. $[M+Na]^+$ observed=656.0. Isolated yield 27.34%.

2.5 trans-2-(6-chloro-1-methyl-1H-indol-3-yl)-1-(4-chlorophenyl)-3-[(4-methylphenyl)sulfanyl]-5-oxo-N-(pyridin-2-ylmethyl)pyrrolidine-3-carboxamide. Molecular Formula=C33H28Cl2N4O2S, Molecular Weight=615.572. $[M+H]^+$ observed=615.1. Isolated yield 2.78%.

2.6 cis-2-(6-chloro-1-methyl-1H-indol-3-yl)-1-(4-chlorophenyl)-3-[(4-methylphenyl)sulfanyl]-5-oxo-N-(pyridin-2-ylmethyl)pyrrolidine-3-carboxamide. Molecular Formula=C33H28Cl2N4O2S. Molecular Weight=615.572, $[M+H]^+$ observed=615.1. Isolated yield 25.06%.

2.7 cis-2-(6-chloro-1H-indol-3-yl)-1-[(4-chlorophenyl)methyl]-3-[(4-methylphenyl)sulfanyl]-5-oxo-N-(pyridin-2- ylmethyl)pyrrolidine-3-carboxamide. Molecular Formula=C33H28Cl2N4O2S. Molecular Weight=615.572. $[M+H]^+$ observed=615.2. Isolated yield 12.50%.

2.8 trans-2-(6-chloro-1H-indol-3-yl)-1-[(4-chlorophenyl) methyl]-3-[(4-methylphenyl)sulfanyl]-5-oxo-N-(pyridin-2-ylmethyl)pyrrolidine-3-carboxamide. Molecular Formula=C33H28Cl2N4O2S, Molecular Weight=615.572. $[M+H]^+$ observed=615.2, Isolated yield 4.56%.

2.9 trans-2-(6-chloro-1H-indol-3-yl)-1-[(4-chlorophenyl) methyl]-N-[3-(morpholin-4-yl)propyl]-5-oxo-3-(phenylsulfanyl)pyrrolidine-3-carboxamide. Molecular Formula=C33H34Cl2N4O3S. Molecular Weight=637.619. $[M+H]^+$ observed=637.2. Isolated yield 7.30%.

2.10 cis-2-(6-chloro-1H-indol-3-yl)-1-[(4-chlorophenyl)methyl]-N-[3-(morpholin-4-yl)propyl]-5-oxo-3-(phenylsulfanyl)pyrrolidine-3-carboxamide. Molecular Formula=C33H34Cl2N4O3S. Molecular Weight=637.619. $[M+H]^+$ observed=637.2. Isolated yield 7.18%.

2.11 trans-2-(6-chloro-1H-indol-3-yl)-1-[(4-chloro-2-methylphenyl)methyl]-N-[3-(morpholin-4-yl)propyl]-5-oxo-3-(phenylsulfanyl)pyrrolidine-3-carboxamide, Molecular Formula=C34H36O2N4O3S. Molecular Weight=651.646. $[M+H]^+$ observed=651.2. Isolated yield 5.18%.

2.12 cis-2-(6-chloro-1H-indol-3-yl)-1-[(4-chloro-2-methylphenyl)methyl]-N-[3-(morpholin-4-yl)propyl]-5-oxo-3-(phenylsulfanyl)pyrrolidine-3-carboxamide. Molecular Formula=C34H36Cl2N4O3S. Molecular Weight=651.646. $[M+H]^+$ observed=651.2. Isolated yield 7.74%.

2.13 trans-2-(6-chloro-1H-indol-3-yl)-1-[(3-chlorophenyl) methyl]-N-[3-(morpholin-4-yl)propyl]-5-oxo-3-(phenylsulfanyl)pyrrolidine-3-carboxamide. Molecular Formula=C33H34Cl2N4O3S. Molecular Weight=637.619. $[M+H]^+$ observed=637.2. Isolated yield 2.82%.

2.14 cis-2-(6-chloro-1H-indol-3-yl)-1-[(3-chlorophenyl)methyl]-N-[3-(morpholin-4-yl)propyl]-5-oxo-3-(phenylsulfanyl)pyrrolidine-3-carboxamide. Molecular Formula=C33H34Cl2N4O3S. Molecular Weight 637.619. $[M+H]^+$ observed=637.2. Isolated yield 3.81%.

2.15 trans-2-(6-chloro-1H-indol-3-yl)-1-[(1R)-1-(4-chlorophenyl)ethyl]-N-[3-(morpholin-4-yl)propyl]-5-oxo-3-(phenylsulfanyl)pyrrolidine-3-carboxamide. Molecular Formula $C34H_{36}Cl_2N4O3S$, Molecular Weight=651.646. $[M+H]^+$ observed=651.2. Isolated yield 2.65%.

2.16 cis-2-(6-chloro-1H-indol-3-yl)-1-[(1R)-1-(4-chlorophenyl)ethyl]-N-[3-(morpholin-4-yl)propyl]-5-oxo-3-(phenylsulfanyl)pyrrolidine-3-carboxamide. Molecular Formula=C34H36Cl2N4O3S. Molecular Weight=651.646. $[M+H]^+$ observed=651.2. Isolated yield 1.36%.

2.17 trans-2-(6-chloro-1H-indol-3-yl)-1-[(4-chlorophenyl) triethyl]-3-[(4-chlorophenyl)sulfanyl]-N-[3-(morpholin-4-yl)propyl]-5-oxopyrrolidine-3-carboxamide. Molecular Formula=C33H33Cl3N4O3S. Molecular Weight=672.064. $[M+H]^+$ observed=671.1. Isolated yield 6.65%.

2.18 cis-2-(6-chloro-1H-indol-3-yl)-1-[(4-chlorophenyl)methyl]-3-[(4-chlorophenyl)sulfanyl]-N-[3-(morpholin-4-yl) propyl]-5-oxopyrrolidine-3-carboxamide. Molecular Formula=$C33H_{33}Cl_3N4O3S$. Molecular Weight=672.064. $[M+H]^+$ observed=673.1. Isolated yield 19.04%.

2.19 trans-1-benzyl-2-(6-chloro-1H-indol-3-yl)-N-[3-(morpholin-4-yl)propyl]-5-oxo-3-(phenylsulfanyl)pyrrolidine-3-carboxamide. Molecular Formula=C33H35ClN4O3S. Molecular Weight=603.174. $[M+H]^+$ observed=603.0, Isolated yield 4.31%.

2.20 cis-1-benzyl-2-(6-chloro-1H-indol-3-yl)-N-[3-(morpholin-4-yl)propyl]-5-oxo-3-(phenylsulfanyl)pyrrolidine-3-carboxamide. Molecular Formula=C33H35ClN4O3S. Molecular Weight=603.174. $[M+H]^+$ observed=603.0. Isolated yield 4.59%.

2.21 trans-2-(6-chloro-1H-indol-3-yl)-1-[(1S)-1-(4-chlorophenyl)ethyl]-N-[3-(morpholin-4-yl)propyl]-5-oxo-3-(phenylsulfanyl)pyrrolidine-3-carboxamide. Molecular Formula=C34H36Cl2N4O3S. Molecular Weight=651.646. $[M+H]^+$ observed=650.9. Isolated yield 4.91%.

2.22 cis-2-(6-chloro-1H-indol-3-yl)-1-[(1S)-1-(4-chlorophenyl)ethyl]-N-[3-(morpholin-4-yl)propyl]-5-oxo-3-(phenylsulfanyl)pyrrolidine-3-carboxamide. Molecular Formula=C34H36Cl2N4O3S. Molecular Weight=651.646. $[M+H]^+$ observed=651.0. Isolated yield 4.86%.

2.23 trans-2-(6-bromo-1H-indol-3-yl)-1-[(4-chlorophenyl) methyl]-3-[(4-methylphenyl)sulfanyl]-N-[3-(morpholin-4-yl)propyl]-5-oxopyrrolidine-3-carboxamide. Molecular Formula=$C_{34}H_{36}BrClN4O3S$. Molecular Weight=696.097. $[M+H]^+$ observed=697.1. Isolated yield 9.27%.

2.24 cis-2-(6-bromo-1H-indol-3-yl)-1-[(4-chlorophenyl)methyl]-3-[(4-methylphenyl)sulfanyl]-N-[3-(morpholin-4-yl)propyl]-5-oxopyrrolidine-3-carboxamide. Molecular Formula=C34H36BrClN4O3S. Molecular Weight=696.097. $[M+H]^+$ observed=697.0. Isolated yield 11.14%.

2.25 trans-2-(5-bromo-1H-indol-3-yl)-1-[(4-chlorophenyl) methyl]-N-[3-(morpholin-4-yl)propyl]-5-oxo-3-(phenylsulfanyl)pyrrolidine-3-carboxamide. Molecular Formula=C33H34BrClN4O3S. Molecular Weight=682.07. $[M+H]^+$ observed 682.9. Isolated yield 3.71%.

2.26 cis-2-(5-bromo-1H-indol-3-yl)-1-[(4-chlorophenyl)methyl]-N-[3-(morpholin-4-yl)propyl]-5-oxo-3-(phenylsulfanyl)pyrrolidine-3-carboxamide. Molecular Formula=C33H34BrClN4O3S, Molecular Weight=682.07. $[M+H]^+$ observed=682.8. Isolated yield 4.65%.

2.27 cis-2-(6-chloro-1H-indol-3-yl)-1-[(6-chloropyridin-3-yl)methyl]-N-[3-(morpholin-4-yl)propyl]-5-oxo-3-(phenylsulfanyl)pyrrolidine-3-carboxamide. Molecular Formula=C32H33Cl2N5O3S. Molecular Weight=638.607, $[M+H]^+$ observed=638.0. Isolated yield 3.76%.

2.28 trans-2-(6-chloro-1H-indol-3-yl)-1-[(6-chloropyridin-3-yl)methyl]-N-[3-(morpholin-4-yl)propyl]-5-oxo-3-(phenylsulfanyl)pyrrolidine-3-carboxamide. Molecular Formula C32H33Cl2N5O3S. Molecular Weight=638.607. Isolated yield 2.29 trans-4-{[2-(6-chloro-1H-indol-3-yl)-1-[(1S)-1-(4-chlorophenyl)ethyl]-5-oxo-3-(phenylsulfanyl)pyrrolidin-3-yl]carbonyl}piperazin-2-one. Molecular Formula=C31H28Cl2N4O3S. Molecular Weight=607.55. $[M+H]^+$ observed=607.2. Isolated yield 4.44%.

2.30 cis-4-{[2-(6-chloro-1H-indol-3-yl)-1-[(1S)-1-(4-chlorophenyl)ethyl]-5-oxo-3-(phenylsulfanyl)pyrrolidin-3-yl] carbonyl}piperazin-2-one. Molecular Formula=C31H28Cl2N4O3S, Molecular Weight=607.55. $[M+H]^+$ observed=607.2. Isolated yield 4.09%.

2.31 trans-4-{[2-(6-chloro-1H-indol-3-yl)-1-[(1R)-1-(4-chlorophenyl)ethyl]-5-oxo-3-(phenylsulfanyl)pyrrolidin-3-yl]carbonyl}piperazin-2-one. Molecular Formula=C31H28Cl2N4O3S. Molecular Weight=607.55. $[M+H]^+$ observed=608.8. Isolated yield 2.62%.

2.32 cis-4-{[2-(6-chloro-1H-indol-3-yl)-1-[(1R)-1-(4-chlorophenyl)ethyl]-5-oxo-3-(phenylsulfanyl)pyrrolidin-3-yl]carbonyl}piperazin-2-one. Molecular Formula=C33H34ClFN4O3S. Molecular Weight=607.55. $[M+H]^+$ observed=606.9. Isolated yield 1.89%.

2.33 trans-1-[(4-chlorophenyl)methyl]-2-(6-fluoro-1H-indol-3-yl)-N-[3-(morpholin-4-yl)propyl]-5-oxo-3-(phenylsulfanyl)pyrrolidine-3-carboxamide. Molecular Formula=$C_{33}H_{34}ClFN_4O_3S$. Molecular Weight=621.164. $[M+H]^+$observed=621.0. Isolated yield 2.98%.

2.34 cis-1-[(4-chlorophenyl)methyl]-2-(6-fluoro-1H-indol-3-yl)-N-[3-(morpholin-4-yl)propyl]-5-oxo-3-(phenylsulfanyl)pyrrolidine-3-carboxamide. Molecular Formula=$C_{33}H_{34}ClFN_4O_3S$. Molecular Weight=621.164. $[M+H]^+$ observed=621.0, Isolated yield 4.72%.

2.35 cis-4-{[2-(6-bromo-1H-indol-3-yl)-1-[(4-chlorophenyl)methyl]-3-[(4-methylphenyl)sulfanyl]-5-oxopyrrolidin-3-yl]carbonyl}piperazin-2-one. Molecular Formula=C31H28BrClN4O3S. Molecular Weight=652.001. $[M+H]^+$ observed=651.3. Isolated yield 8.00%.

2.36 cis-1-[(4-bromophenyl)methyl]-2-(6-chloro-1H-indol-3-yl)-3-[(4-methylphenyl)sulfanyl]-N-[3-(morpholin-4-yl)propyl]-5-oxopyrrolidine-3-carboxamide. Molecular Formula=C34H36BrClN4O3S. Molecular Weight=696.097. $[M+H]^+$ observed=697.2. Isolated yield 8.39%.

2.37 trans-1-[(4-bromophenyl)methyl]-2-(6-chloro-1H-indol-3-yl)-3-[(4-methylphenyl)sulfanyl]-N-[3-(morpholin-4-yl)propyl]-5-oxopyrrolidine-3-carboxamide. Molecular Formula=C34H36BrClN4O3S. Molecular Weight=696.097. $[M+H]^+$ observed=697.1. Isolated yield 3.45%.

2.38 cis-2-(6-bromo-1H-indol-3-yl)-1-[(4-bromophenyl)methyl]-3-[(4-methylphenyl)sulfanyl]-N-[3-(morpholin-4-yl)propyl]-5-oxopyrrolidine-3-carboxamide. Molecular Formula=C34H36Br2N4O3S. Molecular Weight=740.548. $[M+H]^+$ observed=740.5. Isolated yield 10.00%.

2.39 cis-2-(6-chloro-1H-indol-3-yl)-1-[(4-chloro-3-fluorophenyl)methyl]-3-[(4-methylphenyl)sulfanyl]-N-[3-(morpholin-4-yl)propyl]-5-oxopyrrolidine-3-carboxamide. Molecular Formula=C34H35Cl2FN4O3S. Molecular Weight=669.636. $[M+H]^+$ observed=669.1. Isolated yield 14.85%.

2.40 trans-2-(6-chloro-1H-indol-3-yl)-1-[(4-chloro-3-fluorophenyl)methyl]-3-[(4-methylphenyl)sulfanyl]-N-[3-(morpholin-4-yl)propyl]-5-oxopyrrolidine-3-carboxamide. Molecular Formula=C34H35Cl2FN4O3S. Molecular Weight=669.636. $[M+H]^+$ observed=669.0. Isolated yield 4.48%.

2.41 cis-2-(6-chloro-5-fluoro-1H-indol-3-yl)-1-[(4-chlorophenyl)methyl]-3-[(4-methylphenyl)sulfanyl]-N-[3-(morpholin-4-yl)propyl]-5-oxopyrrolidine-3-carboxamide. Molecular Formula=C34H35Cl2FN4O3S. Molecular Weight=669.636. $[M+H]^+$ observed=669.1. Isolated yield 4.88%.

2.42 trans-2-(6-chloro-5-fluoro-1H-indol-3-yl)-1-[(4-chlorophenyl)methyl]-3-[(4-methylphenyl)sulfanyl]-N-[3-(morpholin-4-yl)propyl]-5-oxopyrrolidine-3-carboxamide. Molecular Formula=C34H35Cl2FN4O3S. Molecular Weight=669.636. $[M+H]^+$ observed=669.1. Isolated yield 1.08%.

2.43 cis-5-(6-chloro-1H-indol-3-yl)-1-[(4-chlorophenyl)methyl]-4-{[4-(2-hydroxyethyl)piperazin-1-yl]carbonyl}-4-[(4-methylphenyl)sulfanyl]pyrrolidin-2-one. Molecular Formula=C33H34Cl2N4O3S. Molecular Weight=637.619. $[M+H]^+$ observed=637.0. Isolated yield 7.67%.

2.44 cis-2-(6-chloro-1H-indazol-3-yl)-1-[(4-chlorophenyl)methyl]-3-[(4-methylphenyl)sulfanyl]-N-[3-(morpholin-4-yl)propyl]-5-oxopyrrolidine-3-carboxamide. Molecular Formula C33H35Cl2N5O3S. Molecular Weight=652.634. $[M+H]^+$ observed=652.0. Isolated yield 6.04%.

2.45 cis-2-(6-chloro-1H-indol-3-yl)-1-[(4-chlorophenyl)methyl]-3-[(4-methylphenyl)sulfanyl]-[3-(morpholin-4-yl)propyl]-5-oxopyrrolidine-3-carboxamide. Molecular Formula=C34H36Cl2N4O3S. Molecular Weight=651.646, $[M+H]^+$ observed=651.1. Isolated yield 7.97%.

2.46 cis-1-[(4-bromophenyl)methyl]-5-(6-chloro-1H-indol-3-yl)-4-{[4-(2-hydroxyethyl)piperazin-1-yl]carbonyl}-4-[(4-methylphenyl)sulfanyl]pyrrolidin-2-one. Molecular Formula=C33H34BrClN4O3S. Molecular Weight=682.07, $[M+H]^+$ observed=683.0. Isolated yield 5.35%.

2.47 cis-1-[(4-bromophenyl)methyl]-2-(6-chloro-1H-indol-3-yl)-N-(2,3-dihydroxypropyl)-3-[(4-methylphenyl)sulfanyl]-5-oxopyrrolidine-3-carboxamide. Molecular Formula=C30H29BrClN3O4S, Molecular Weight ~642.991. $[M+Na]^+$ observed=668.1. Isolated yield 6.92%.

2.48 cis-4-{[1-[(4-bromophenyl)methyl]-2-(6-chloro-1H-indol-3-yl)-3-[(4-methylphenyl)sulfanyl]-5-oxopyrrolidin-3-yl]carbonyl}piperazin-2-one. Molecular Formula=C31H28BrClN4O3S. Molecular Weight=652.001. $[M+H]^+$ observed=653.1. $[M+Na]^+$ observed=675.3. Isolated yield 3.39%.

2.49 cis-1-[(4-bromophenyl)methyl]-2-(6-chloro-1H-indol-3-yl)-3-[(4-methylphenyl)sulfanyl]-N-[2-(morpholin-4-yl)ethyl]-5-oxopyrrolidine-3-carboxamide, Molecular Formula=$C_{33}H_{34}BrClN_4O_3S$. Molecular Weight=682.07. $[M+H]^+$ observed=683.1. Isolated yield 7.30%.

2.50 cis-1-[(4-bromophenyl)methyl]-2-(6-chloro-1H-indol-3-yl)-3-[(4-methylphenyl)sulfanyl]-N-[4-(morpholin-4-yl)butyl]-5-oxopyrrolidine-3-carboxamide. Molecular Formula=C35H38BrClN4O3S. Molecular Weight=710.123. $[M+H]^+$ observed=711.0. Isolated yield 7.08%.

2.50 cis-1-[(4-bromophenyl)methyl]-2-(6-chloro-1H-indol-3-yl)-N-(4-hydroxybutyl)-3-[(4-methylphenyl)sulfanyl]-5-oxopyrrolidine-3-carboxamide. Molecular Formula=C31H31BrClN3O3S. Molecular Weight=641.018. $[M+Na]^+$observed=664.2. Isolated yield 7.32%.

2.51 cis-1-[(4-bromophenyl)methyl]-2-(6-chloro-1H-indol-3-yl)-3-[(4-methylphenyl)sulfanyl]-N-(1-methylpiperidin-4-yl)-5-oxopyrrolidine-3-carboxamide. Molecular Formula=$C33H34BrClN4O_2S$. Molecular Weight=666.071. $[M+H]^+$ observed=668.2. Isolated yield 7.51%.

2.52 cis-1-[(4-bromophenyl)methyl]-2-(6-chloro-1H-indol-3-yl)-3-[(4-ethylphenyl)sulfanyl]-N-[3-(morpholin-4-yl)propyl]-5-oxopyrrolidine-3-carboxamide. Molecular Formula=C35H38BrClN4O3S. Molecular Weight=710.123. [M+H]$^+$ observed=711.1. Isolated yield 17.16%.

2.53 cis-1-[(4-bromophenyl)methyl]-2-(6-chloro-1H-indol-3-yl)-3-[(3,4-dimethylphenyl)sulfanyl]-N-[3-(morpholin-4-yl)propyl]-5-oxopyrrolidine-3-carboxamide. Molecular Formula=C35H38BrClN4O3S. Molecular Weight=710.123. [M+H]$^+$observed=711.0. Isolated yield 9.74%.

2.52 cis-1-[(4-bromophenyl)methyl]-2-(6-chloro-1H-indol-3-yl)-3-[(2,4-dimethylphenyl)sulfanyl]-N-[3-(morpholin-4-yl)propyl]-5-oxopyrrolidine-3-carboxamide. Molecular Formula=C35H38BrClN4O3S. Molecular Weight=710.123. [M+H]$^+$ observed=711.0. Isolated yield 6.38%.

2.53 trans-1-[(4-bromophenyl)methyl]-2-(6-chloro-1H-indol-3-yl)-N-[3-(morpholin-4-yl)propyl]-3-[(4-nitrophenyl)sulfanyl]-5-oxopyrrolidine-3-carboxamide. Molecular Formula=C33H33BrClN5O5S. Molecular Weight=727.068. [M+H]$^+$observed=726.0. Isolated yield 3.00%.

2.54 cis-1-[(4-bromophenyl)methyl]-2-(6-chloro-1H-indol-3-yl)-N-[3-(morpholin-4-yl)propyl]-3-[(4-nitrophenyl)sulfanyl]-5-oxopyrrolidine-3-carboxamide. Molecular Formula=C33H33BrClN5O5S. Molecular Weight=727.068. [M+H]$^+$ observed 727.9. Isolated yield 0.41%.

2.55 cis-1-[(4-bromophenyl)methyl]-2-(6-chloro-1H-indol-3-yl)-N-[(2R)-1-hydroxypropan-2-yl]-3-[(4-methylphenyl)sulfanyl]-5-oxopyrrolidine-3-carboxamide. Molecular Formula=C30H29BrClN3O3S. Molecular Weight=626.992. [M+Na]$^+$ observed=650.2. Isolated yield 8.04%.

2.56 cis-1-[(4-bromophenyl)methyl]-2-(6-chloro-1H-indol-3-yl)-N-[(2S)-1-hydroxypropan-2-yl]-3-[(4-methylphenyl)sulfanyl]-5-oxopyrrolidine-3-carboxamide. Molecular Formula=C30H29BrClN3O3S. Molecular Weight=626.992. [M+Na]$^+$ observed=650.2, Isolated yield 8.04%.

Example 3

1) Synthesis of 4-[5-oxo-pyrrolidine-3-carbonyl]-piperazine-1-carboxylic Acid Ethylamide Compounds

Synthesis of (cis)-4-[1-(4-Bromo-benzyl)-2-(6-chloro-1H-indol-3-yl)-5-oxo-3-p-tolylsulfanyl-pyrrolidine-3-carbonyl]-piperazine-1-carboxylic acid ethylamide [PXN727-d1]

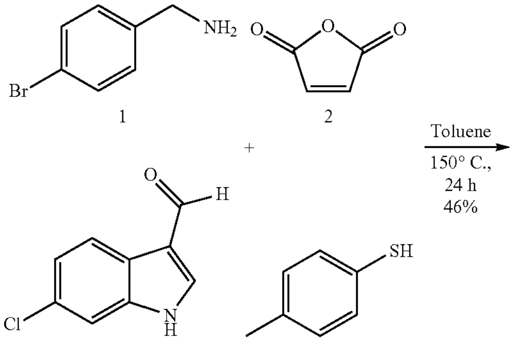

1 2 + 3 4

-continued

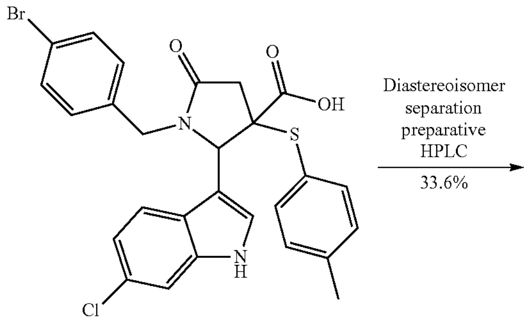

5
d1 (50%)/d2(50%)

d1 (cis)

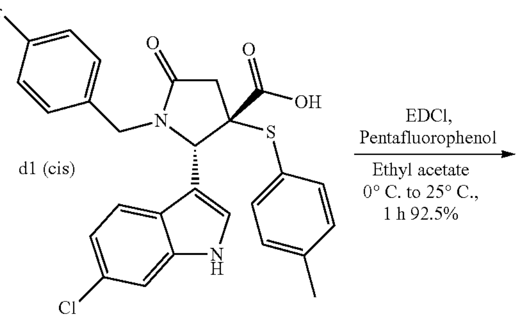

6

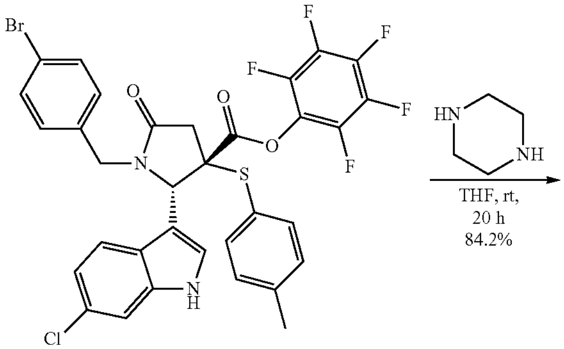

7

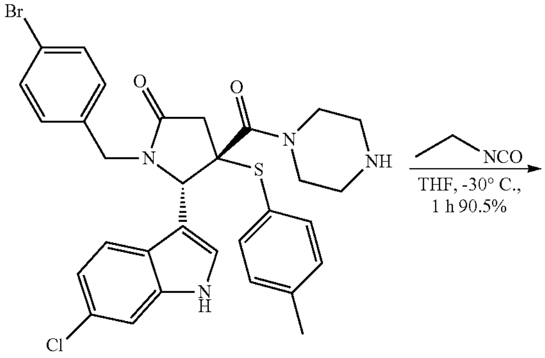

8

-continued

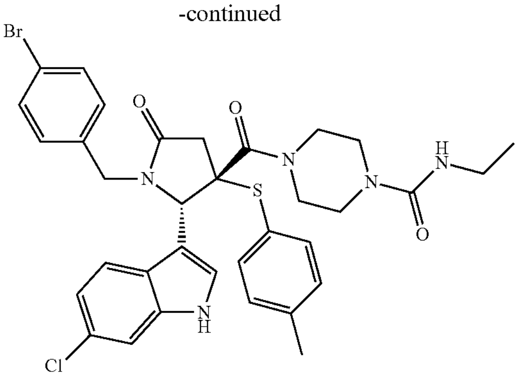

PXN 727-d1

Multicomponent Reaction (Step 1):

Maleic anhydride 2 (6 mmol), thiol 4 (6 mmol), aldehyde 3 (6 mmol) and amine 1 (6 mmol) in toluene (50 mL) were heated to 150° C. under Dean-Stark conditions for 24 hours. After being cooled to room temperature, the solution was concentrated in vacuo. Purification on silica gel (ethyl acetate:methanol=9:1 to 1:1) yielded 5 as a diastereoisomeric mixture (1.48 g, 46%).

Literature: J. Wei, J, T. Shaw *Org. Lett.* 2007, 9, 4077.

Separation of the Diastereoisomeric Mixture:

The above described reaction sequence yielded two diastereoisomers d1 and d2 in a 50:50 ratio. They were separated by preparative HPLC chromatography using the following conditions:

Column RP Polaris C18 (length: 250 mm, Ø: 21 mm; particle size: 5 μm).

Isocratic elution (70% acetonitrile: 30% water, 0.1% HCOOH), 21 mL/min, Rt=7.62 min.

The separation can also be performed with methanol/water mixtures.

Concentration of the solution in vacuo yielded the desired pure diastereoisomer 6 (cis, d1) as a light yellow solid (528.9 mg, 33.6%).

Overall yield for the preparation of 6: 15.47% (MCR and isolation of the cis-isomer d1)

Pentafluorophenyl Ester Formation:

To a suspension of 1-(3-dimethylaminopropyl)-3-ethylcarbodiimide hydrochloride EDCI (267 mg, 1.4 mmol) in 8 mL ethyl acetate was added pentafluorophenol (512 mg, 2.8 mmol) at 0° C. After 10 minutes, compound 6 (528.9 mg, 0.9 mmol) was added at 0° C. and the reaction mixture was stirred for 1 hour at room temperature. After evaporation of the solvent, the crude product was purified by chromatography on silica gel (ethyl acetate:hexane=1:2→1:1) to yield the corresponding pentafluorophenyl ester 7 as a colourless oil (632.0 mg, 92.5%).

Literature:

M. Bodanszky, A. Bodanszky, The practice of Peptide Synthesis 2nd Edition, p 102, Springer-Verlag Berlin Heidelberg New York (1994).

Amide Coupling:

To a suspension of pentafluorophenyl ester 7 (1.3 g, 1.8 mmol) in 16 mL dry THF was added piperazine (7.2 mmol) at room temperature. The reaction mixture was stirred for 20 hours at room temperature. Afterwards, 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was purified by chromatography on silica gel (ethyl acetate:methanol 9:1→1:1) to afford the desired piperazine amide 8 as a white solid (977.8 mg, 84.20%).

Reaction with Ethyl Isocyanate:

To a solution of compound 8 (848.3 mg, 1.3 mmol) in 15 mL THF extra dry was added ethyl isocyanate (283.6 mg, 4 mmol) at −30° C. After 1 h of stirring at −30° C., 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was purified by chromatography on silica gel with the system ethyl acetate:methanol 19:1 to yield PXY727-d1 as a white solid (853.4 mg, 90.5%).

mp=263.7-267.2° C.

$^1$H-NMR (400 MHz, DMSO) δ 11.57 (s, 1H), 7.57 (s, 1H), 7.50 (s, 1H), 7.44 (d, 2H, J=6.70 Hz), 7.25 (d, 1H, J=7.39 Hz), 7.09 (m, 5H), 6.90 (d, 2H, J=7.39 Hz), 6.53 (s, 1H), 4.93 (s, 1H), 4.74 (d, 1H, J=15.29 Hz), 3.84 (s, 2H), 3.60-3.20 (m, 4H), 3.45 (d, 1H, J=15.29), 3.15-2.80 (m, 4H), 3.09-3.06 (m, 2H), 2.25 (s, 3H), 1.03 (t, 3H, J=7.05 Hz).

IR: 3397, 3174, 2923, 1674, 1625, 1535, 1487, 1401, 1361, 1241, 1174, 1118, 1002, 794.

MS (+ESI): m/z=709.9 [M+1-1], 730.2 [M+Na].

Overall yield (four preparative steps and diastereoisomer separation): 10.91%

Example 4

2 Replacement of the Sulfur S (Group X) by Methylene $CH_2$

Synthesis of (cis)4-[3-Benzyl-1-(4-chloro-3-fluoro-benzyl)-2-(6-chloro-1H-indol-3-yl)-5-oxo-pyrrolidine-3-carbonyl]-piperazine-1-carboxylic acid ethylamide [PXN790-d1]

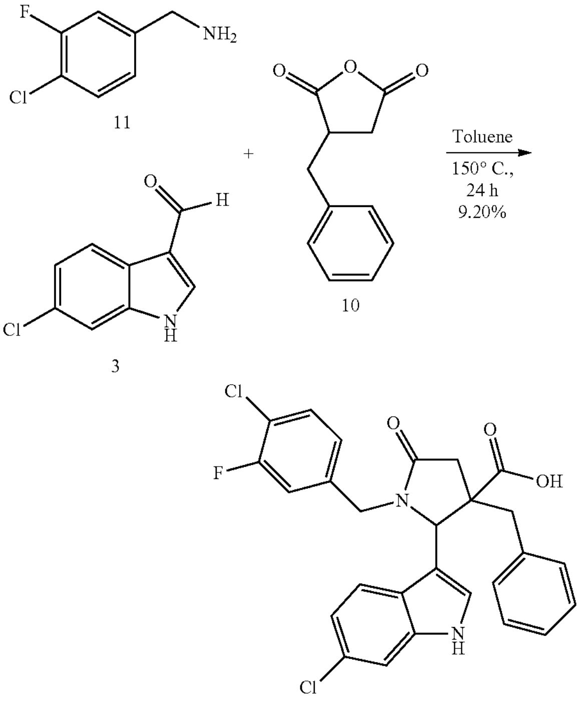

11

3

10

12

-continued

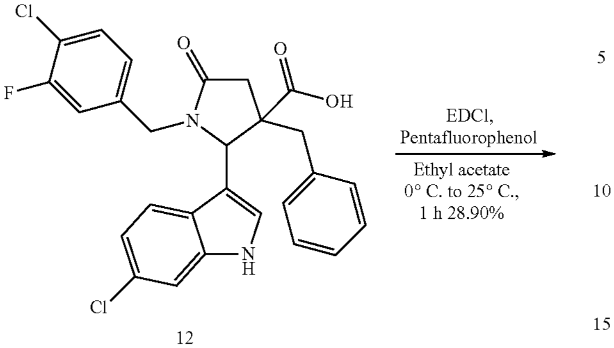

12

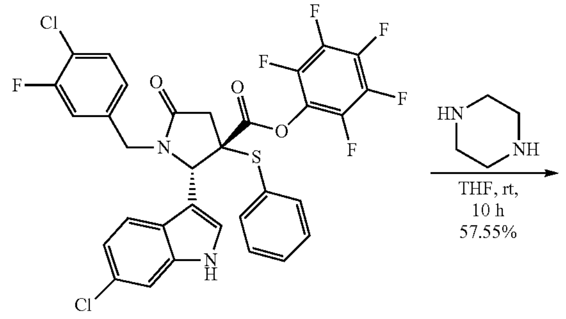

13

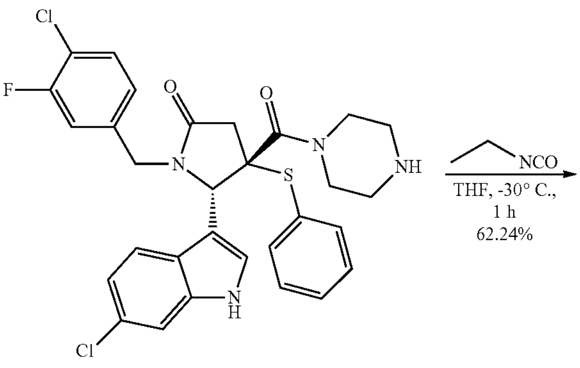

14

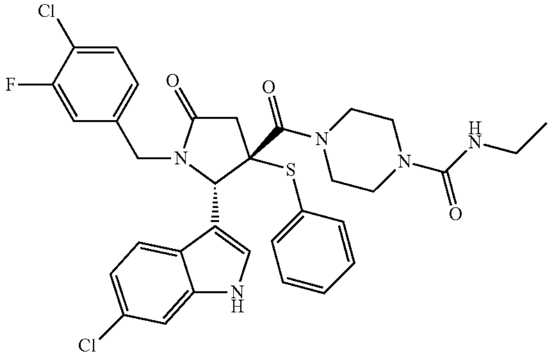

PXN 790-d1

Synthesis of alpha-benzylsuccinic anhydride 10

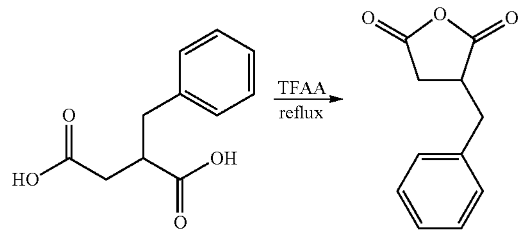

9 10

The commercially available alpha-benzylsuccinic acid 9 (1 g, 4.8 mmol) was refluxed for 1 h in 30 mL trifluoroacetic anhydride. Afterwards, the solvent was removed in vacuo. The crude residue was washed with cold hexane to yield alpha-benzylsuccinic anhydride 10 as a white solid (858.2 mg, 93.95%), Multicomponent Reaction Alpha-benzylsuccinic anhydride 10 (850 mg, 4.5 mmol), aldehyde 3 (1 mmol) and amine 11 (1 mmol) in toluene (16 mL) were heated to 150° C. in a sealed tube for 24 hours. After cooled to room temperature, the solution was concentrated in vacuo. Purification on silica gel (ethyl acetate: methanol=9:1 to 1:1) yielded MCR-product 12 as a diastereoisomeric mixture (210.3 mg, 9.20%).

Pentafluorophenyl Ester Formation

To a suspension of 1-(3-dimethylaminopropyl)-3-ethylcarbodiimide hydrochloride EACI (118.2 mg, 0.617 mmol) in 5 mL ethyl acetate was added pentafluorophenol (227.1 mg, 1.23 mmol) at 0° C. After 10 minutes, 5-oxo-pyrrolidine-3-carboxylic acid 12 (210.3 mg, 0.411 mmol) was added at 0° C. and the reaction mixture was stirred for 1 hour at room temperature. After evaporation of the solvent, the crude product was purified by chromatography on silica gel (ethyl acetate:hexane=1:2→1:1) to yield the corresponding (cis)-5-oxo-pyrrolidine-3-carboxylic acid pentafluorophenyl ester 13 as a colourless oil (78.2 mg, 28.9%).

Amide Coupling

To a suspension of (cis)-5-oxo-pyrrolidine-3-carboxylic acid pentafluorophenyl ester 13 (78.2 mg, 0.1154 mmol) in 2 mL THF extra dry was added piperazine (39.8 mg, 0.4616 mmol) at room temperature. The reaction mixture was stirred for 10 hours at room temperature. Afterwards, 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was purified by chromatography on silica gel (ethyl acetate: methanol 9:1→1:1) to afford the desired (cis)-4-(piperazine-1-carbonyl)-pyrrolidin-2-one 14 as a white solid (38.5 mg, 57.55%).

Reaction with Ethyl Isocyanate

To a solution of compound 14 (38.5 mg, 0.066 mmol) in 3 mL THF extra dry was added ethyl isocyanate (14.2 mg, 0.199 mmol) at −30° C. After 1 h of stirring at −30° C., 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was crystallized from ethyl acetate:methanol 19:1 to yield PXN790-d1 as a white solid (26.9 mg, 62.24%).

$^1$H-NMR (400 MHz, DMSO) δ 11.57 (s, 1H), 7.58-7.43 (m, 3H), 7.28-7.11 (m, 5H), 6.95-6.83 (m, 4H), 6.55 (s, 1H), 4.97-4.91 (m, 1H), 4.71 (d, 1H, J=15.24 Hz), 3.63-3.57 (m, 5H), 3.10-3.08 (m, 3H), 2.91-2.85 (m, 3H), 2.69-2.65 (m, 1H), 1.03 (t, 3H, J=7.02 Hz).

IR: 3043, 3165, 3033, 2964, 2930, 1677, 1615, 1538, 1449, 1401, 1262, 1240, 1207, 1119, 796, 698.

MS (+ESI): m/z=650.1 [M+H], 672.1 [M+Na].

Overall yield (four preparative steps): 0.93%

Example 5

Replacement of the Sulfur S (Group X) by Oxygen O

Synthesis of (cis)-4-[1-(4-Chloro-3-fluoro-benzyl)-2-(6-chloro-1H-indol-3-yl)-5-oxo-3-p-tolyloxy-pyrrolidine-3-carbonyl]-piperazine-1-carboxylic Acid Ethylamide [PXN789-d1]

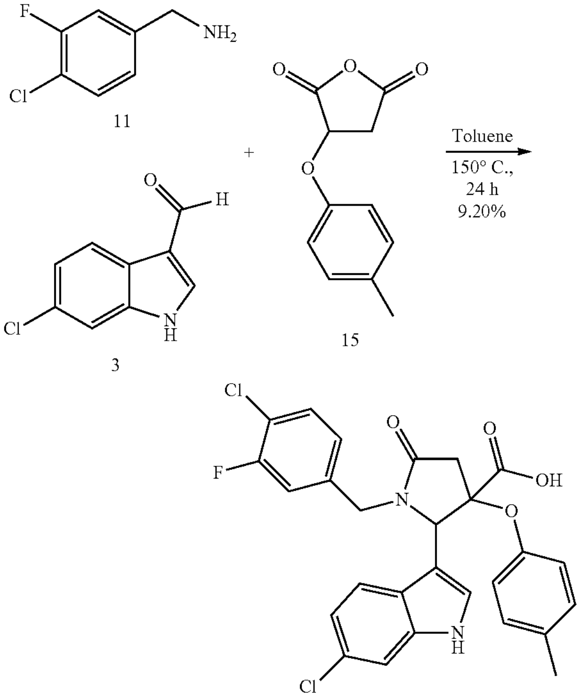

11

3

15

16

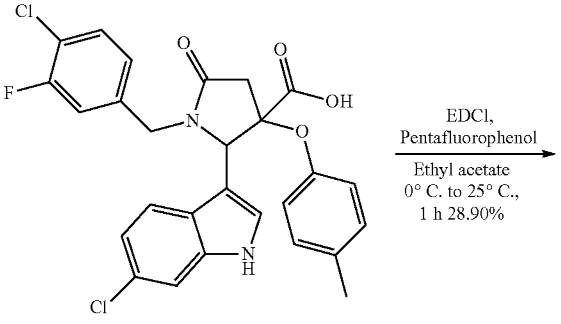

16

-continued

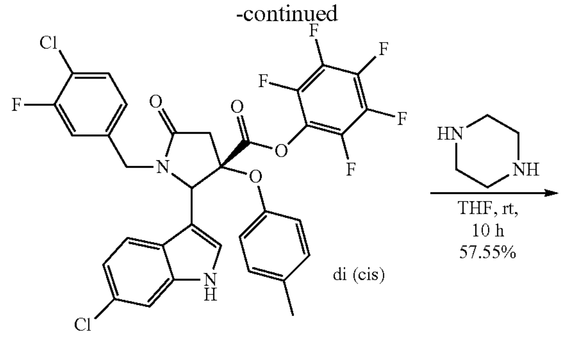

17

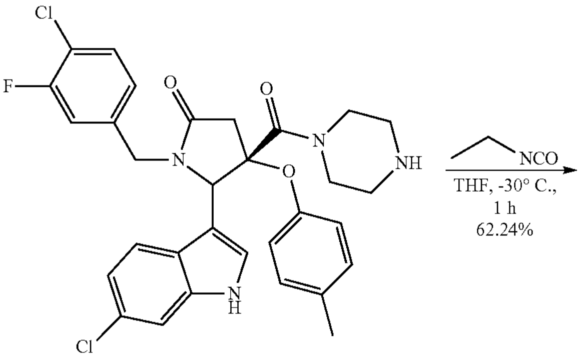

18

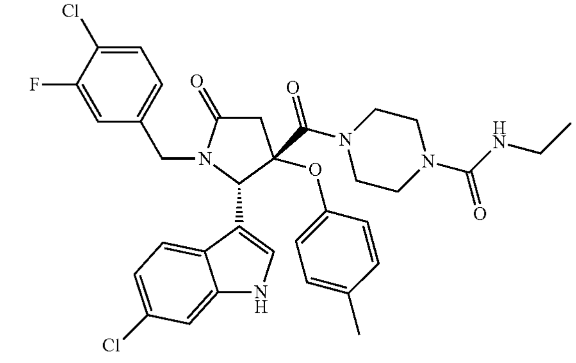

PXN 789-d1

Synthesis of the Oxo-Substituted Anhydride

The oxo-substituted anhydride was obtained via a three-step synthesis:

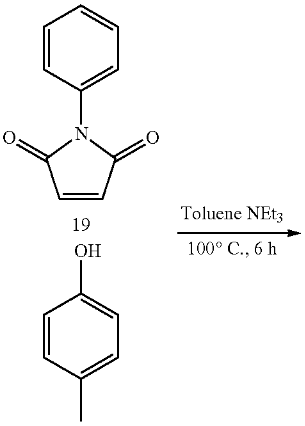

19

20

-continued

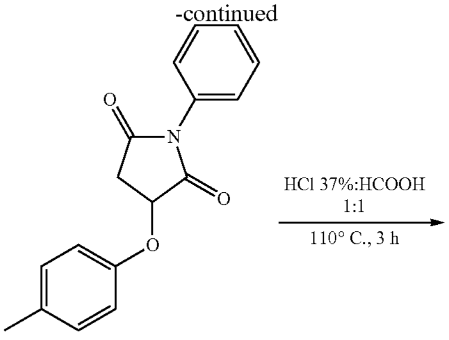

21

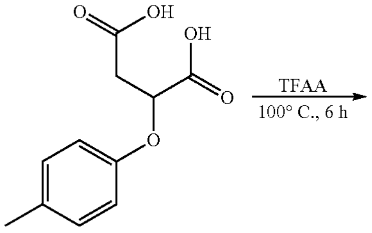

22

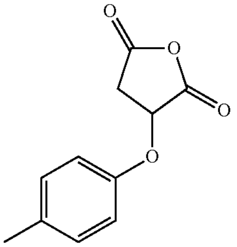

15

1-Phenyl-2,5-dihydro-1H-pyrrole-2,5-dione 19 (5.19 g, 3 mmol), p-cresol 20 (3.24 g, 3 mmol), and triethylamine (3.03 g, 3 mmol) were added in 20 ml toluene extra dry and heated at 100° C. for 6 h. Afterwards, the mixture was cooled to 0° C. The precipitated solid was filtered and washed with cold toluene and hexane to yield compound 21 as a purple solid (2.895 g, 34.30%).

Analytic Data for Compound 21:

$^1$H NMR (DMSO, 399.83 MHz): 2.26 (s, 3H), 2.89-2.94 (m, 1H), 3.31-3.46 (m, 1H), 5.44-5.47 (m, 1H), 6.97 (d, 2H, J=8.4 Hz), 7.14 (d, 2H, J=7.6 Hz), 7.33 (d, 2H, J=7.2 Hz), 7.44-7.53 (m, 3H).

MS (+ESI): m/z=282 [M+H].

Compound 21 (610.3 mg, 2.17 mmol) was dissolved in 30 ml of a mixture of aqueous HCl 37%:HCOOH 1:1. The mixture was heated for 3 h at 110° C. Afterwards, the mixture was cooled to room temperature and the aqueous phase was washed 3 times with DCM and then evaporated. The resulting solid was washed 3 times with cold ether and the resulting ether phase evaporated to yield the succinic acid 22 as a white solid. Finally, the succinic acid 22 was solved in 10 ml of trifluoroacetic anhydride (TFAA) and heated for 6 h at 100° C. Then TFAA was evaporated and the resulting solid was washed with cold hexane to yield the corresponding succinic anhydride 15 as a white solid (170.4 mg, 95.56%).

Analytic Data for Compound 15:

$^1$H NMR (DMSO, 399.43 MHz): 2.25 (s, 3H), 3.21-3.27 (m, 1H), 3.52-3.59 (m, 1H), 5.57-5.61 (m, 1H), 6.92 (d, 2H, J=8.26 Hz), 7.14 (d, 2H, J=8.22 Hz).

IR: 3001, 2920, 1865, 1781, 1608, 1508, 1396, 1213, 1178, 1086, 1021, 903, 806.

MS (+BSI): m/z=207 [M+H].

Multicomponent Reaction

First, aldehyde 3 (646.6 mg, 3.6 mmol) and amine 11 (478.8 mg, 3 mmol) were condensed in 3 mL trimethylorthoformiate for 10 hours at room temperature. Then, the solvent was removed in vacuo and the residue was solved in 25 mL o-xylene. Afterwards, succinic anhydride 15 (850 mg, 4.5 mmol) was added and the mixture was heated to 150° C. for 24 hours under Dean-Stark conditions. After cooled to room temperature, the solution was concentrated in vacuo. Purification on silica gel (ethyl acetate: methanol=9:1→1:1) yielded MCR-product 16 as a diastereoisomeric mixture (33.9 mg, 2.11%).

Pentafluorophenyl Ester Formation

To a suspension of 1-(3-dimethylaminopropyl)-3-ethylcarbodiimide hydrochloride EDCI (18.5 mg, 0.096 mmol) in 2 mL ethyl acetate was added pentafluorophenol (35.6 mg, 0.193 mmol) at 0° C. After 10 minutes, 5-oxo-pyrrolidine-3-carboxylic acid 16 (33.9 mg, 0.064 mmol) was added at 0° C. and the reaction mixture was stirred for 1 hour at room temperature. After evaporation of the solvent, the crude product was purified by chromatography on silica gel (ethyl acetate: hexane=1:2) to yield the corresponding 5-oxo-pyrrolidine-3-carboxylic acid pentafluorophenyl ester 17 as a colourless oil (40.1 mg, 89.80%).

Amide Coupling

To a suspension of 5-oxo-pyrrolidine-3-carboxylic acid pentafluorophenyl ester 17 (40.1 mg, 0.0578 mmol) in 2 mL THF extra dry was added piperazine (19.9 mg, 0.231 mmol) at room temperature. The reaction mixture was stirred for 10 hours at room temperature. Afterwards, 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was purified by chromatography on silica gel (ethyl acetate:methanol 9:1→1:1) to afford the desired 4-(piperazine-1-carbonyl)-pyrrolidin-2-one 18 as a white solid (12.2 mg, 45.91%).

Reaction with Ethyl Isocyanate

To a solution of compound 18 (12.2 mg, 0.0204 mmol) in 3 mL THF extra dry was added ethyl isocyanate (4.4 mg, 0.0612 mmol) at −30° C. After 1 h of stirring at −30° C., 20 mL methylene chloride were added. The resulting organic layer was washed with 20 mL of a saturated aqueous solution of sodium hydrogenocarbonate, dried over magnesium sulfate and the solvent was removed in vacuo. Finally, the crude product was purified by chromatography on silica gel (methylene chloride:methanol 95:5) to yield PXN789-d1 as a yellow solid (9.6 mg, 70.60%).

MS (+ESI): m/z=666.1 [M+H].

Overall yield (four preparative steps): 0.61%

Further Examples

Further examples which have been prepared according to one of the procedures described above: All products were obtained and tested as racemates. The cellular activity was measured on p53 wild type ovarian teratocarcinoma cells (PA-1) and measured $IC_{50}$ are given in micromolar. CCA is the abbreviation of Cell Cycle Arrest.

PXN610
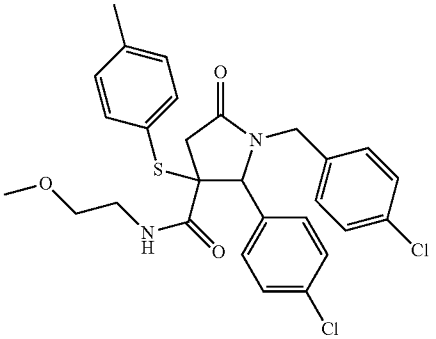
$C_{28}H_{28}Cl_2N_2O_3S$; MW: 543.52; found (HPLC MS): $[M + H^+]$ = 543.0; Yield: 47%; $IC_{50}$ = 15
PXN611
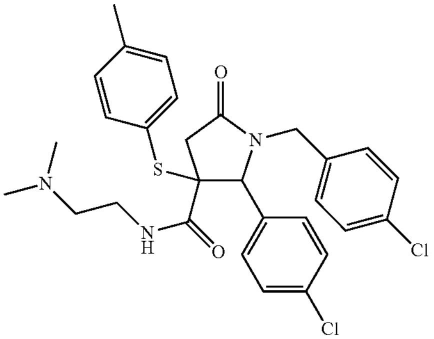
$C_{29}H_{31}Cl_2N_3O_2S$; MW: 556.56; found (HPLC MS): $[M + H^+]$ = 556.1; Yield: 28%; $IC_{50}$ = 8.3
PXN612
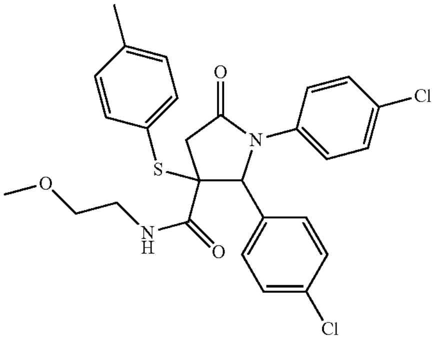
$C_{27}H_{26}Cl_2N_2O_3S$; MW: 529.49; found (HPLC MS): $[M + H^+]$ = 529.0; Yield: 17%; $IC_{50}$ = 10.3
PXN613
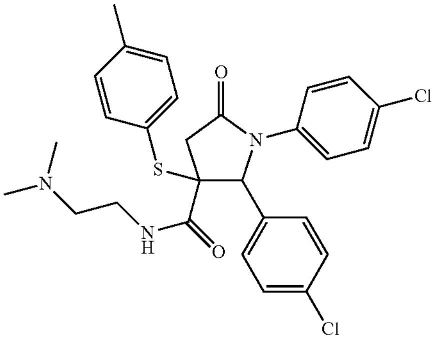
$C_{28}H_{29}Cl_2N_3O_2S$; MW: 542.53; found (HPLC MS): $[M + H^+]$ = 542.0; Yield: 13%; $IC_{50}$ = 8
PXN617
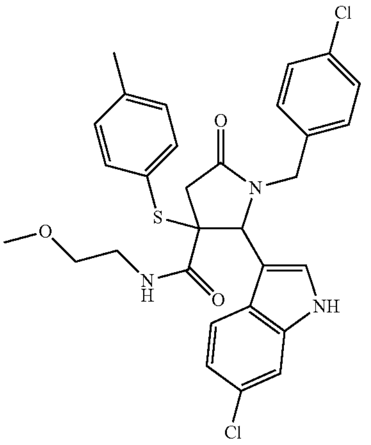
$C_{30}H_{29}Cl_2N_3O_3S$; MW: 582.55; found (HPLC MS): $[M + H^+]$ = 582.1; $[M+Na^+]$ = 604.0; Yield: 32%; $IC_{50}$ = 3.1
PXN618
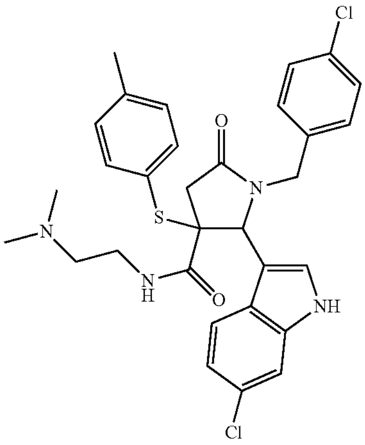
$C_{31}H_{32}Cl_2N_4O_2S$; MW: 595.60; found (HPLC MS): $[M + H^+]$ = 595.1; Yield: 35%; $IC_{50}$ = 4.2

-continued
PXN619
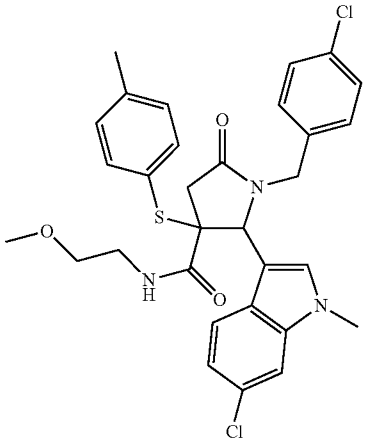
$C_{31}H_{31}Cl_2N_3O_3S$; MW: 596.58; found (HPLC MS): [M + $Na^+$] = 618.1; Yield: 40%; $IC_{50}$ = 28.7
PXN620
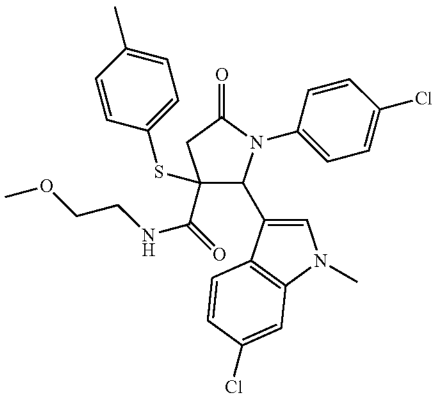
$C_{30}H_{29}Cl_2N_3O_3S$; MW: 582.55; found (HPLC MS): [M + $H^+$] = 581.9; Yield: 15%; $IC_{50}$ = 15.3
PXN623
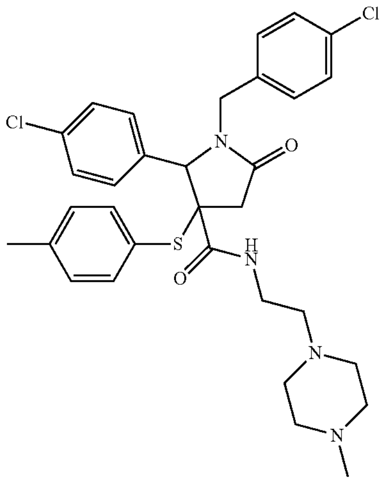
$C_{32}H_{36}Cl_2N_4O_2S$; MW: 611.64; found (HPLC MS): [M + $H^+$] = 611.1; Yield: 49%; $IC_{50}$ = 7.8
PXN624
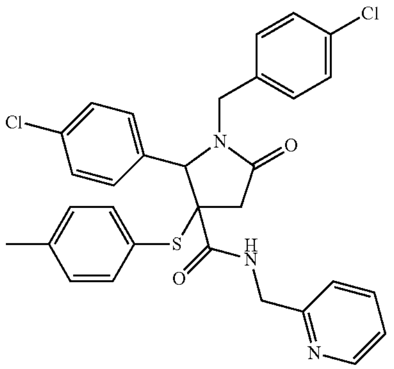
$C_{31}H_{27}Cl_2N_3O_2S$; MW: 576.55; found (HPLC MS): [M + $H^+$] = 576.0; Yield: 41%; $IC_{50}$ = 22.4
PXN625
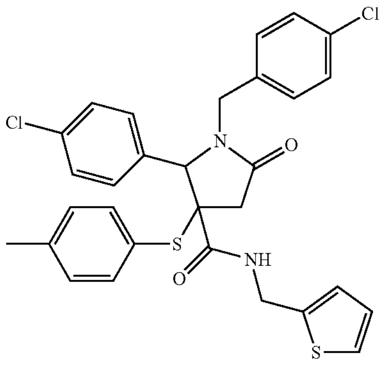
$C_{30}H_{26}Cl_2N_2O_2S_2$; MW: 581.59; found (HPLC MS): [M + $H^+$] = 581.1; Yield: 37%; $IC_{50}$ >60
PXN626
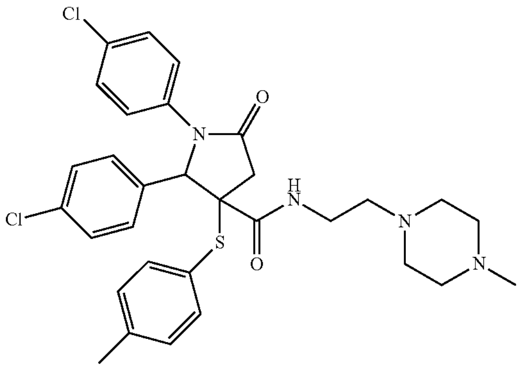
$C_{31}H_{34}Cl_2N_4O_2S$; MW: 597.61; found (HPLC MS): [M + $H^+$] = 597.1; Yield: 21%; $IC_{50}$ = 7.4

-continued
PXN627
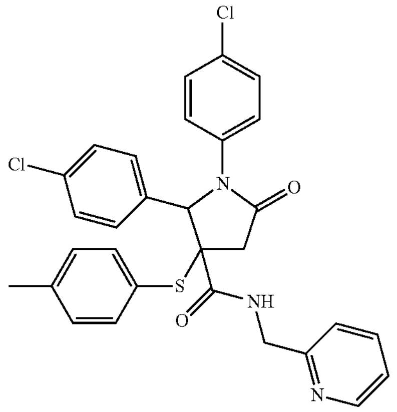
$C_{30}H_{25}Cl_2N_3O_2S$; MW: 562.52; found (HPLC MS): $[M + H^+]$ = 562.0; Yield: 17%; $IC_{50}$ = 10.2
PXN628
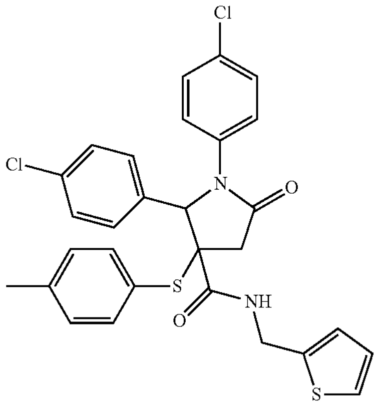
$C_{29}H_{24}Cl_2N_2O_2S_2$; MW: 567.56; found (HPLC MS): $[M + H^+]$ = 567.0; Yield: 20%; $IC_{50}$ > 60
PXN629
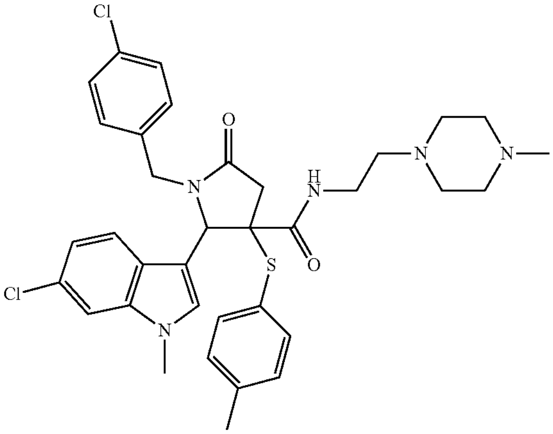
$C_{35}H_{39}Cl_2N_5O_2S$; MW: 664.70; found (HPLC MS): $[M + H^+]$ = 664.2; Yield: 40%; $IC_{50}$ = 7.2
PXN630-d1
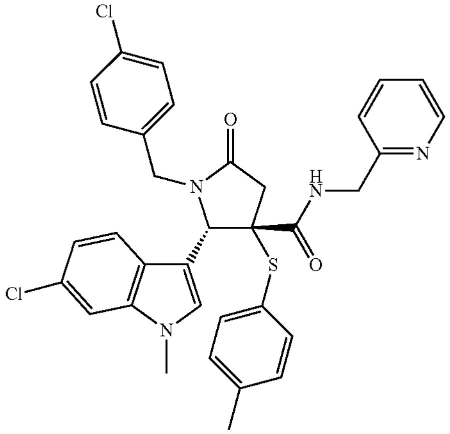
$C_{34}H_{30}Cl_2N_4O_2S$; MW: 629.61; found (HPLC MS): $[M + H^+]$ = 629.1; Yield: 38%; $IC_{50}$ > 60
PXN631-d1
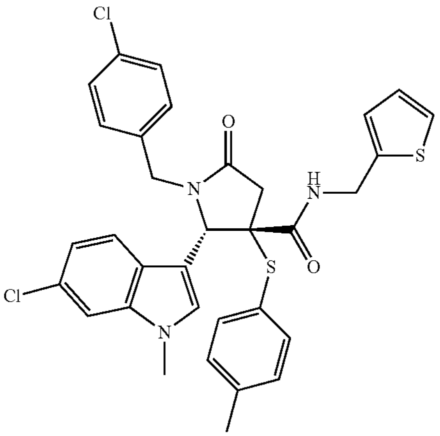
$C_{33}H_{29}Cl_2N_3O_2S_2$; MW: 634.65; found (HPLC MS): $[M + Na^+]$ = 656.0; Yield: 30%; $IC_{50}$ > 60
PXN632
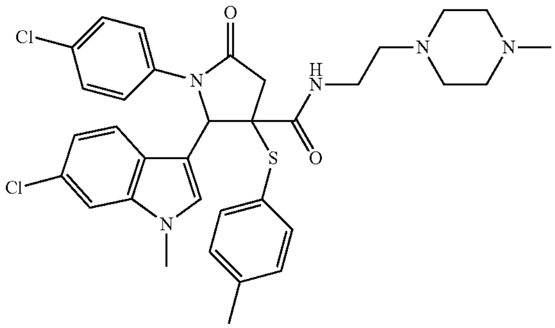
$C_{34}H_{37}Cl_2N_5O_2S$; MW: 650.68; found (HPLC MS): $[M + H^+]$ = 650.2; Yield: 36%; $IC_{50}$ = 5.2

-continued
PXN633-d1
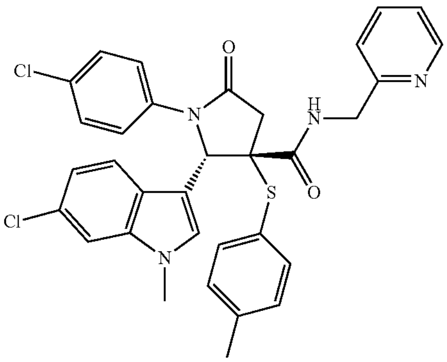
$C_{33}H_{28}Cl_2N_4O_2S$; MW: 615.59; found (HPLC MS): $[M + H^+]$ = 615.1; Yield: 17%; $IC_{50}$ = 23.3
PXN633-d2
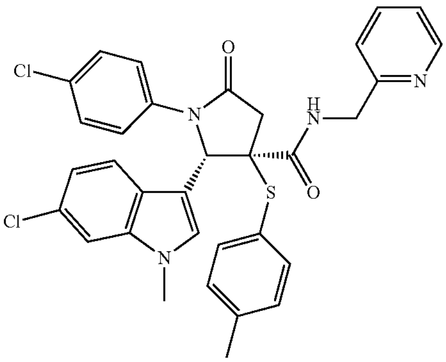
$C_{33}H_{28}Cl_2N_4O_2S$; MW: 615.59; found (HPLC MS): $[M + H^+]$ = 615.1; Yield: 11%; $IC_{50}$ = 22.2
PXN634
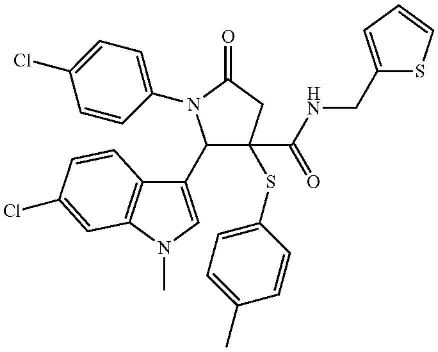
$C_{32}H_{27}Cl_2N_3O_2S_2$; MW: 620.62; found (HPLC MS): $[M + H^+]$ = 620.0; Yield: 27%; $IC_{50} > 60$
PXN635
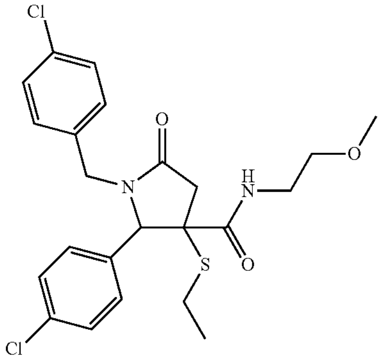
$C_{23}H_{26}Cl_2N_2O_3S$; MW: 481.45
PXN636
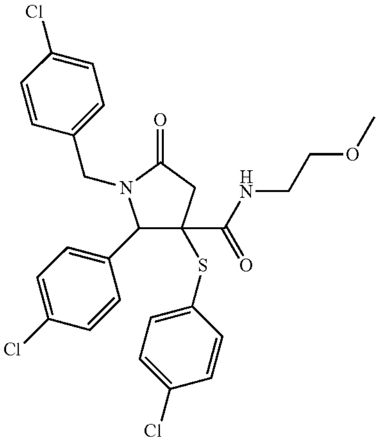
$C_{27}H_{25}Cl_3N_2O_3S$; MW: 563.93; found (HPLC MS): $[M + H^+]$ = 563.0; Yield: 26%; $IC_{50} > 60$
PXN637
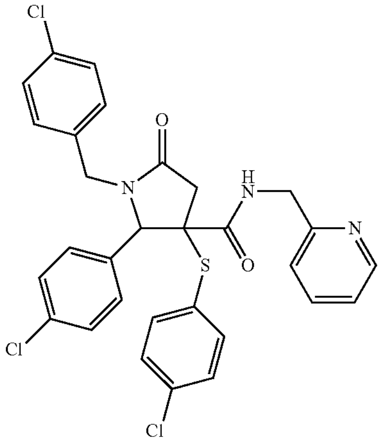
$C_{30}H_{24}Cl_3N_3O_2S$; MW: 596.97; found (HPLC MS): $[M + H^+]$ = 596.0; Yield: 24%; $IC_{50} > 60$ -continued
PXN638
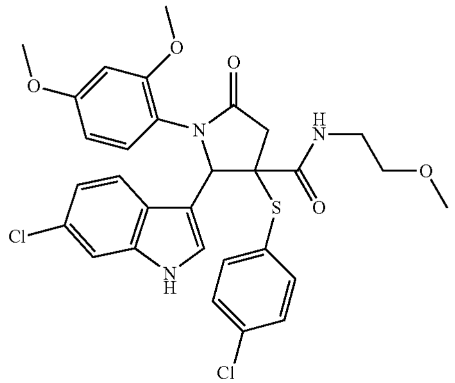
$C_{30}H_{29}Cl_2N_3O_5S$; MW: 614.55; found (HPLC MS): $[M+H^+]$ = 614.1; Yield: 11%; $IC_{50}$ = 60.4
PXN639
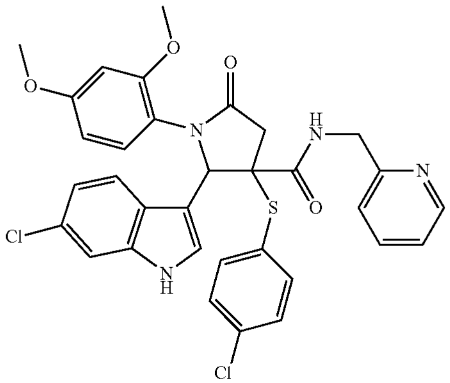
$C_{33}H_{28}Cl_2N_4O_4S$; MW: 647.59; found (HPLC MS): $[M+H^+]$ = 647.1; Yield: 5%; $IC_{50}$ = 65.7
PXN640-d1
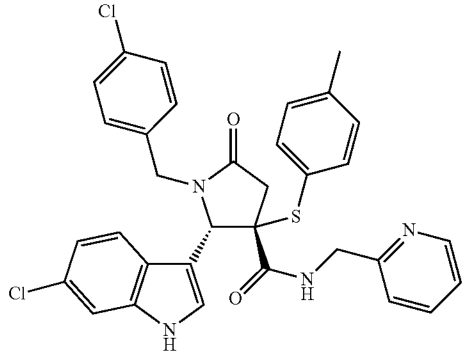
$C_{33}H_{28}Cl_2N_4O_2S$; MW: 615.59; found (HPLC MS): $[M+H^+]$ = 615.2; Yield: 13%; $IC_{50}$ = 18.7
PXN640-d2
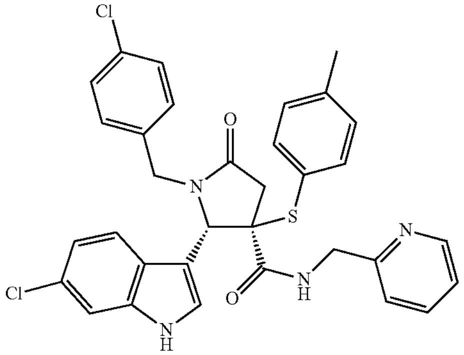
$C_{33}H_{28}Cl_2N_4O_2S$; MW: 615.59; found (HPLC MS): $[M+H^+]$ = 615.2; Yield: 5%; $IC_{50}$ = 24.5
PXN641
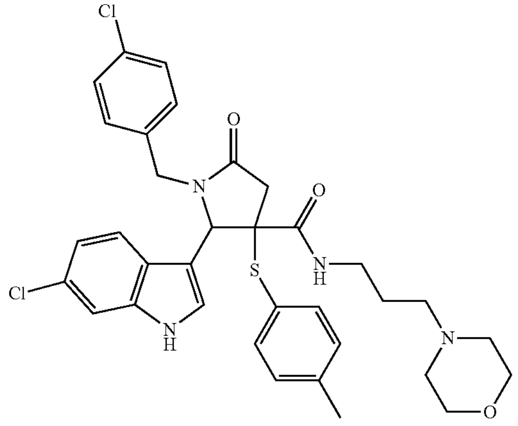
$C_{34}H_{36}Cl_2N_4O_3S$; MW: 651.66; found (HPLC MS): $[M+H^+]$ = 651.2; Yield: 9%; $IC_{50}$ = 9.4
PXN642
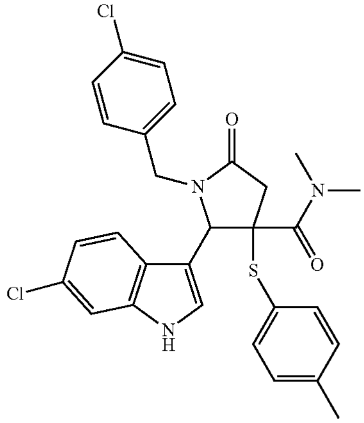
$C_{29}H_{27}Cl_2N_3O_2S$; MW: 552.53; found (HPLC MS): $[M+H^+]$ = 552.1; $[M+Na^+]$ = 574.1; Yield: 8%; $IC_{50}$ = 5.7

-continued
PXN643
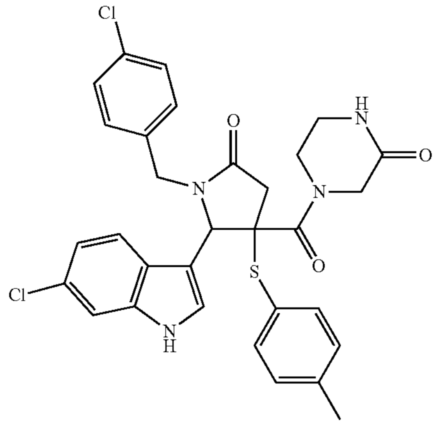
$C_{31}H_{28}Cl_2N_4O_3S$; MW: 607.56; found (HPLC MS): $[M + H^+]$ = 607.2; Yield: 4%; $IC_{50}$ = 3.9
PXN644
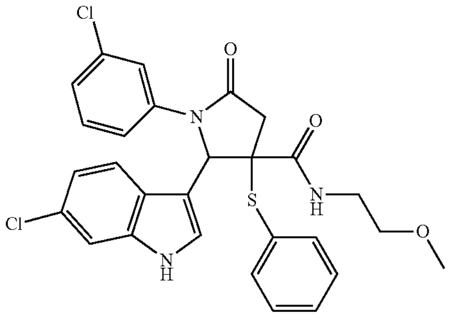
$C_{28}H_{25}Cl_2N_3O_3S$; MW: 554.50; found (HPLC MS): $[M + Na^+]$ = 576.1; Yield: 10%; $IC_{50}$ = 13.5
PXN645
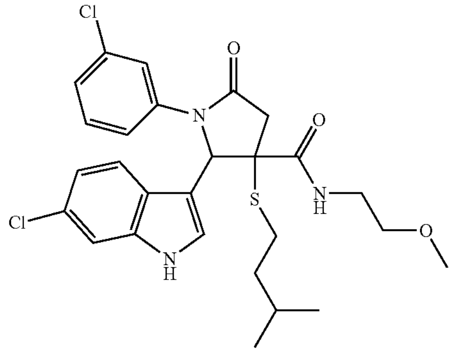
$C_{27}H_{31}Cl_2N_3O_3S$; MW: 548.54; found (HPLC MS): $[M + Na^+]$ = 570.2; Yield: 1%
PXN646
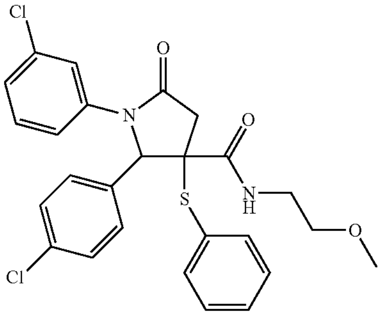
$C_{26}H_{24}Cl_2N_2O_3S$; MW: 515.46; found (HPLC MS): $[M + H^+]$ = 515.0; Yield: 11%; $IC_{50}$ = 14.6
PXN647
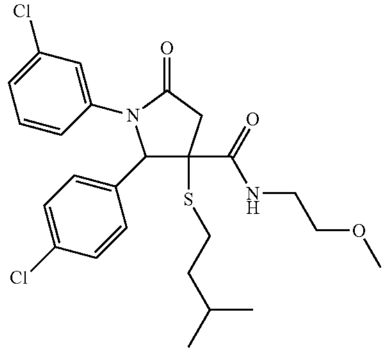
$C_{25}H_{30}Cl_2N_2O_3S$; MW: 509.50
PXN649
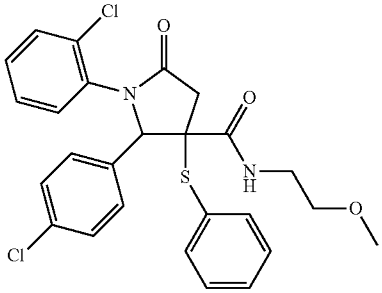
$C_{26}H_{24}Cl_2N_2O_3S$; MW: 515.46

-continued
PXN650
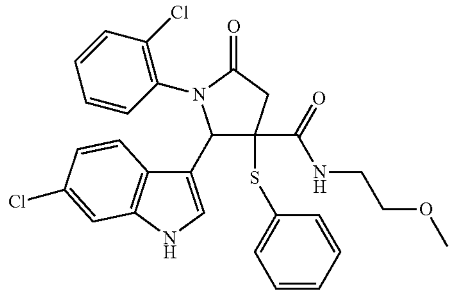
$C_{28}H_{25}Cl_2N_3O_3S$; MW: 554.50; found (HPLC MS): $[M + Na^+] = 576.1$; Yield: 8%; $IC_{50} = 17.1$
PXN651
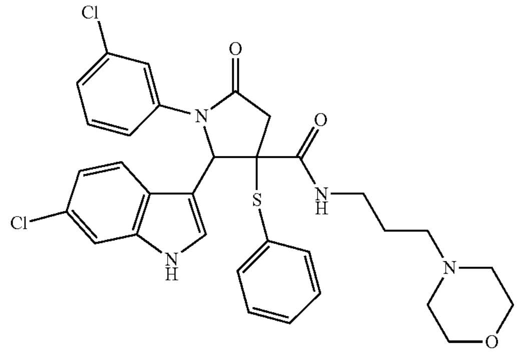
$C_{32}H_{32}Cl_2N_4O_3S$; MW: 623.61; found (HPLC MS): $[M + H^+] = 623.2$; Yield: 9%; $IC_{50} = 9.2$
PXN652
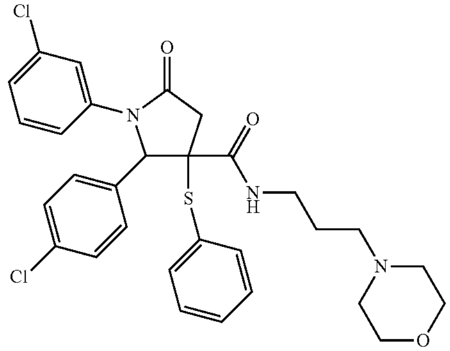
$C_{30}H_{31}Cl_2N_3O_3S$; MW: 584.57; found (HPLC MS): $[M + H^+] = 584.1$; Yield: 29%; $IC_{50} = 17.4$
PXN653
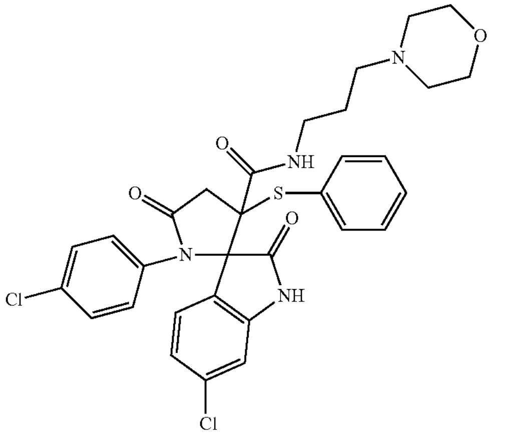
$C_{31}H_{31}Cl_2N_4O_4S$; MW: 625.58; found (HPLC MS): $[M + H^+] = 625.1$; Yield: 2%
PXN654
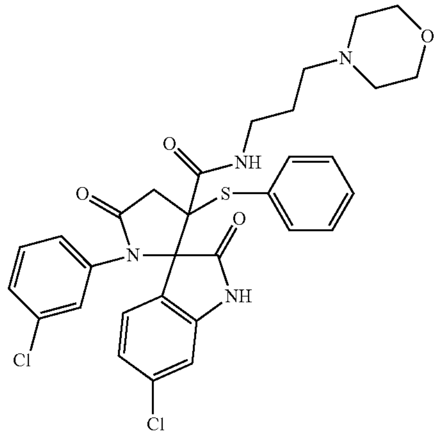
$C_{31}H_{30}Cl_2N_4O_4S$; MW: 625.58; found (HPLC MS): $[M + H^+] = 625.1$; Yield: 3%; $IC_{50} = 29.9$
PXN655
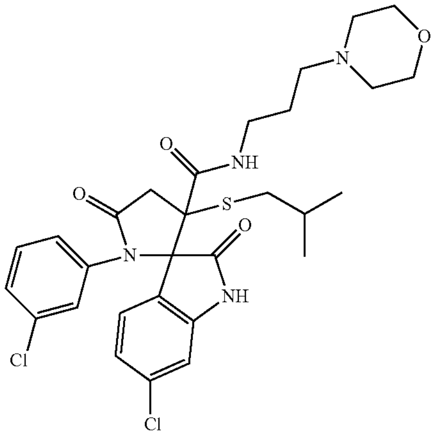
$C_{29}H_{34}Cl_2N_4O_4S$; MW: 605.59

-continued
PXN656
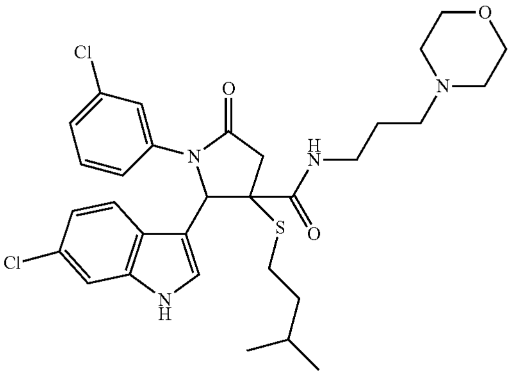
$C_{31}H_{38}Cl_2N_4O_3S$; MW: 617.64; found (HPLC MS): $[M + H^+] = 617.2$; Yield: 1%; $IC_{50} = 17.8$
PXN657
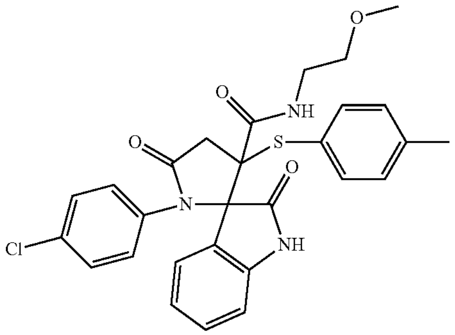
$C_{28}H_{26}ClN_3O_4S$; MW: 536.05; found (HPLC MS): $[M + H^+] = 536.1$; Yield: 11%
PXN658
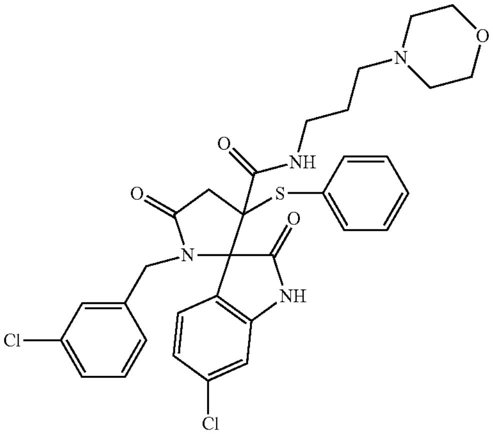
$C_{32}H_{32}Cl_2N_4O_4S$; MW: 639.61
PXN659-d1
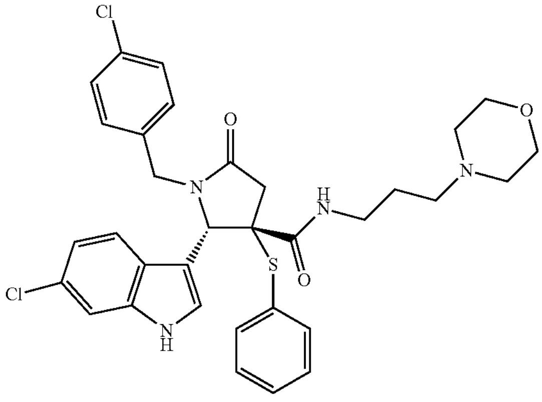
$C_{33}H_{34}Cl_2N_4O_3S$; MW: 637.63; found (HPLC MS): $[M + H^+] = 637.2$; Yield: 7%; $IC_{50} = 6.8$
PXN659-d2
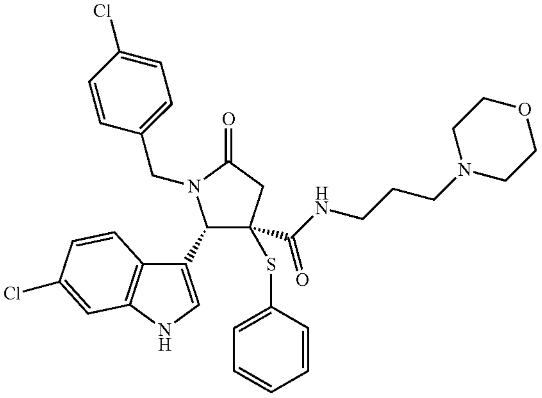
$C_{33}H_{34}Cl_2N_4O_3S$; MW: 637.63; found (HPLC MS): $[M + H^+] = 637.2$; Yield: 7%; $IC_{50} = 12$
PXN660-d1
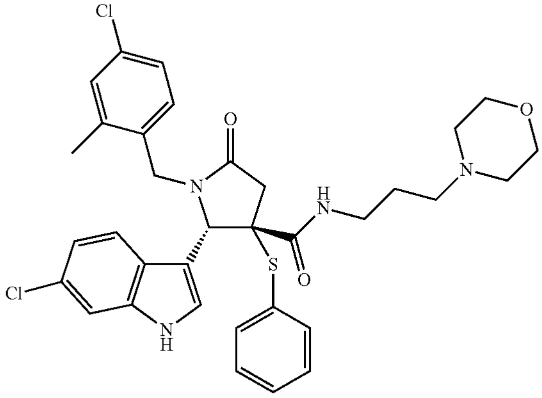
$C_{34}H_{36}Cl_2N_4O_3S$; MW: 651.66; found (HPLC MS): $[M + H^+] = 651.2$; Yield: 8%; $IC_{50} = 13$ -continued
PXN660-d2
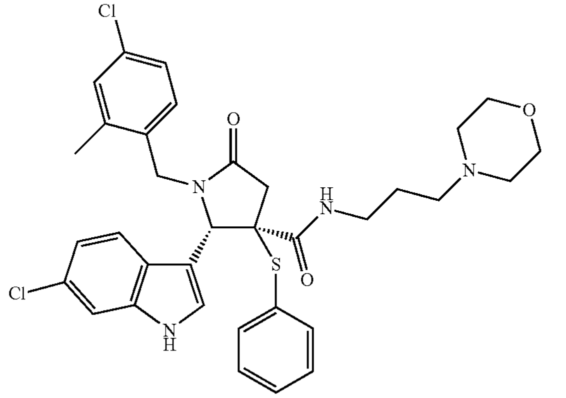
$C_{34}H_{36}Cl_2N_4O_3S$; MW: 651.66; found (HPLC MS): $[M+H^+]$ = 651.2; Yield: 5%; $IC_{50}$ = 8.3
PXN661-d1
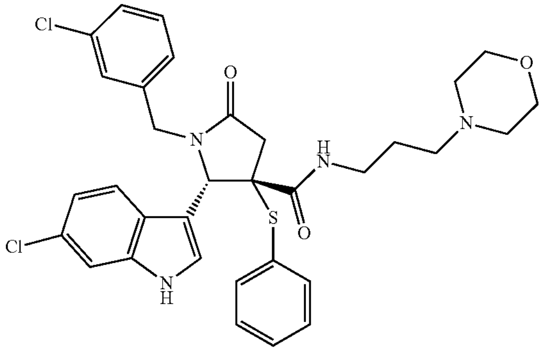
$C_{33}H_{34}Cl_2N_4O_3S$; MW: 637.63; found (HPLC MS): $[M+H^+]$ = 637.2; Yield: 4%; $IC_{50}$ = 13.8
PXN661-d2
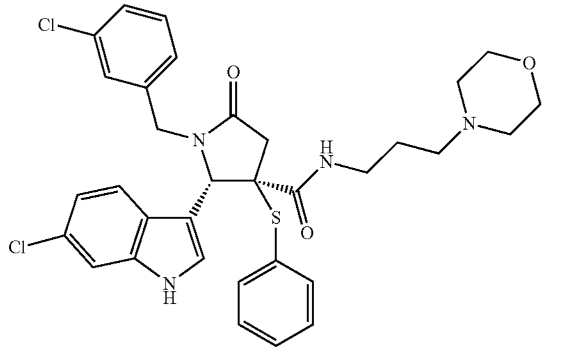
$C_{33}H_{34}Cl_2N_4O_3S$; MW: 637.63; found (HPLC MS): $[M+H^+]$ = 637.2; Yield: 3%; $IC_{50}$ = 10.2
PXN662-d1
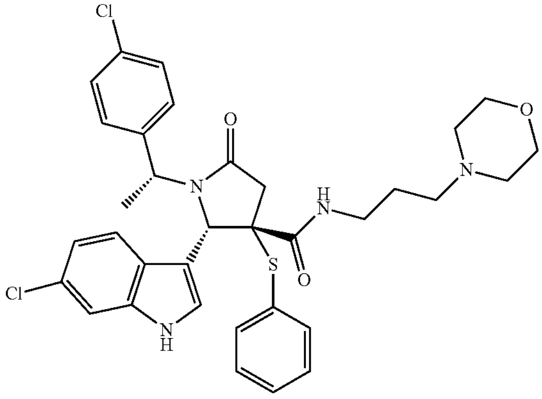
$C_{34}H_{36}Cl_2N_4O_3S$; MW: 651.66; found (HPLC MS): $[M+H^+]$ = 651.2; Yield: 1%; $IC_{50}$ = 17.2
PXN662-d2
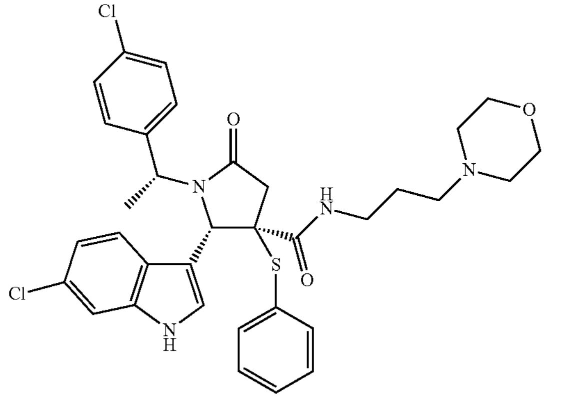
$C_{34}H_{36}Cl_2N_4O_3S$; MW: 651.66; found (HPLC MS): $[M+H^+]$ = 651.2; Yield: 3%; $IC_{50}$ = 11.5
PXN663-d1
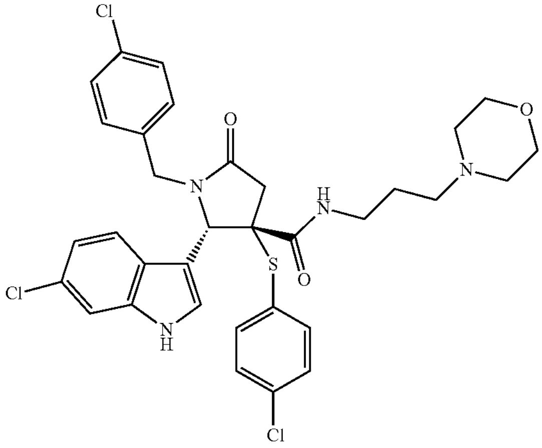
$C_{33}H_{33}Cl_3N_4O_3S$; MW: 672.08; found (HPLC MS): $[M+H^+]$ = 673.1; Yield: 19%; $IC_{50}$ = 9.2

-continued
PXN663-d2
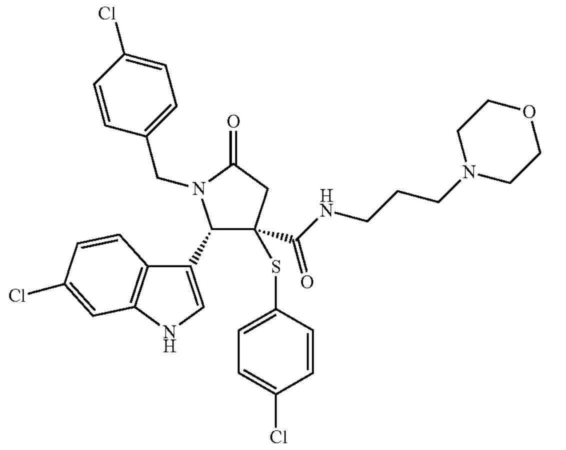
$C_{33}H_{33}Cl_3N_4O_3S$; MW: 672.08; found (HPLC MS): $[M + H^+]$ = 671.1; Yield: 7%; $IC_{50}$ = 11.2
PXN666-d1
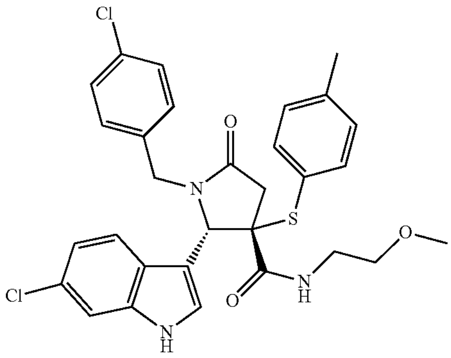
$C_{30}H_{29}Cl_2N_3O_3S$; MW: 582.55; PXN617-enantiomer1; $IC_{50}$ = 2.9
PXN667-d1
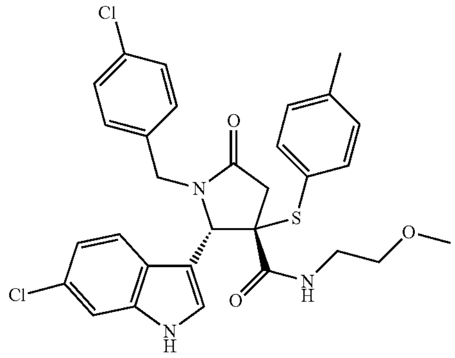
$C_{30}H_{29}Cl_2N_3O_3S$; MW: 582.55; PXN617-enantiomer2; $IC_{50}$ = 39
PXN668-d1
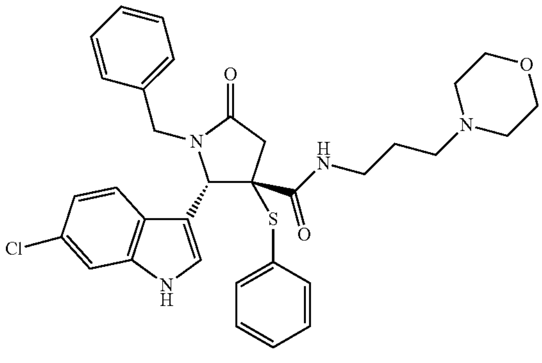
$C_{33}H_{35}ClN_4O_3S$; MW: 603.19; found (HPLC MS): $[M + H^+]$ = 603.0; Yield: 5%; $IC_{50}$ = 18.3
PXN668-d2
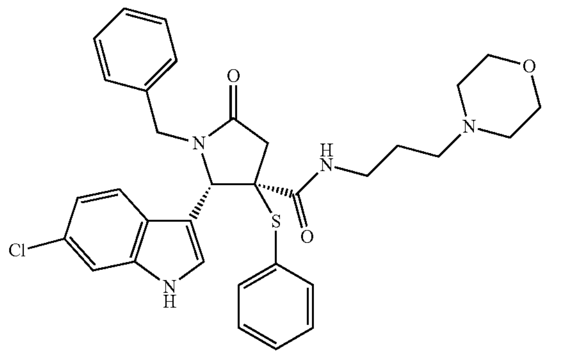
$C_{33}H_{35}ClN_4O_3S$; MW: 603.19; found (HPLC MS): $[M + H^+]$ = 603.0; Yield: 4%; $IC_{50}$ = 26.9
PXN669-d1
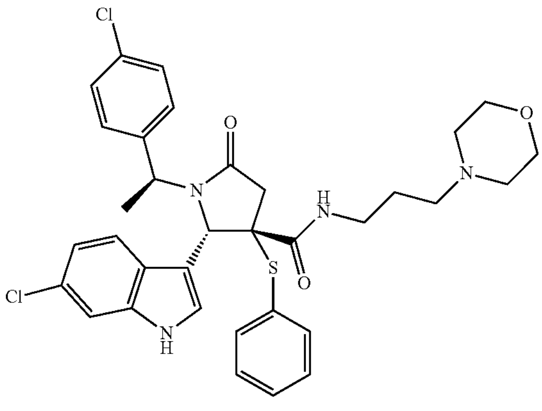
$C_{34}H_{36}Cl_2N_4O_3S$; MW: 651.66; found (HPLC MS): $[M + H^+]$ = 651.0; Yield: 5%; $IC_{50}$ = 16.1

-continued
PXN669-d2
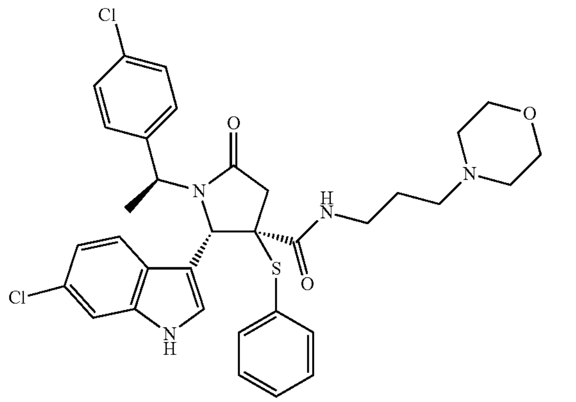
$C_{34}H_{36}Cl_2N_4O_3S$; MW: 651.66; found (HPLC MS): $[M + H^+]$ = 650.9; Yield: 5%; $IC_{50}$ = 10.6
PXN671-d1
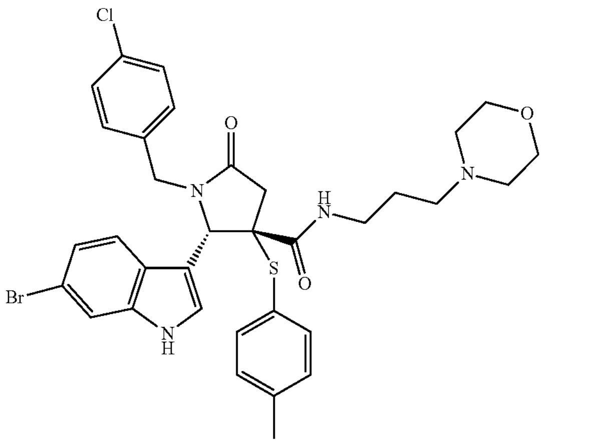
$C_{34}H_{36}BrClN_4O_3S$; MW: 696.11; found (HPLC MS): $[M + H^+]$ = 697.0; Yield: 11%; $IC_{50}$ = 8.7
PXN671-d2
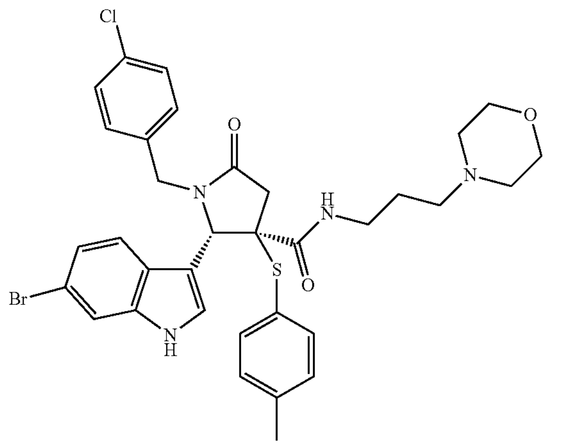
$C_{34}H_{36}BrClN_4O_3S$; MW: 696.11; found (HPLC MS): $[M + H^+]$ = 697.1; Yield: 9%; $IC_{50}$ = 8.5
PXN672-d1
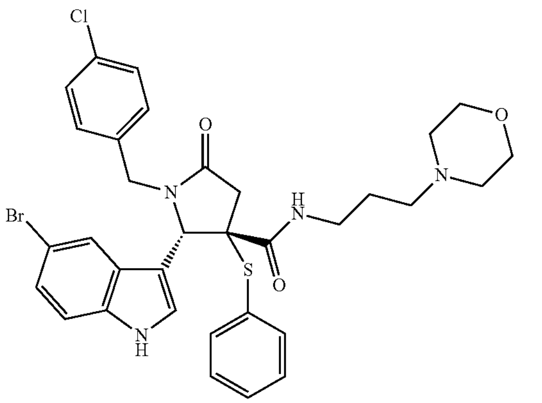
$C_{33}H_{34}BrClN_4O_3S$; MW: 682.08; found (HPLC MS): $[M + H^+]$ = 682.8; Yield: 5%; $IC_{50}$ = 29.5
PXN672-d2
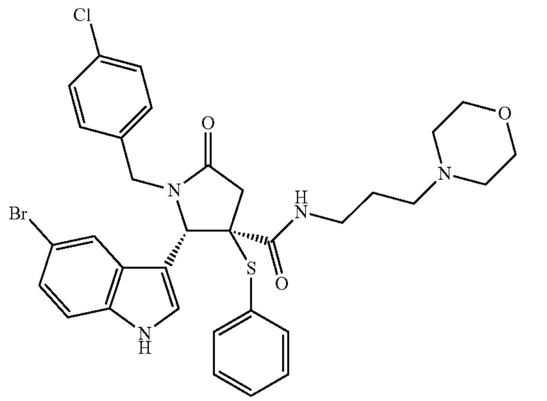
$C_{33}H_{34}BrClN_4O_3S$; MW: 682.08; found (HPLC MS): $[M + H^+]$ = 682.9; Yield: 4%; $IC_{50}$ = 8.8
PXN673-d2
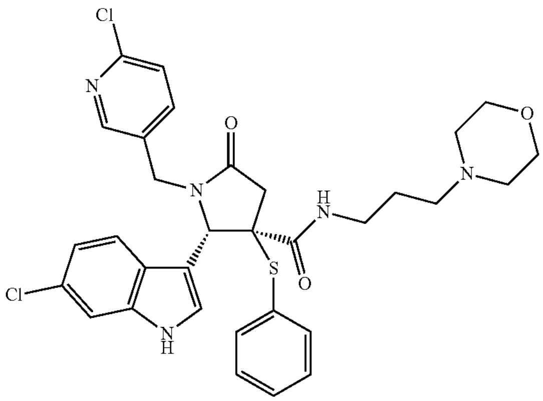
$C_{32}H_{33}Cl_2N_5O_3S$; MW: 638.62; found (HPLC MS): $[M + H^+]$ = 637.9; Yield: 1%; $IC_{50}$ = 163.4

-continued
PXN673-d1
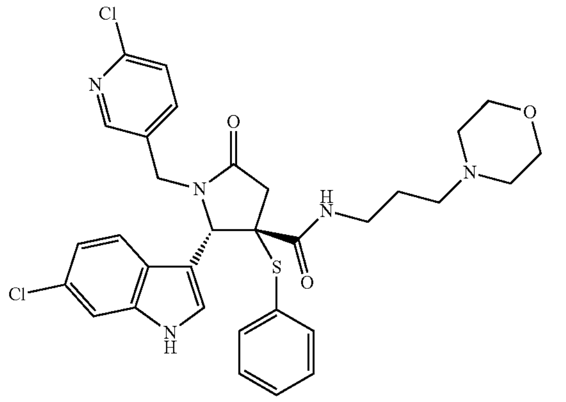
$C_{32}H_{33}Cl_2N_5O_3S$; MW: 638.62; found (HPLC MS): $[M+H^+]$ = 638.0; Yield: 4%; $IC_{50}$ = 9.3
PXN674-d1
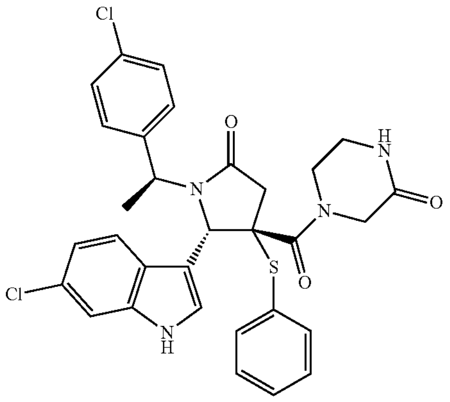
$C_{31}H_{28}Cl_2N_4O_3S$; MW: 607.56; found (HPLC MS): $[M+H^+]$ = 607.2; Yield: 4%; $IC_{50}$ = 17.5
PXN674-d2
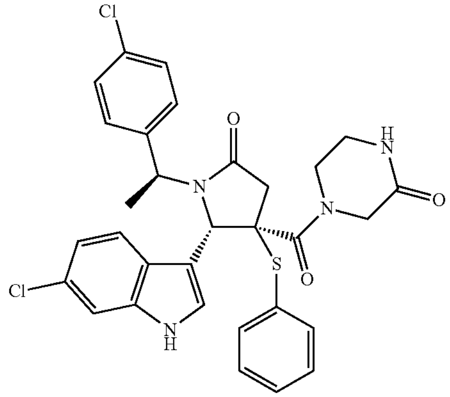
$C_{31}H_{28}Cl_2N_4O_3S$; MW: 607.56; found (HPLC MS): $[M+H^+]$ = 607.2; Yield: 4%; $IC_{50}$ = 28.9
PXN675-d1
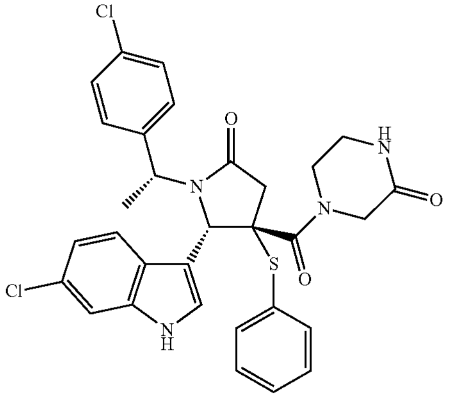
$C_{31}H_{28}Cl_2N_4O_3S$; MW: 607.56; found (HPLC MS): $[M+H^+]$ = 606.9; Yield: 2%; $IC_{50}$ = 25.5
PXN675-d2
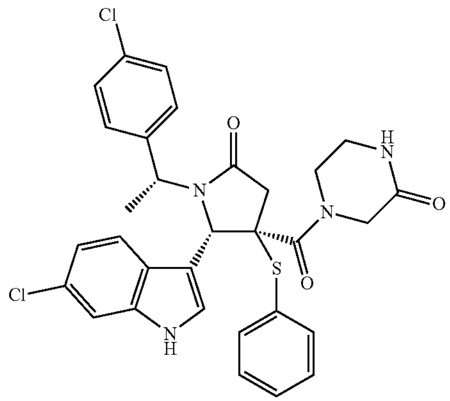
$C_{31}H_{28}Cl_2N_4O_3S$; MW: 607.56; found (HPLC MS): $[M+H^+]$ = 608.8; Yield: 3%; $IC_{50}$ = 17.8
PXN676-d1
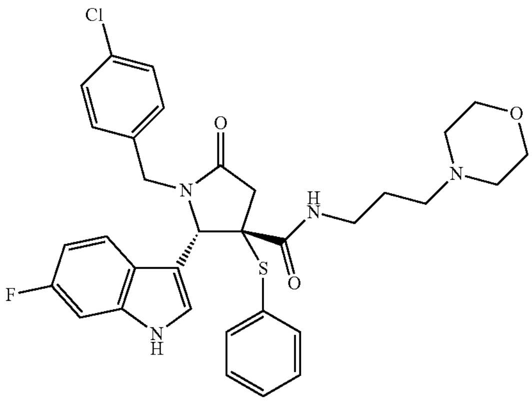
$C_{33}H_{34}ClFN_4O_3S$; MW: 621.18; found (HPLC MS): $[M+H^+]$ = 621.0; Yield: 5%; $IC_{50}$ = 15.6

-continued
PXN676-d2
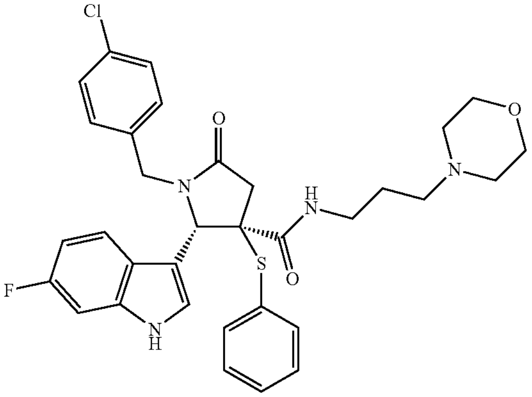
$C_{33}H_{34}ClFN_4O_3S$; MW: 621.18; found (HPLC MS): [M + H$^+$] = 621.0; Yield: 3%; $IC_{50}$ = 18.5
PXN677-d1
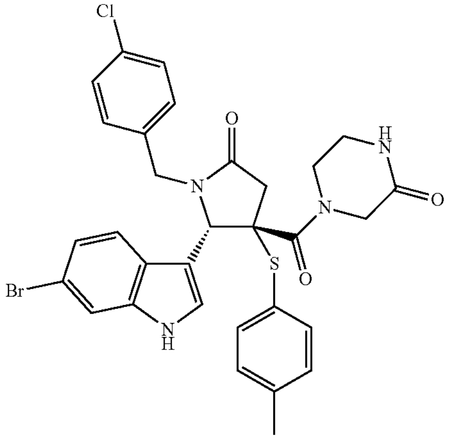
$C_{31}H_{28}BrClN_4O_3S$; MW: 652.01; found (HPLC MS): [M + H$^+$] = 651.3; Yield: 8%; $IC_{50}$ = 5.45
PXN678-d1
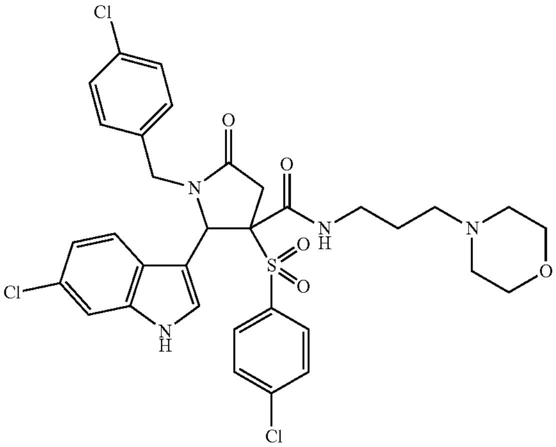
$C_{33}H_{33}Cl_3N_4O_5S$; MW: 704.08; found (HPLC MS): [M + H$^+$] = 702.9; Yield: 5%; $IC_{50}$ = 49.3
PXN679-d2
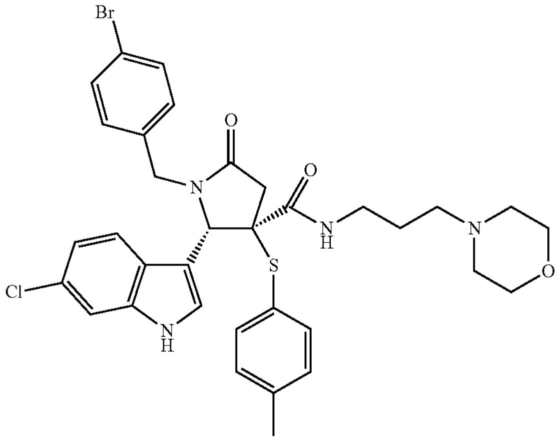
$C_{34}H_{36}BrClN_4O_3S$; MW: 696.11; found (HPLC MS): [M + H$^+$] = 697.1; Yield: 3%; $IC_{50}$ = 9.3
PXN679-d1
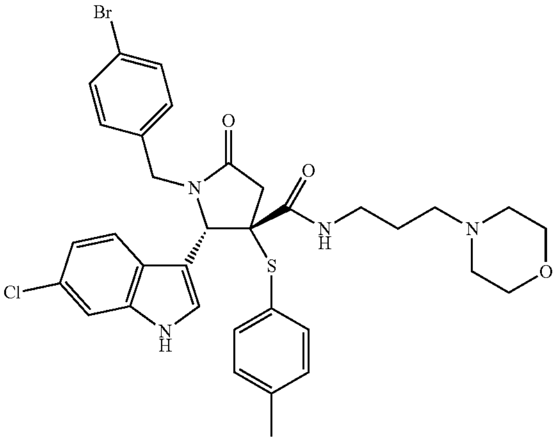
$C_{34}H_{36}BrClN_4O_3S$; MW: 696.11; found (HPLC MS): [M + H$^+$] = 697.2; Yield: 8%; $IC_{50}$ = 7.7
PXN680-d1
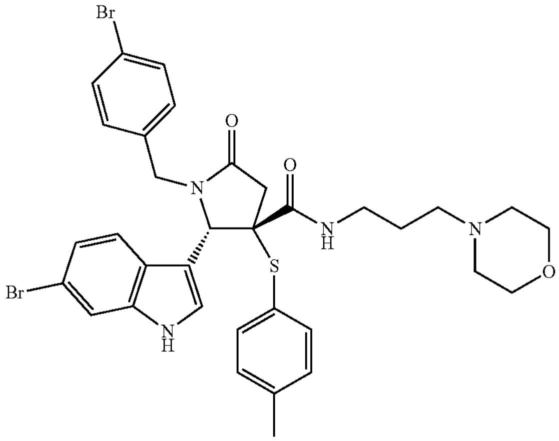
$C_{34}H_{36}Br_2N_4O_3S$; MW: 740.56; found (HPLC MS): [M + H$^+$] = 740.5; Yield: 10%; $IC_{50}$ = 8.2

-continued
PXN681-d2
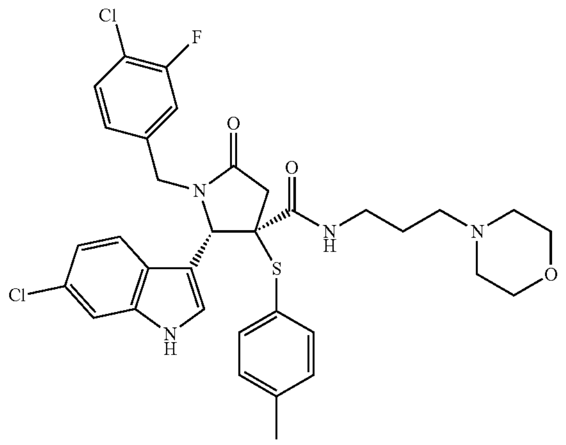
$C_{34}H_{35}Cl_2FN_4O_3S$; MW: 669.65; found (HPLC MS): $[M + H^+]$ = 669.0; Yield: 4%; $IC_{50}$ = 11.8
PXN681-d1
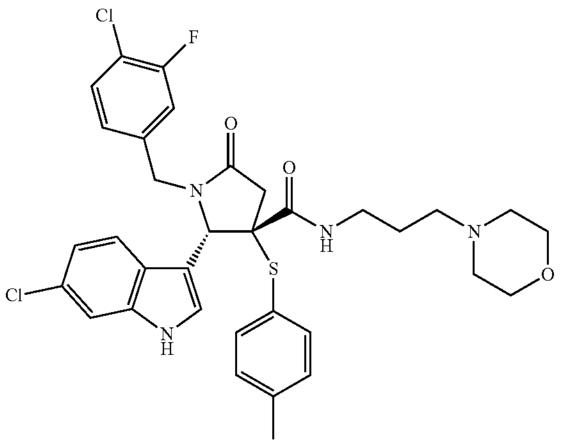
$C_{34}H_{35}Cl_2FN_4O_3S$; MW: 669.65; found (HPLC MS): $[M + H^+]$ = 669.1; Yield: 15%; $IC_{50}$ = 9.5
PXN682-d2
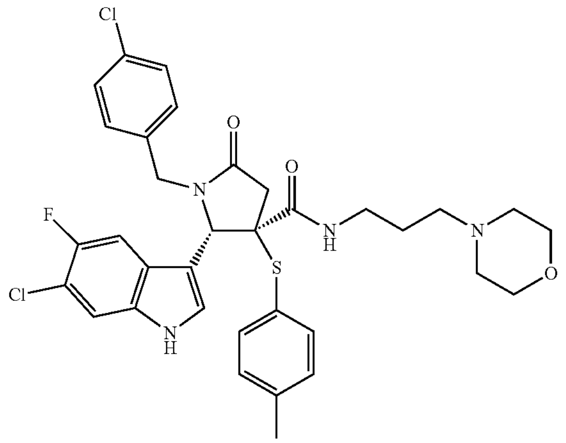
$C_{34}H_{35}Cl_2FN_4O_3S$; MW: 669.65; found (HPLC MS): $[M + H^+]$ = 669.1; Yield: 1%; $IC_{50}$ = 16.2
PXN682-d1
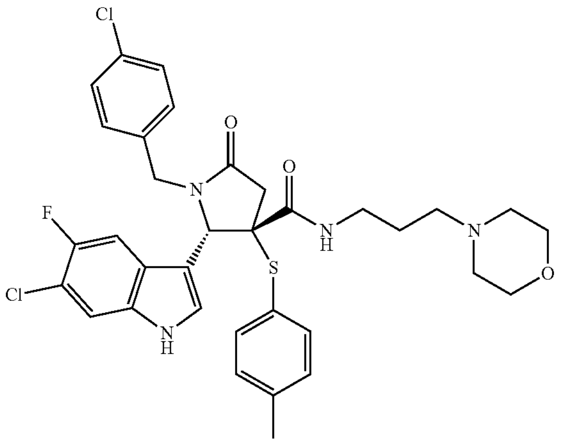
$C_{34}H_{35}Cl_2FN_4O_3S$; MW: 669.65; found (HPLC MS): $[M + H^+]$ = 669.1; Yield: 5%; $IC_{50}$ = 8.6
PXN683-d1
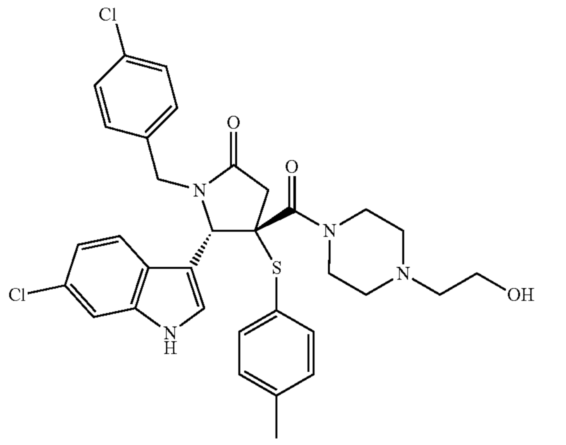
$C_{33}H_{34}Cl_2N_4O_3S$; MW: 637.63; found (HPLC MS): $[M + H^+]$ = 637.0; Yield: 8%; $IC_{50}$ = 6.0
PXN684
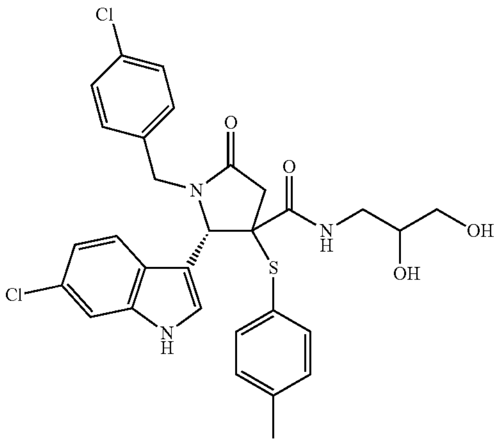
$C_{30}H_{29}Cl_2N_3O_4S$; MW: 598.55; found (HPLC MS): $[M + H^+]$ = 598.2; Yield: 7%; $IC_{50}$ = 5.7

-continued
PXN686-d1
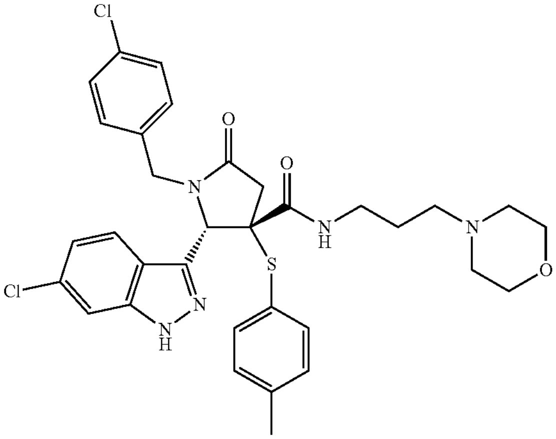
$C_{33}H_{35}Cl_2N_5O_3S$; MW: 652.65; found (HPLC MS): [M + H$^+$] = 652.0; Yield: 6%; $IC_{50}$ = 6.8
PXN687
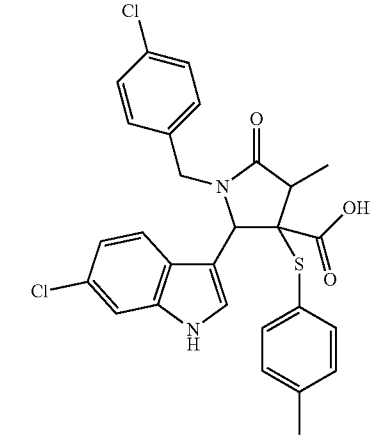
$C_{28}H_{24}Cl_2N_2O_3S$; MW: 539.49; found (HPLC MS): [M + H$^+$] = 539.1
PXN688
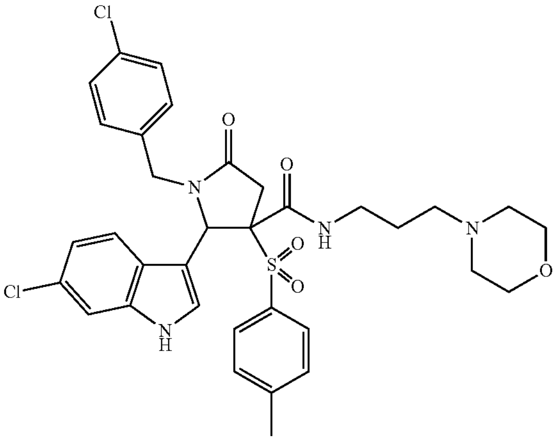
$C_{34}H_{36}Cl_2N_4O_5S$; MW: 683.66; found (HPLC MS): [M + H$^+$] = 683.1; Yield: 5%; $IC_{50}$ >60
PXN689-d1
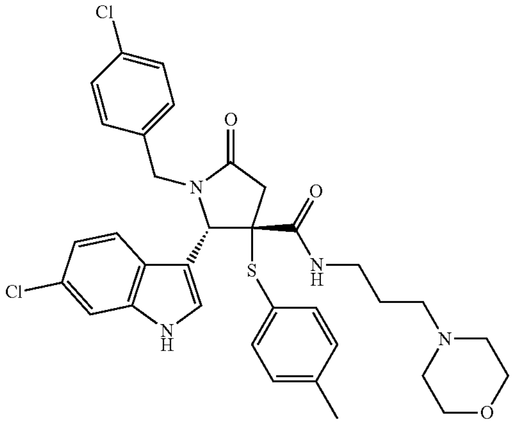
$C_{34}H_{36}Cl_2N_4O_3S$; MW: 651.66; found (HPLC MS): [M + H$^+$] = 651.1; Yield: 8%; $IC_{50}$ = 8.6
PXN690
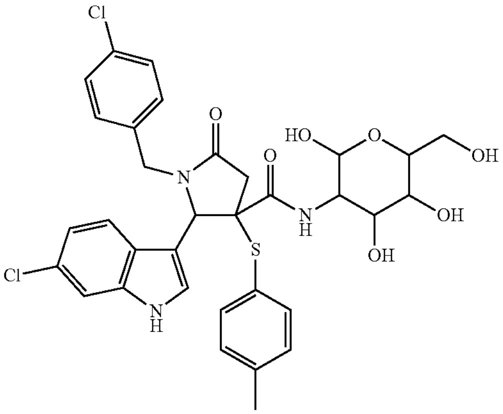
$C_{33}H_{33}Cl_2N_3O_7S$; MW: 686.62; found (HPLC MS): [M + Na$^+$] = 710.1; Yield: 9%; $IC_{50}$ = 33.8
PXN691
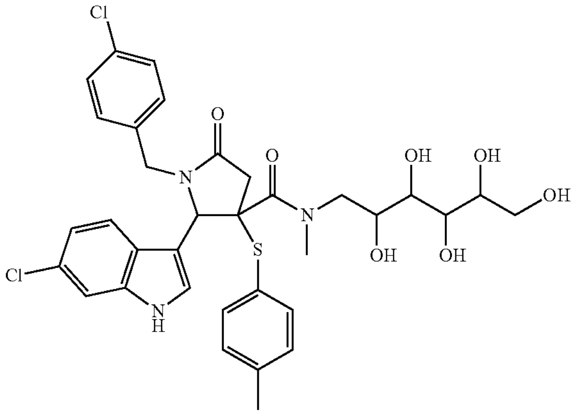
$C_{34}H_{37}Cl_2N_3O_7S$; MW: 702.66; found (HPLC MS): [M + H$^+$] = 702.3; [M + Na$^+$] = 724.1; Yield: 4%; $IC_{50}$ = 17.6

-continued
PXN693-d1
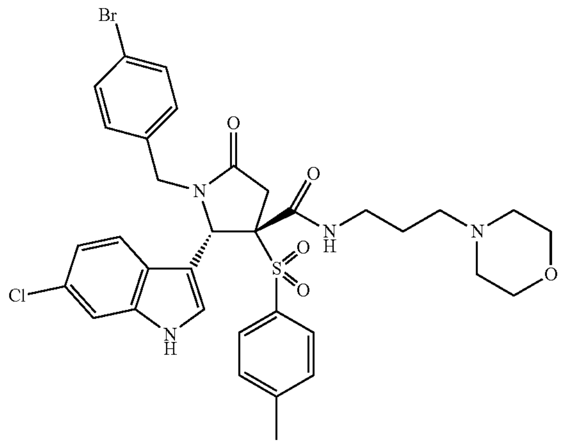
$C_{34}H_{36}BrClN_4O_5S$; MW: 728.11; found (HPLC MS): $[M + H^+]$ = 729.1; Yield: 4%
PXN694-d1
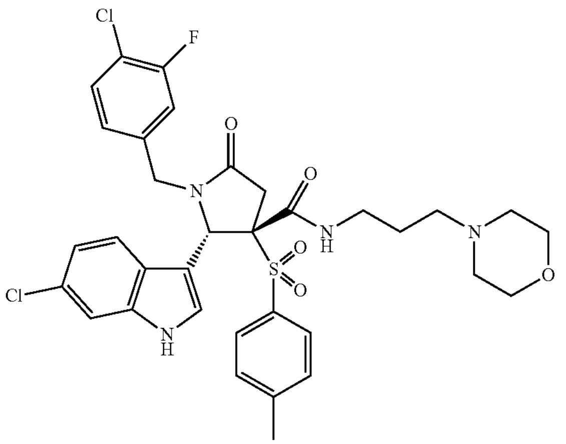
$C_{34}H_{35}Cl_2FN_4O_5S$; MW: 701.65; found (HPLC MS): $[M + H^+]$ = 703.1; Yield: 7%
PXN695-d1
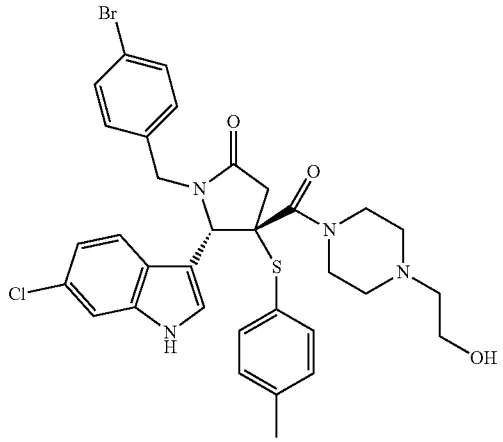
$C_{33}H_{34}BrClN_4O_3S$; MW: 682.08; found (HPLC MS): $[M + H^+]$ = 683.0; Yield: 5%; $IC_{50}$ = 5.4
PXN696-d1
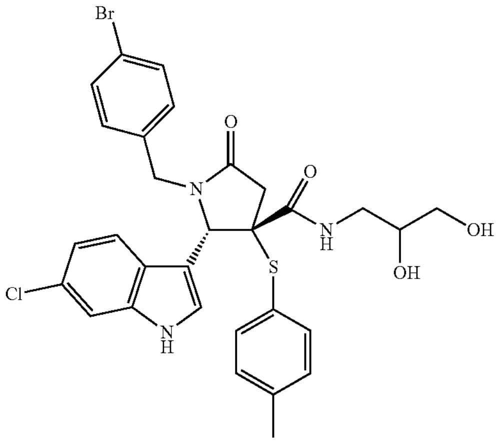
$C_{30}H_{29}BrClN_3O_4S$; MW: 643.00; found (HPLC MS): $[M + H^+]$ = 668.1; Yield: 7%; $IC_{50}$ = 4.1
PXN697-d1
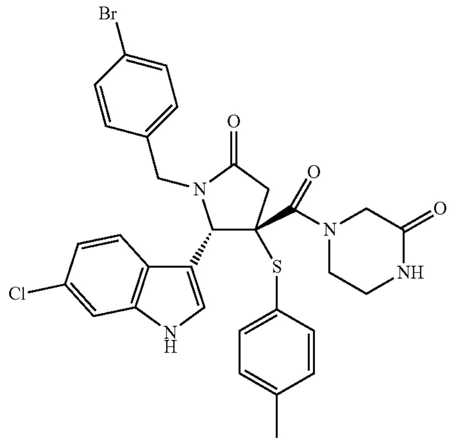
$C_{31}H_{28}BrClN_4O_3S$; MW: 652.01; found (HPLC MS): $[M + H^+]$ = 653.1; $[M + Na^+]$ = 675.3; Yield: 3%; $IC_{50}$ = 3.6
PXN698-d1
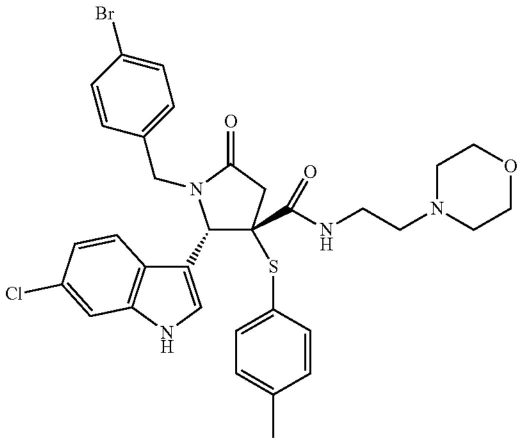
$C_{33}H_{34}BrClN_4O_3S$; MW: 682.08; found (HPLC MS): $[M + H^+]$ = 683.1; Yield: 7%; $IC_{50}$ = 6.3

-continued
PXN699-d1
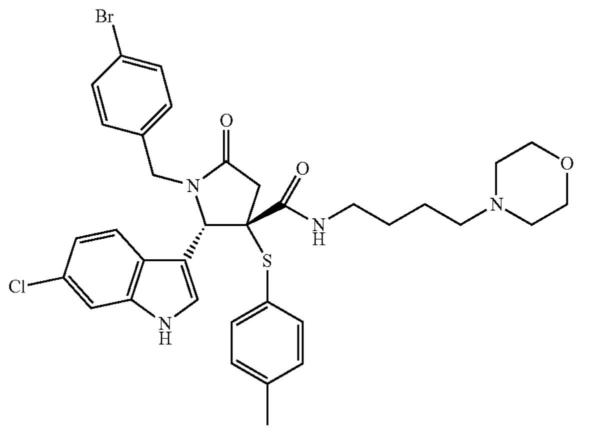
$C_{35}H_{38}BrClN_4O_3S$; MW: 710.14; found (HPLC MS): $[M + H^+]$ = 711.0; Yield: 7%; $IC_{50}$ = 4.2
PXN700-d1
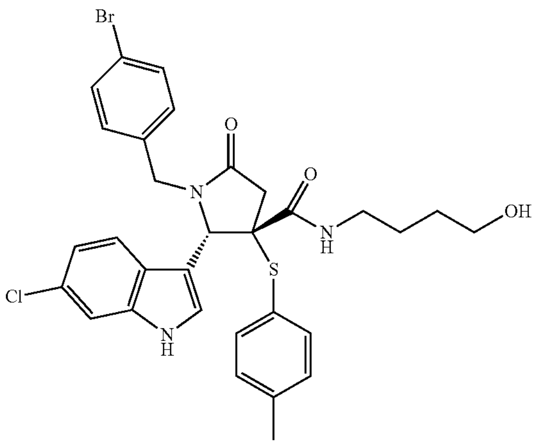
$C_{31}H_{31}BrClN_3O_3S$; MW: 641.03; found (HPLC MS): $[M + Na^+]$ = 664.2; Yield: 7%; $IC_{50}$ = 4.3
PXN701-d1
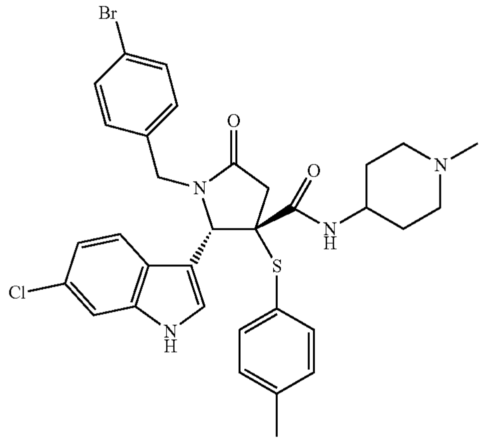
$C_{33}H_{34}BrClN_4O_2S$; MW: 666.09; found (HPLC MS): $[M + H^+]$ = 668.2; Yield: 8%; $IC_{50}$ = 4.1
PXN702-d1
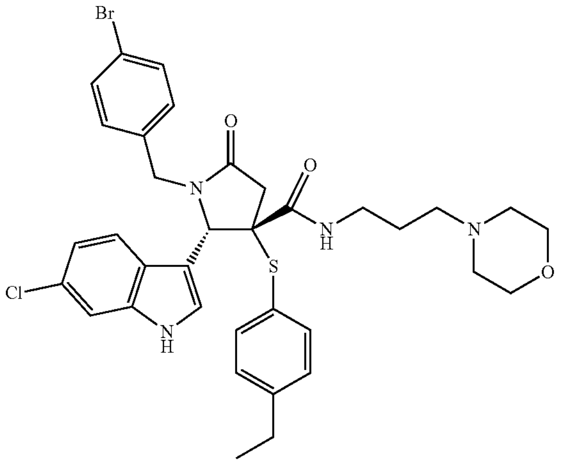
$C_{35}H_{38}BrClN_4O_3S$; MW: 710.14; found (HPLC MS): $[M + H^+]$ = 711.1; Yield: 17%; $IC_{50}$ = 18.6
PXN703-d1
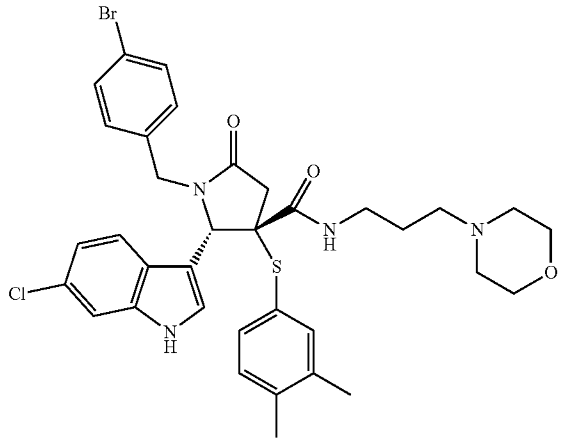
$C_{35}H_{38}BrClN_4O_3S$; MW: 710.14; found (HPLC MS): $[M + H^+]$ = 711.0; Yield: 10%; $IC_{50}$ = 9.5
PXN704-d1
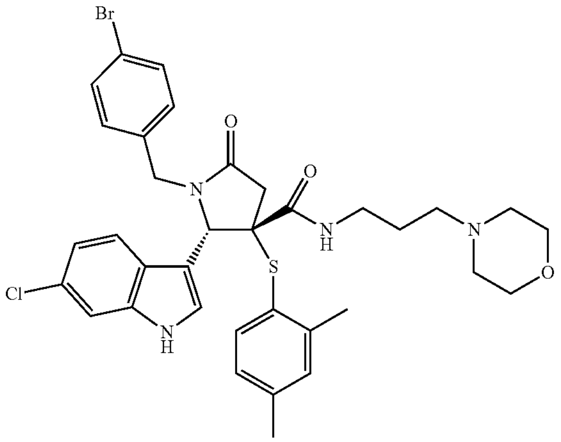
$C_{35}H_{38}BrClN_4O_3S$; MW: 710.14; found (HPLC MS): $[M + H^+]$ = 711.0; Yield: 6%; $IC_{50}$ = 11.7

-continued

PXN705-d1

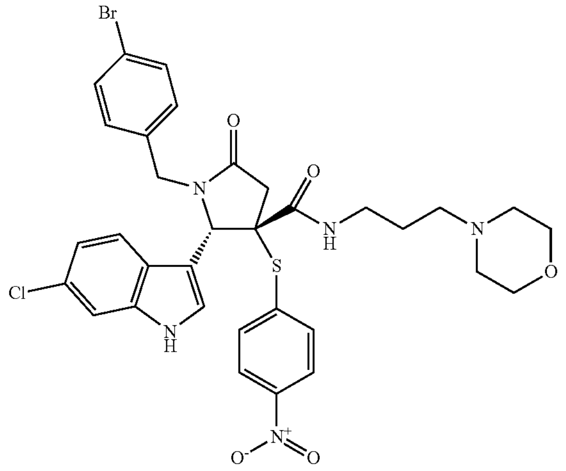

$C_{33}H_{33}BrClN_5O_5S$; MW: 727.08; found (HPLC MS): [M + H$^+$] = 727.9; Yield: 1%; $IC_{50}$ = 16.4

PXN706-d1

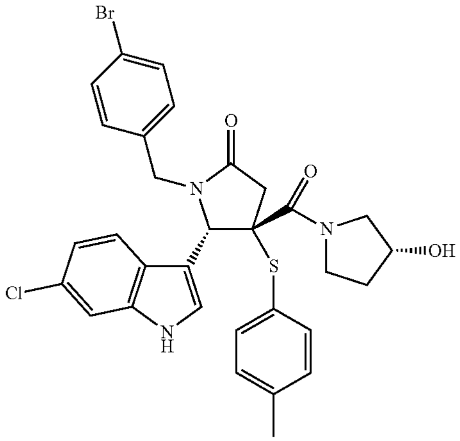

$C_{31}H_{29}BrClN_3O_3S$; MW: 639.02; found (HPLC MS): [M + H$^+$] = 640.3; [M + Na$^+$] = 662.3; Yield: 8%; $IC_{50}$ = 4.7

PXN707-d1

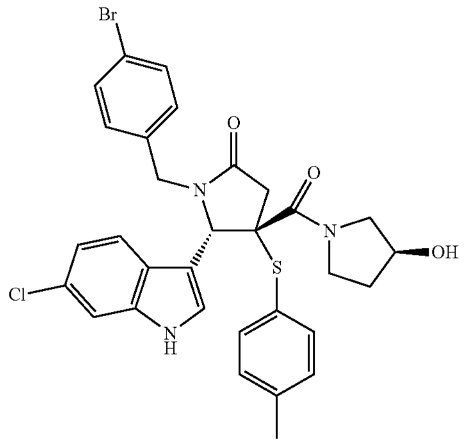

$C_{31}H_{29}BrClN_3O_3S$; MW: 639.02; found (HPLC MS): [M + H$^+$] = 640.3; [M + Na$^+$] = 662.3; Yield: 11%; $IC_{50}$ = 5.4

PXN708-d1

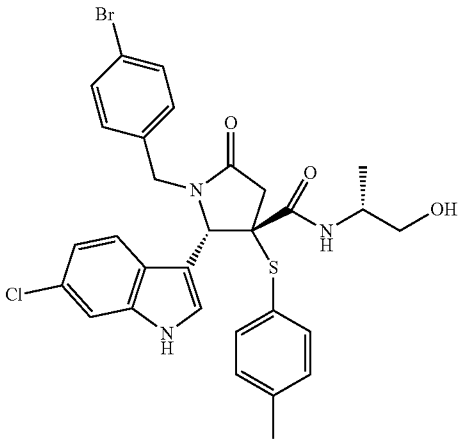

$C_{30}H_{29}BrClN_3O_3S$; MW: 627.00; found (HPLC MS): [M + Na$^+$] = 650.6; Yield: 8%; $IC_{50}$ = 6.1

PXN709-d1

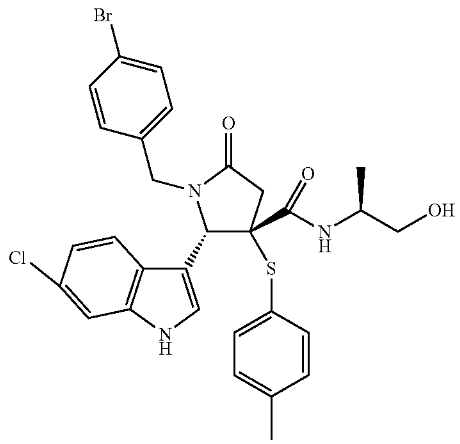

$C_{30}H_{29}BrClN_3O_3S$; MW: 627.00; found (HPLC MS): [M + Na$^+$] = 650.2; Yield: 8%; $IC_{50}$ = 7.4

PXN705-d2

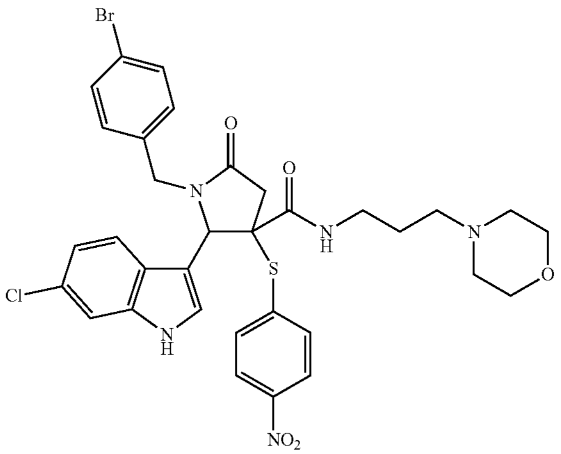

$C_{33}H_{33}BrClN_5O_5S$; MW: 727.08; found (HPLC MS): [M + H$^+$] = 726.0; Yield: 3%; $IC_{50}$ = 9.5

-continued
PXN710
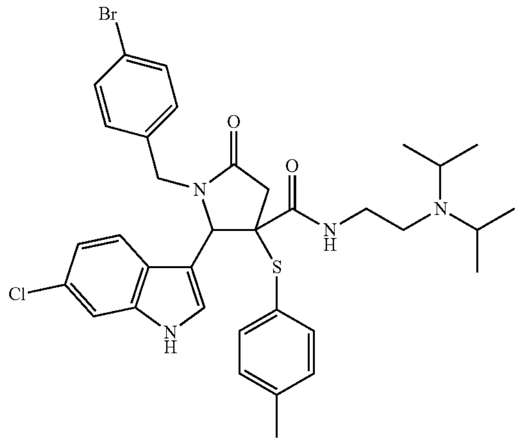
$C_{35}H_{40}BrClN_4O_2S$; MW: 696.16; found (HPLC MS): $[M + H^+]$ = 697.3; Yield: 6%
PXN711-d1
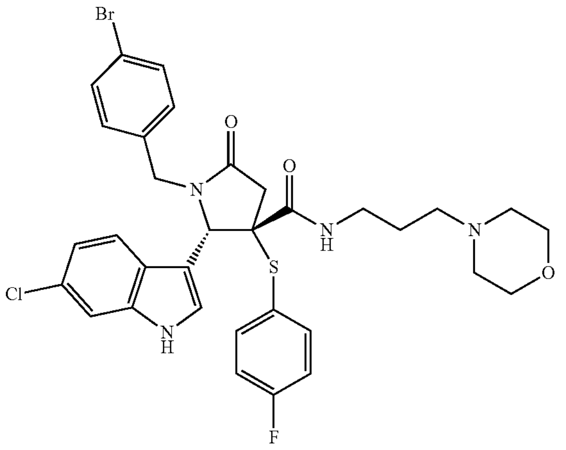
$C_{33}H_{33}BrClFN_4O_3S$; MW: 700.08; found (HPLC MS): $[M + H^+]$ = 701.2; Yield: 3%; $IC_{50}$ = 7.3
PXN712-d1
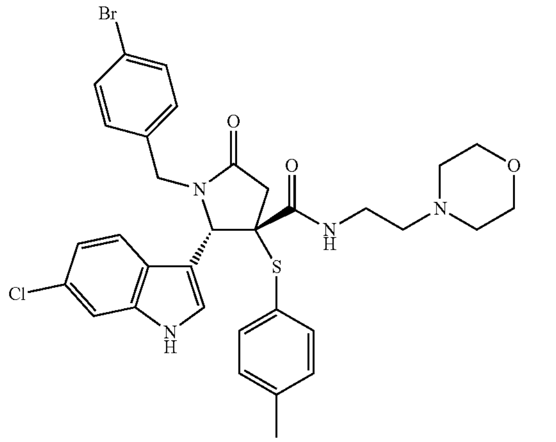
$C_{33}H_{34}BrClN_4O_3S$; MW: 682.08; found (HPLC MS): $[M + H^+]$ = 683.1; Yield: 6%
PXN713-d1
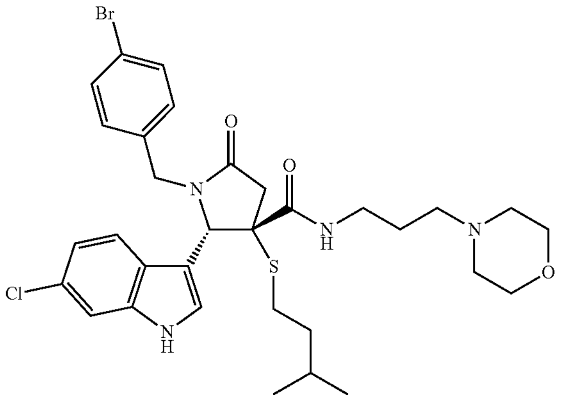
$C_{32}H_{40}BrClN_4O_3S$; MW: 676.12; found (HPLC MS): $[M + H^+]$ = 677.2; Yield: 4%; $IC_{50}$ = 8.1
PXN714-d1
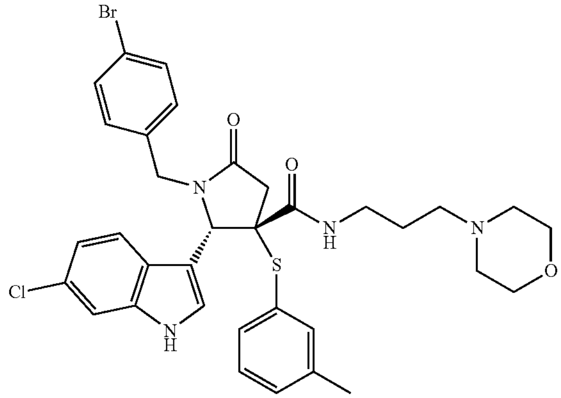
$C_{34}H_{36}BrClN_4O_3S$; MW: 696.11; found (HPLC MS): $[M + H^+]$ = 697.2; Yield: 2%; $IC_{50}$ = 6.8
PXN715-d1
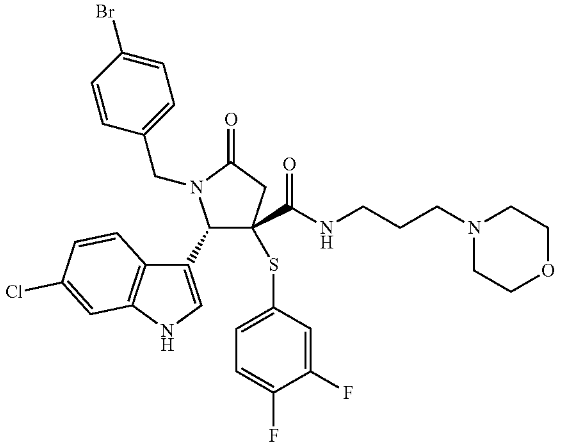
$C_{33}H_{32}BrClF_2N_4O_3S$; MW: 718.07; found (HPLC MS): $[M + H^+]$ = 719.2; Yield: 4%; $IC_{50}$ = 7.9

-continued

PXN716-d1

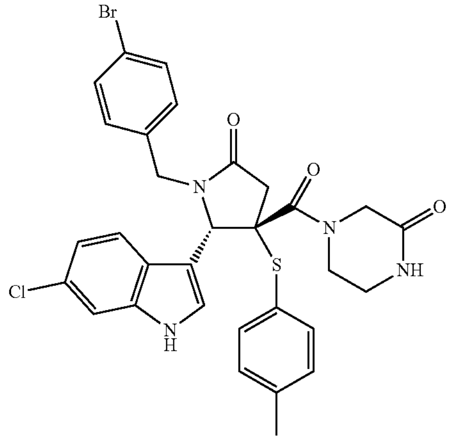

$C_{31}H_{28}BrClN_4O_3S$; MW: 652.01; found (HPLC MS): $[M + H^+] = 653.1$; $[M + Na^+] = 675.3$; Yield: 4%

PXN717-d1

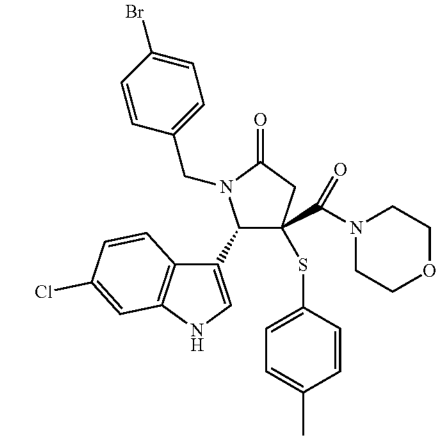

$C_{31}H_{29}BrClN_3O_3S$; MW: 639.02; found (HPLC MS): $[M + H^+] = 640.2$; $[M + Na^+] = 662.1$; Yield: 10%; $IC_{50} = 8.9$ PXN718-d1

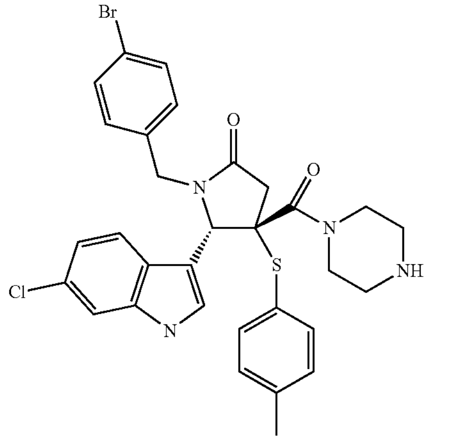

$C_{31}H_{30}BrClN_4O_2S$; MW: 638.03; found (HPLC MS): $[M + H^+] = 639.2$; Yield: 9%; $IC_{50} = 3.5$ PXN719-d1

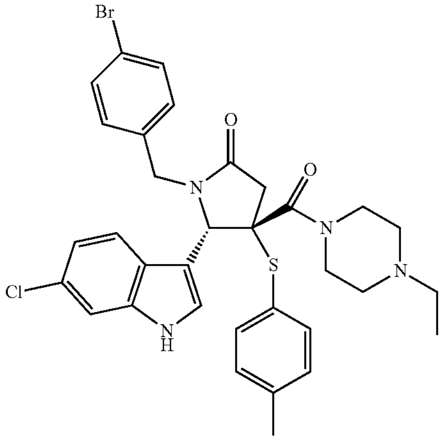

$C_{33}H_{34}BrClN_4O_2S$; MW: 666.09; found (HPLC MS): $[M + H^+] = 665.4$; Yield: 8%; $IC_{50} = 8.2$ PXN720-d1

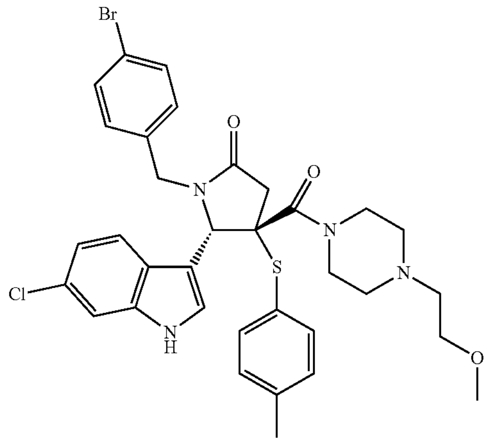

$C_{34}H_{36}BrClN_4O_3S$; MW: 696.11; found (HPLC MS): $[M + H^+] = 695.4$; Yield: 5%; $IC_{50} = 6.6$ PXN721-d1

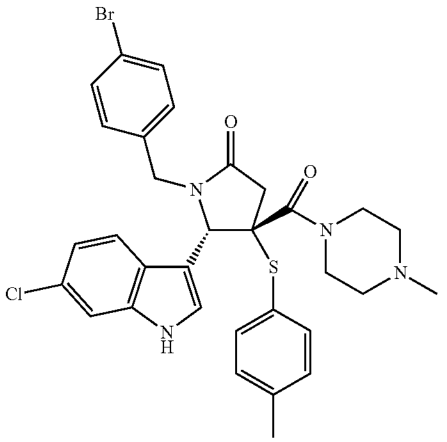

$C_{32}H_{32}BrClN_4O_2S$; MW: 652.06; found (HPLC MS): $[M + H^+] = 651.4$; Yield: 5%; $IC_{50} = 7.2$ -continued
PXN722-d1
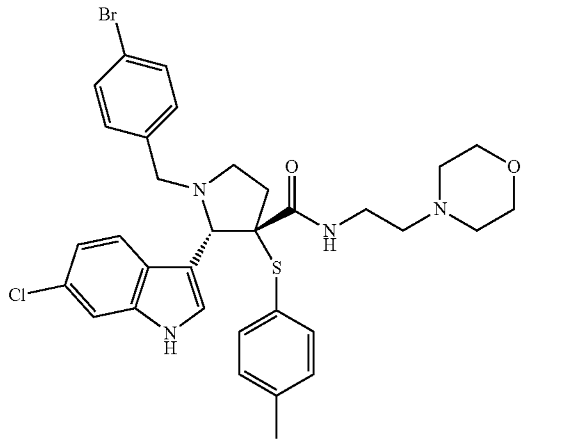
$C_{33}H_{36}BrClN_4O_2S$; MW: 668.10; found (HPLC MS): $[M + H^+]$ = 667.3; Yield: 2%; $IC_{50}$ = 13.2
PXN725-d1
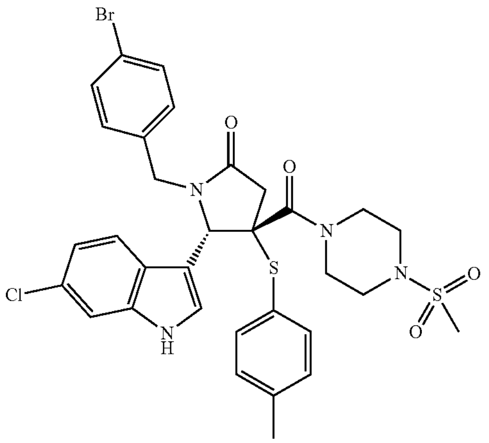
$C_{32}H_{32}BrClN_4O_4S_2$; MW: 716.12; found (HPLC MS): $[M + Na^+]$ = 737.2; Yield: 5%; $IC_{50}$ > 60
PXN726-d1
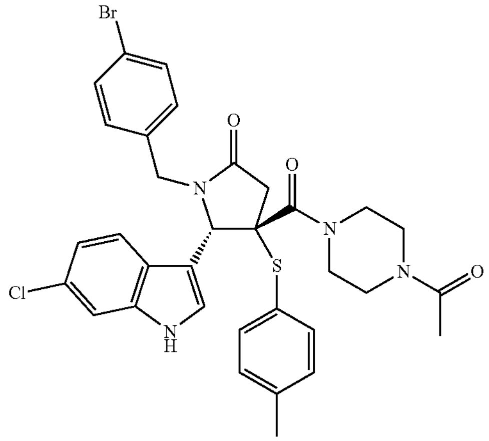
$C_{33}H_{32}BrClN_4O_3S$; MW: 680.07; found (HPLC MS): $[M + H^+]$ = 681.1; $[M + Na^+]$ = 703.2; Yield: 9%; $IC_{50}$ = 2.1
PXN727-d1
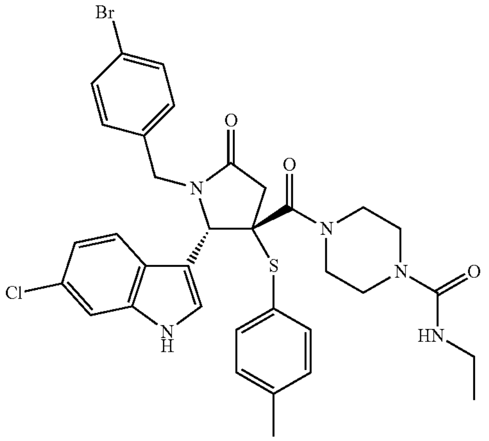
$C_{34}H_{35}BrClN_5O_3S$; MW: 709.11; found (HPLC MS): $[M + H^+]$ = 710.0; $[M + Na^+]$ = 732.2; Yield: 11%; $IC_{50}$ = 1.4
PXN728-d1
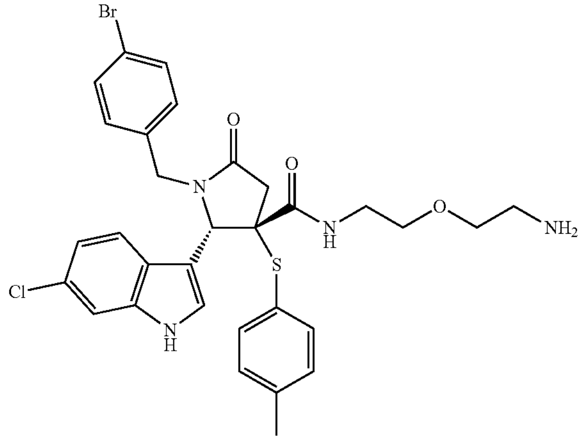
$C_{31}H_{32}BrClN_4O_3S$; MW: 656.05; found (HPLC MS): $[M + H^+]$ = 657.2; Yield: 4%

-continued
PXN729
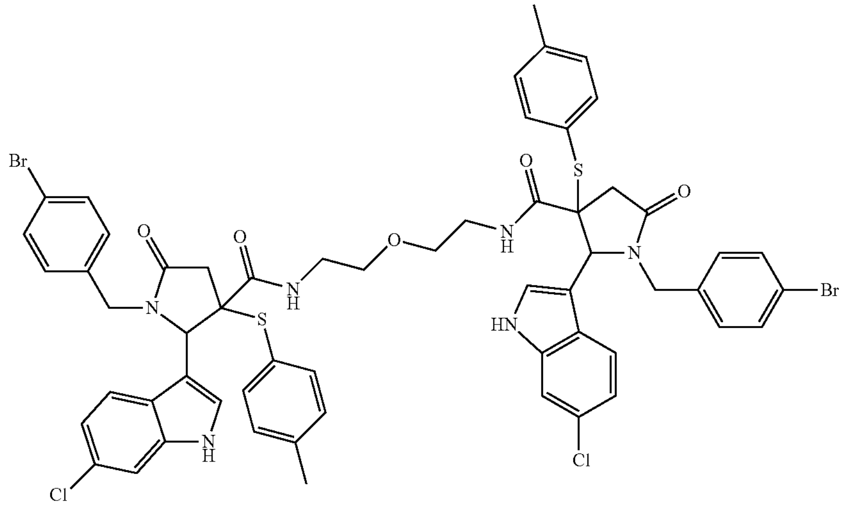
$C_{58}H_{52}Br_2Cl_2N_6O_5S_2$; MW: 1207.94; found (HPLC MS): $[M + Na^+] = 1229.5$; Yield: 10%
PXN730-d1
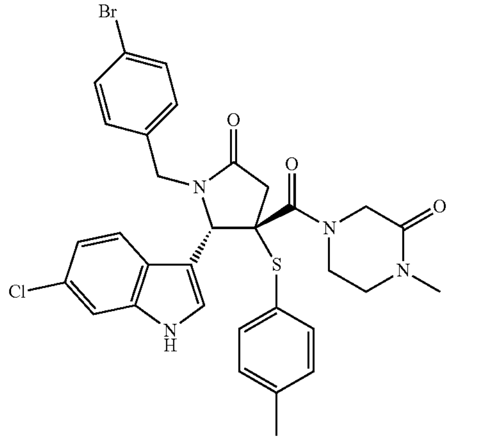
$C_{32}H_{30}BrClN_4O_3S$; MW: 666.04; found (HPLC MS): $[M + H^+] = 666.9$; $[M + Na^+] = 689.0$; Yield: 6%; $IC_{50} = 4.8$
PXN731-d1
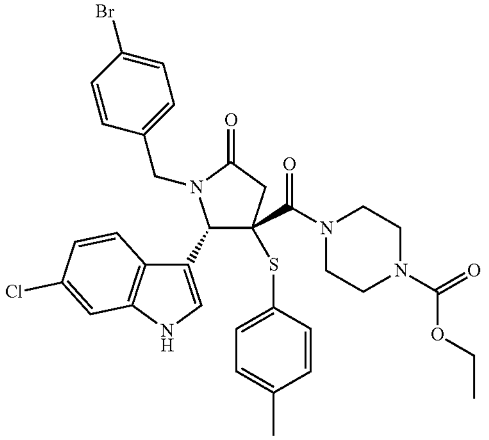
$C_{34}H_{34}BrClN_4O_4S$; MW: 710.10; found (HPLC MS): $[M + H^+] = 711.5$; $[M + Na^+] = 733.5$; Yield: 4%; $IC_{50} = 118.7$
PXN732-d1
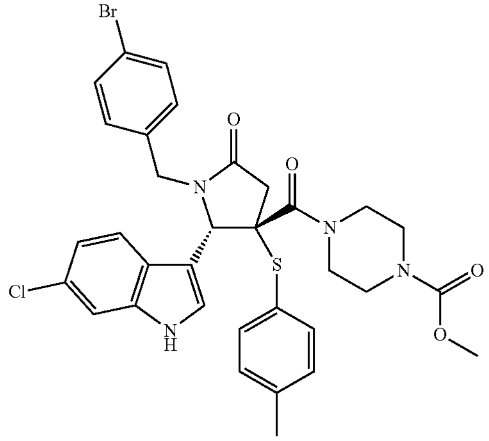
$C_{33}H_{32}BrClN_4O_4S$; MW: 696.07; found (HPLC MS): $[M + H^+] = 697.4$; $[M + Na^+] = 719.4$; Yield: 4%; $IC_{50} = 2.1$
PXN733-d1
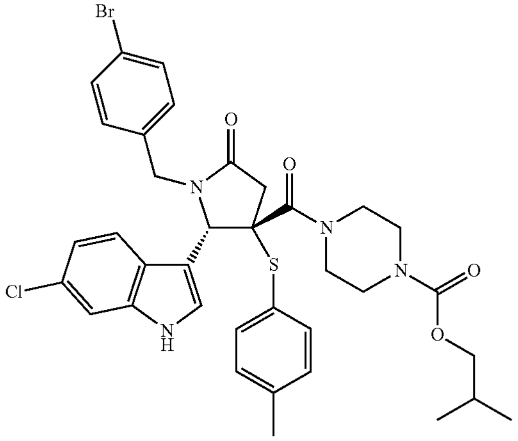
$C_{36}H_{38}BrClN_4O_4S$; MW: 738.15; found (HPLC MS): $[M + H^+] = 739.1$; $[M + Na^+] = 759.5$; Yield: 4%

-continued
PXN734-d1
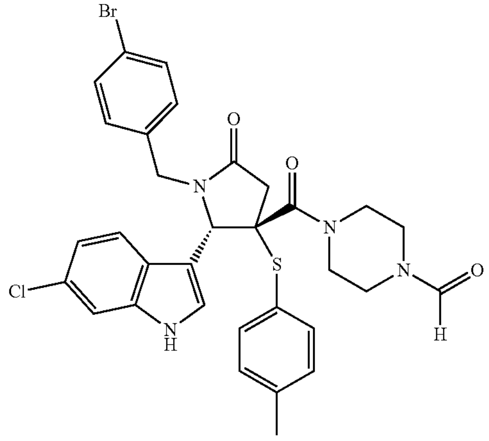
$C_{32}H_{30}BrClN_4O_3S$; MW: 666.04
PXN735-d1
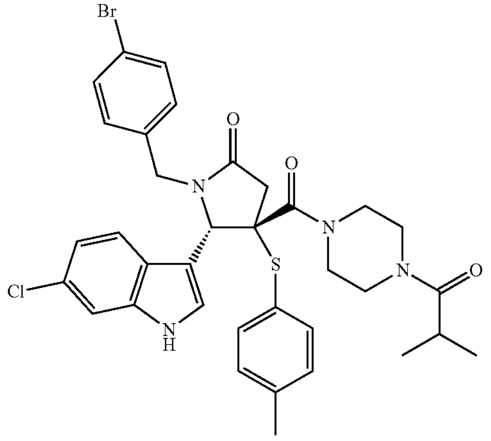
$C_{35}H_{36}BrClN_4O_3S$; MW: 708.12; found (HPLC MS): $[M + H^+] = 711.0$; $[M + Na^+] = 731.0$; Yield: 8%; $IC_{50} = 3.4$
PXN736-d1
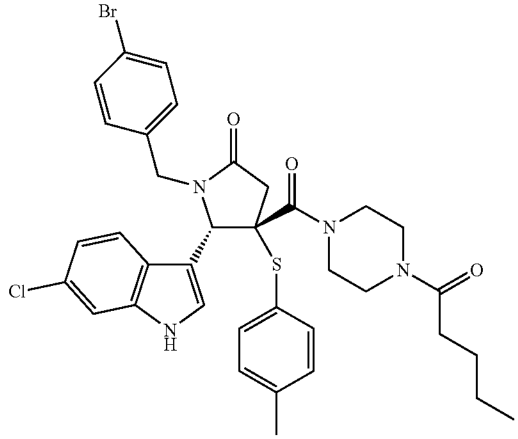
$C_{36}H_{38}BrClN_4O_3S$; MW: 722.15; found (HPLC MS): $[M + H^+] = 723.4$; $[M + Na^+] = 745.4$; Yield: 7%; $IC_{50} > 60$
PXN737-d1
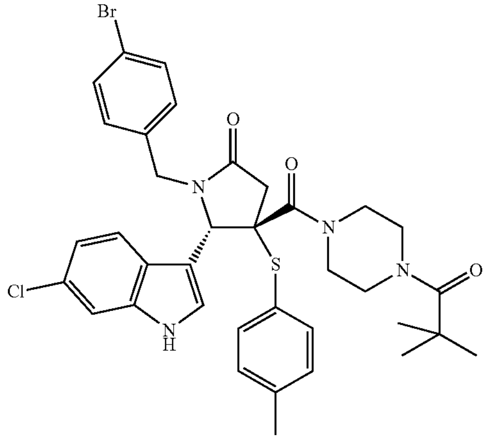
$C_{36}H_{38}BrClN_4O_3S$; MW: 722.15; found (HPLC MS): $[M + H^+] = 721.4$; $[M + Na^+] = 743.5$; Yield: 7%; $IC_{50} = 15.6$
PXN738-d1
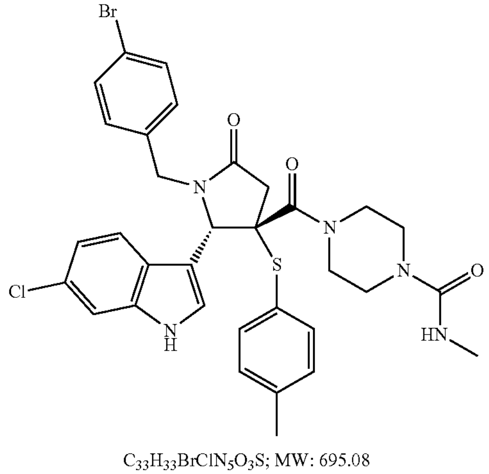
$C_{33}H_{33}BrClN_5O_3S$; MW: 695.08
PXN739-d1
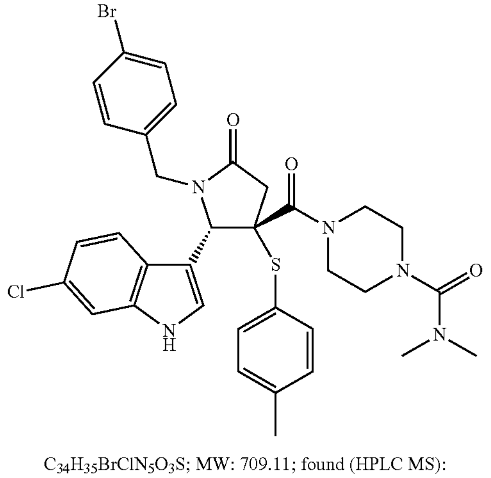
$C_{34}H_{35}BrClN_5O_3S$; MW: 709.11; found (HPLC MS): $[M + H^+] = 710.2$; Yield: 2%; $IC_{50} = 2.0$ -continued
PXN740-d1
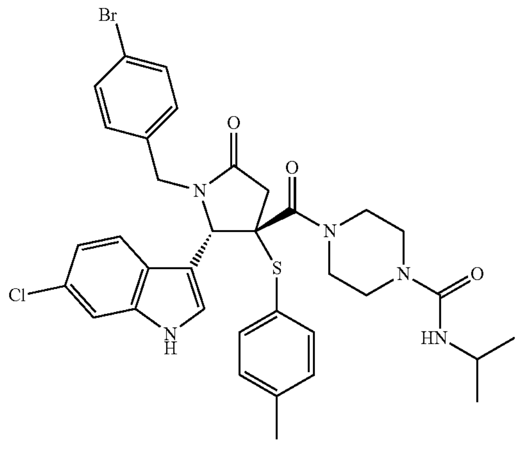
$C_{35}H_{37}BrClN_5O_3S$; MW: 723.14
PXN741-d1
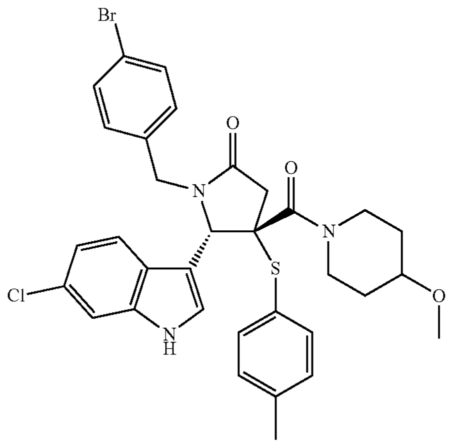
$C_{33}H_{33}BrClN_3O_3S$; MW: 667.07; found (HPLC MS): $[M + H^+] = 668.5$; $[M + Na^+] = 690.4$; Yield: 5%; $IC_{50} = 7.0$
PXN742-d1
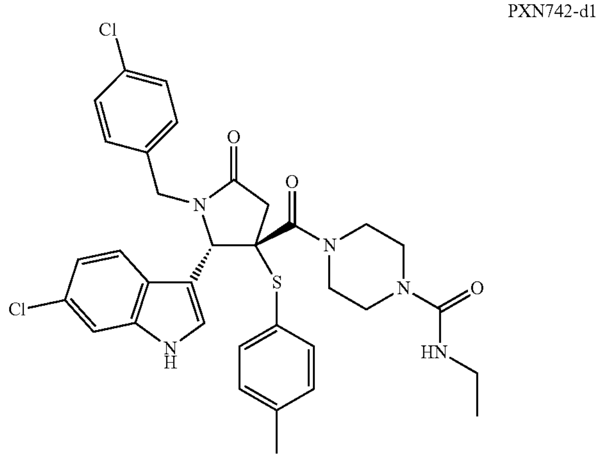
$C_{34}H_{35}Cl_2N_5O_3S$; MW: 664.66; found (HPLC MS): $[M + H^+] = 664.2$; $[M + Na^+] = 686.1$; Yield: 6%; $IC_{50} = 1.1$
PXN743-d1
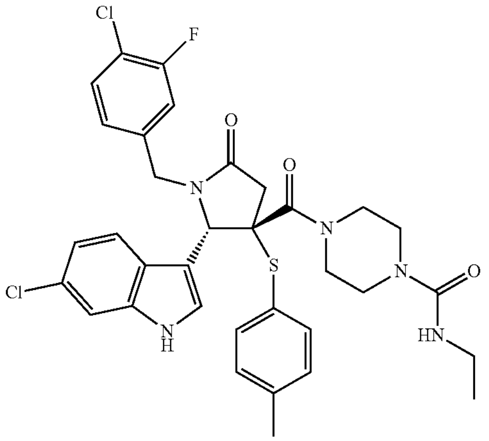
$C_{34}H_{34}Cl_2FN_5O_3S$; MW: 682.65; found (HPLC MS): $[M + H^+] = 682.7$; $[M + Na^+] = 704.2$; Yield: 6%; $IC_{50} = 1.5$
PXN744-d1
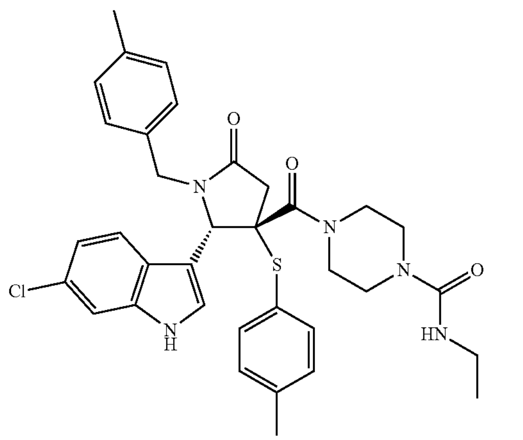
$C_{35}H_{38}ClN_5O_3S$; MW: 644.24; found (HPLC MS): $[M + H^+] = 644.4$; $[M + Na^+] = 666.3$; Yield: 5%; $IC_{50} = 107.1$
PXN745
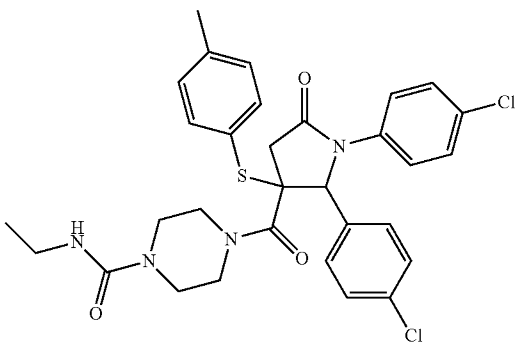
$C_{31}H_{32}Cl_2N_4O_3S$; MW: 611.60; found (HPLC MS): $[M + H^+] = 611.3$; $[M + Na^+] = 633.2$; Yield: 2%

-continued
PXN746
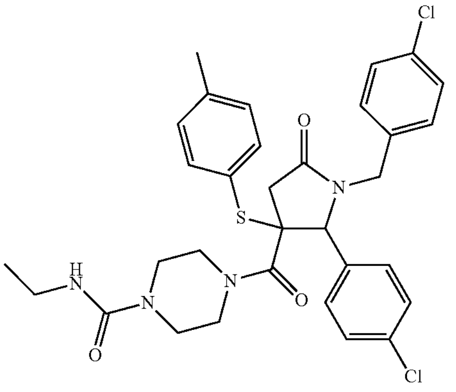
$C_{32}H_{34}Cl_2N_4O_3S$; MW: 625.62; found (HPLC MS): $[M+H^+]$ = 625.3; $[M+Na^+]$ = 649.3; Yield: 22%; $IC_{50}$ = 14.7
PXN747
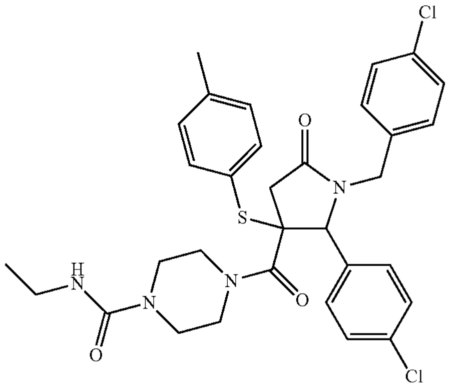
$C_{30}H_{31}Cl_2N_5O_3S$; MW: 612.58
PXN748-d1
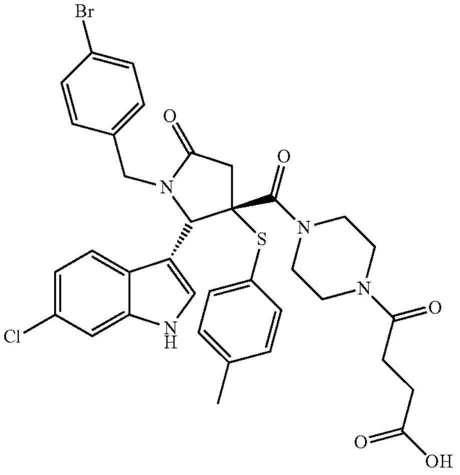
$C_{35}H_{34}BrClN_4O_5S$; MW: 738.11; found (HPLC MS): $[M+H^+]$ = 739.3; $[M+Na^+]$ = 762.1; Yield: 5%; $IC_{50}$ = 16.6
PXN749-d1
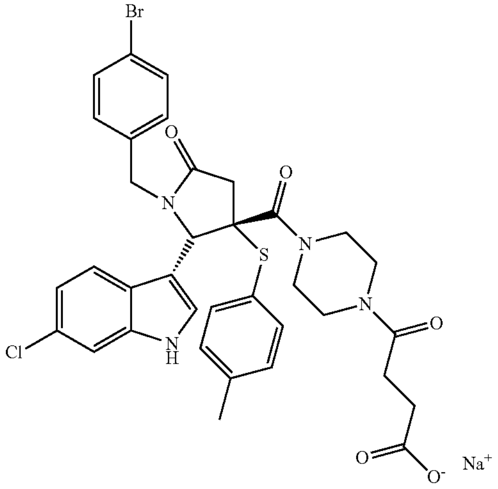
$C_{35}H_{33}BrClN_4NaO_5S$; MW: 760.09
PXN750-d1
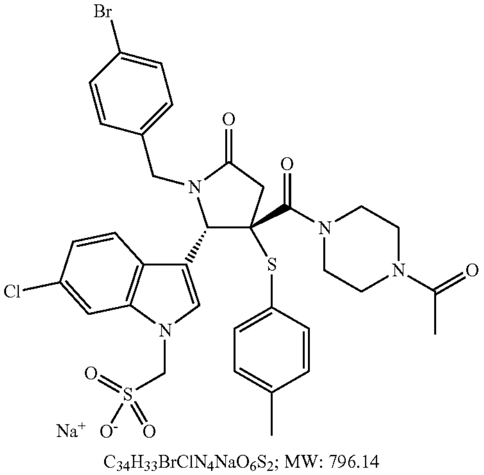
$C_{34}H_{33}BrClN_4NaO_6S_2$; MW: 796.14
PXN751-d1
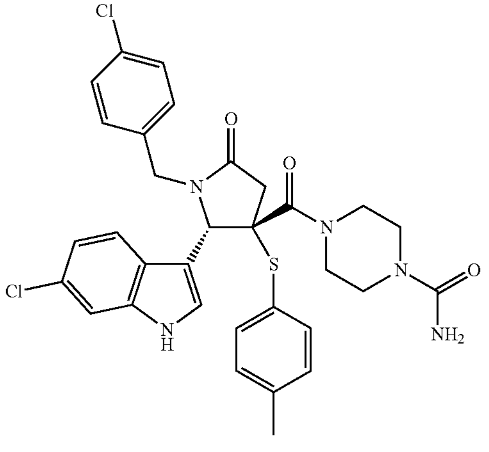
$C_{32}H_{31}Cl_2N_5O_3S$; MW: 636.61; found (HPLC MS): $[M+H^+]$ = 636.3; $[M+Na^+]$ = 658.2; Yield: 2%; $IC_{50}$ = 5.8

-continued

PXN752-d1

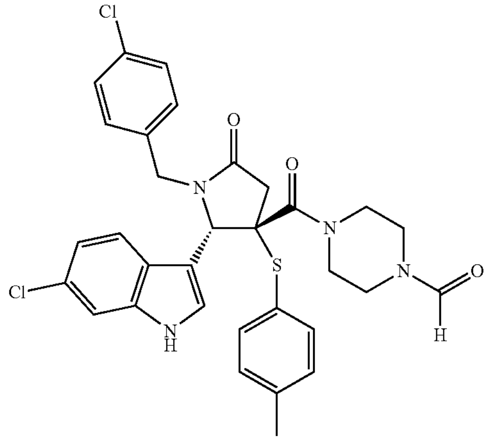

$C_{32}H_{30}Cl_2N_4O_3S$; MW: 621.59; found (HPLC MS): [M + H$^+$] = 621.1; Yield: 6%; $IC_{50}$ = 2.0

PXN753-d1

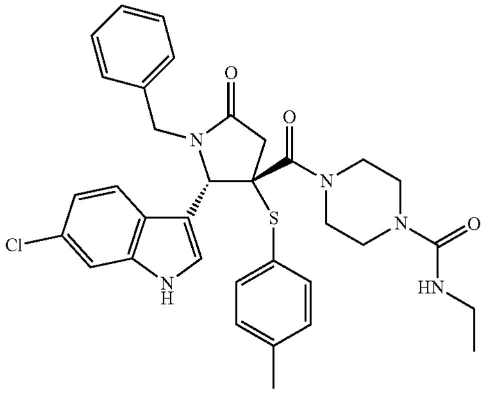

$C_{34}H_{36}ClN_5O_3S$; MW: 630.21; found (HPLC MS): [M + H$^+$] = 630.3; [M + Na$^+$] = 652.3; Yield: 5%; $IC_{50}$ = 170.6

PXN754-d1

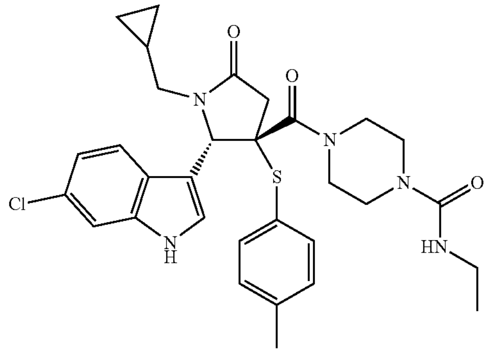

$C_{31}H_{36}ClN_5O_3S$; MW: 594.18; found (HPLC MS): [M + H$^+$] = 594.3; Yield: 12%; $IC_{50}$ = 13.6

PXN755-d1

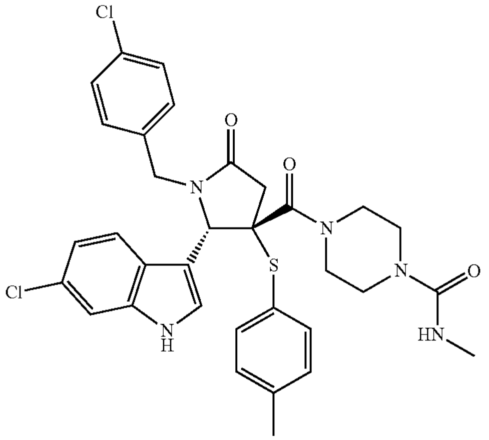

$C_{33}H_{33}Cl_2N_5O_3S$; MW: 650.63; found (HPLC MS): [M + H$^+$] = 650.1; [M + Na$^+$] = 672.3; Yield: 1%; $IC_{50}$ = 3.6

PXN756-d1

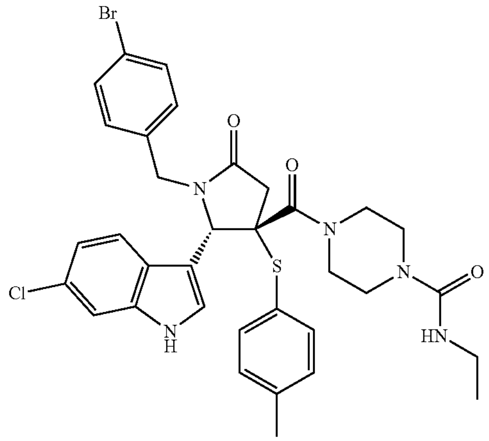

$C_{34}H_{35}BrClN_5O_3S$; MW: 709.11; found (HPLC MS): [M + H$^+$] = 710.0; [M + Na$^+$] = 732.2; Yield: 8%; $IC_{50}$ = 2.6

PXN757-d1

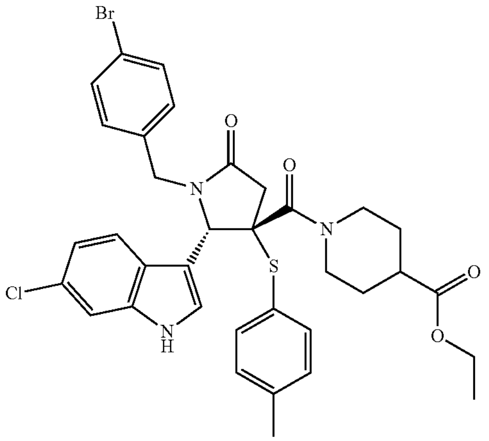

$C_{35}H_{35}BrClN_3O_4S$; MW: 709.11; found (HPLC MS): [M + Na$^+$] = 730.4; Yield: 12%; $IC_{50}$ = 206.1

-continued

PXN758-d1

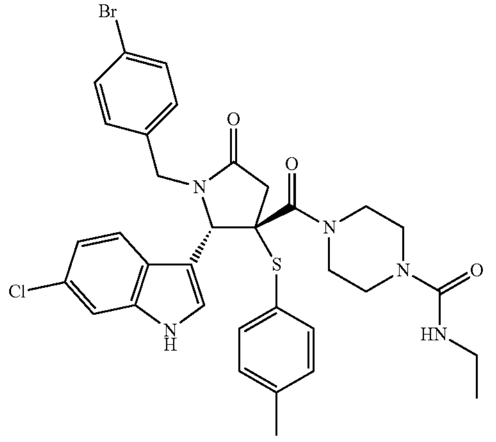

$C_{34}H_{35}BrClN_5O_3S$; MW: 709.11; found (HPLC MS): $[M + H^+] = 710.0$; $[M + Na^+] = 732.2$; Yield: 13%

PXN759-d1

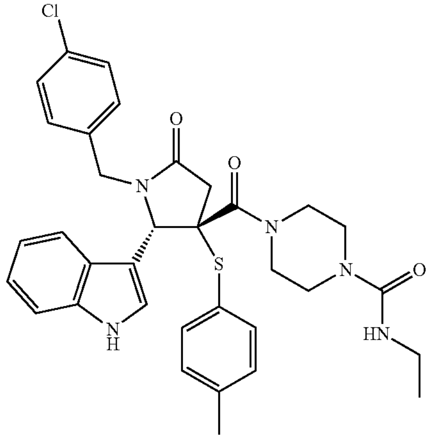

$C_{34}H_{36}ClN_5O_3S$; MW: 630.21; found (HPLC MS): $[M + H^+] = 630.2$; $[M + Na^+] = 652.3$; Yield: 6%; $IC_{50} = 182.6$ PXN760-d1

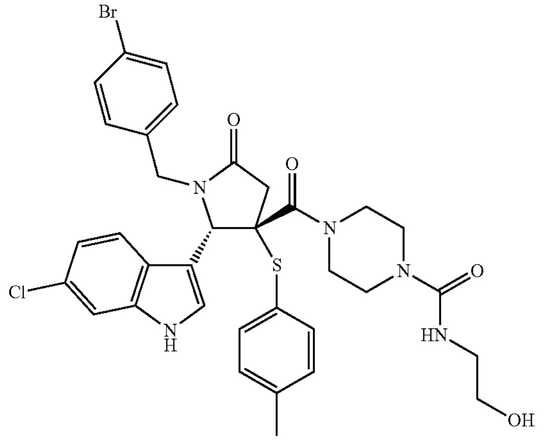

$C_{34}H_{35}BrClN_5O_4S$; MW: 725.11; found (HPLC MS): $[M + H^+] = 726.2$; $[M + Na^+] = 748.0$; Yield: 4%; $IC_{50} = 3.2$ PXN761-d1

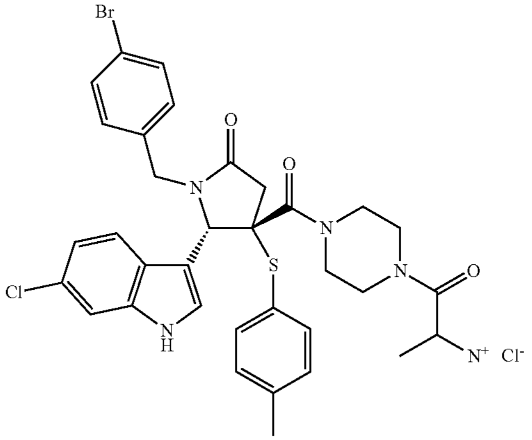

$C_{34}H_{36}BrCl_2N_5O_3S$; MW: 745.57; found (HPLC MS): $[M + H^+] = 708.1$; Yield: 10%; $IC_{50} = 3.1$ PXN762-d1

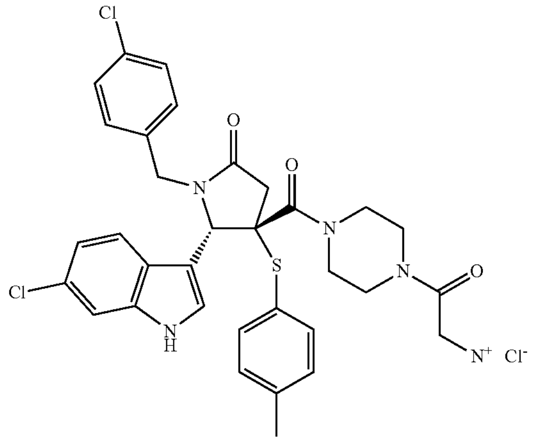

$C_{33}H_{34}Cl_3N_5O_3S$; MW: 687.09; found (HPLC MS): $[M + H^+] = 650.2$; Yield: 4%; $IC_{50} = 4.5$ PXN763-d1

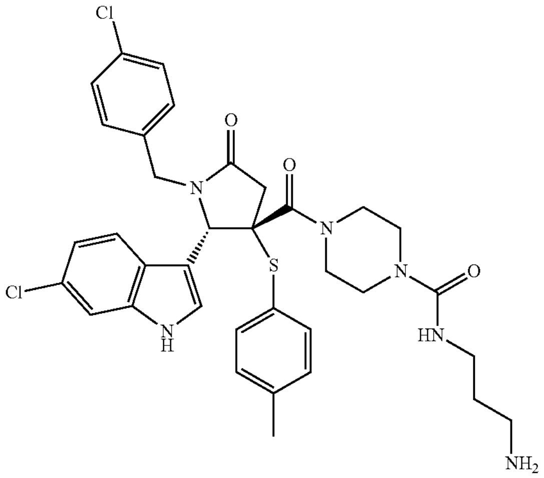

$C_{35}H_{38}Cl_2N_6O_3S$; MW: 693.70; found (HPLC MS): $[M + H^+] = 693.2$; Yield: 2%

-continued
PXN764-d1
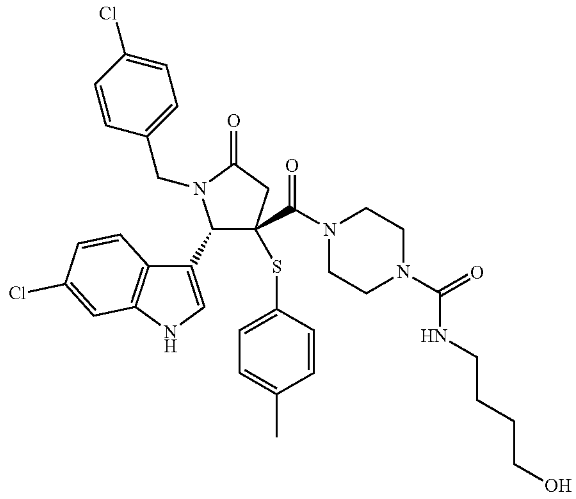
$C_{36}H_{39}Cl_2N_5O_4S$; MW: 708.71; found (HPLC MS): $[M + H^+]$ = 708.2; $[M + Na^+]$ = 730.2; Yield: 5%; $IC_{50}$ = 3.3
PXN765-d1
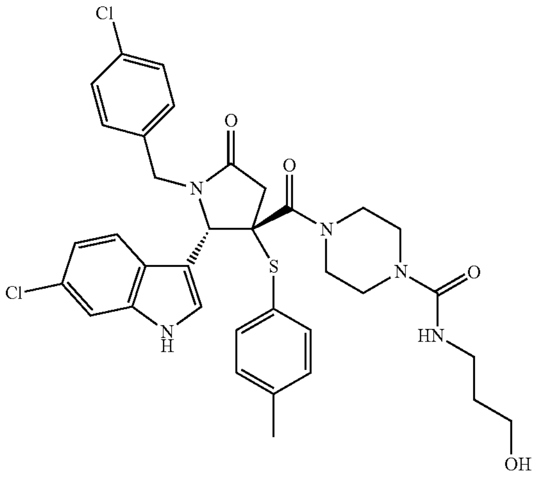
$C_{35}H_{37}Cl_2N_5O_4S$; MW: 694.69; found (HPLC MS): $[M + H^+]$ = 694.2; $[M + Na^+]$ = 716.3; Yield: 4%; $IC_{50}$ = 2.6
PXN766-d1
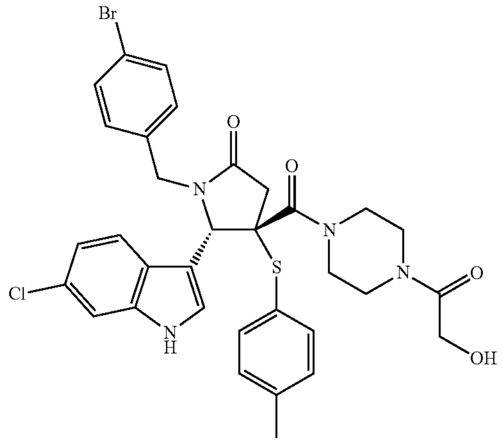
$C_{33}H_{32}BrClN_4O_4S$; MW: 696.07; found (HPLC MS): $[M + Na^+]$ = 717.2; Yield: 6%; $IC_{50}$ = 3.8
PXN767-d1
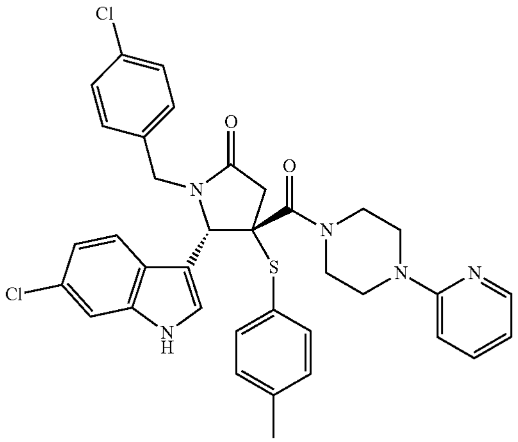
$C_{36}H_{33}Cl_2N_5O_2S$; MW: 670.67; found (HPLC MS): $[M + H^+]$ = 670.2; Yield: 9%; $IC_{50}$ > 60
PXN768-d1
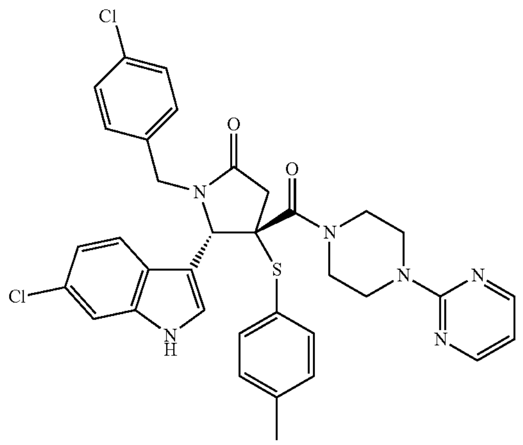
$C_{35}H_{32}Cl_2N_6O_2S$; MW: 671.65; found (HPLC MS): $[M + H^+]$ = 671.4; Yield: 6%; $IC_{50}$ = 118.7
PXN769-d1
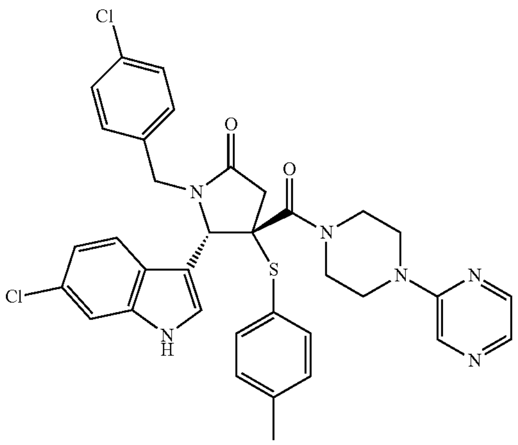
$C_{35}H_{32}Cl_2N_6O_2S$; MW: 671.65; found (HPLC MS): $[M + H^+]$ = 671.1; Yield: 8%; $IC_{50}$ >60

-continued
PXN770-d1
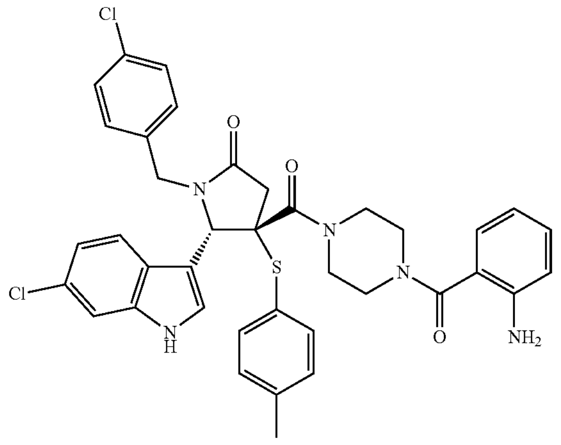
$C_{38}H_{35}Cl_2N_5O_3S$; MW: 712.70; found (HPLC MS): $[M + H^+]$ = 712.2; Yield: 5%; $IC_{50}$ = 191.7
PXN771-d1
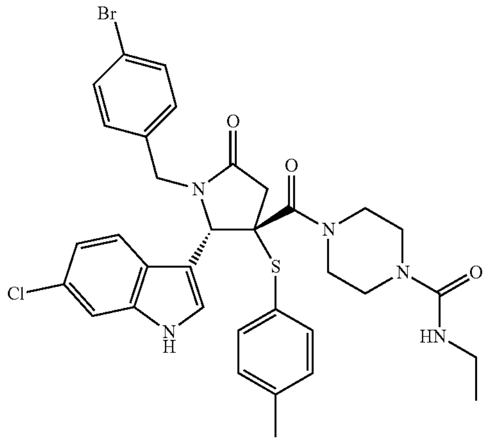
$C_{34}H_{35}BrClN_5O_3S$; MW: 709.11; found (HPLC MS): $[M + H^+]$ = 710.0; $[M + Na^+]$ = 732.2; Yield: 10%
PXN775-d1
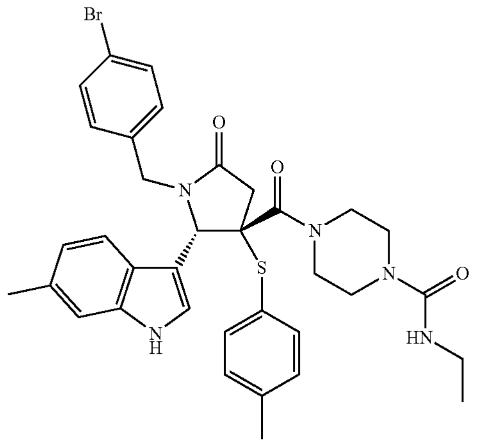
$C_{35}H_{38}BrN_5O_3S$; MW: 688.69; found (HPLC MS): $[M + H^+]$ = 690.2; Yield: 2%; CCA
PXN776-d1
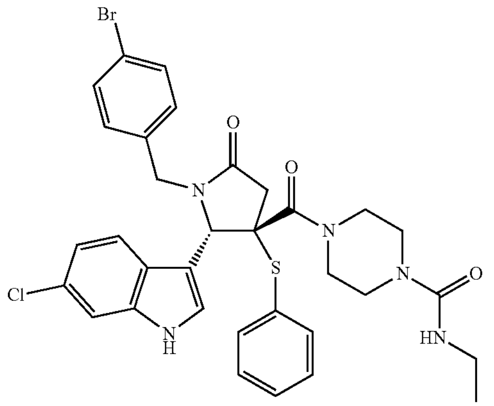
$C_{33}H_{33}BrClN_5O_3S$; MW: 695.08; found (HPLC MS): $[M + Na^+]$ = 716.1; Yield: 11%; $IC_{50}$ = 2.1
PXN777-d1
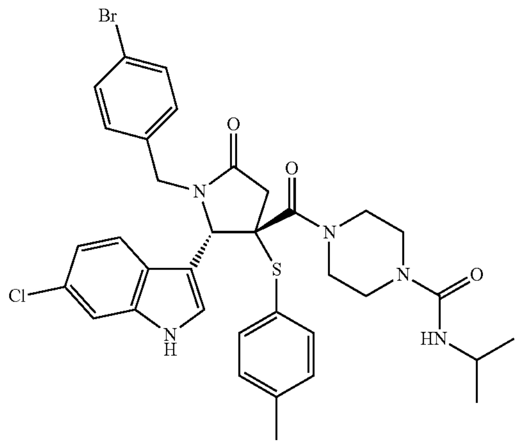
$C_{35}H_{37}BrClN_5O_3S$; MW: 723.14; found (HPLC MS): $[M + H^+]$ = 722.1; Yield: 10%; $IC_{50}$ = 5.5
PXN779-d1
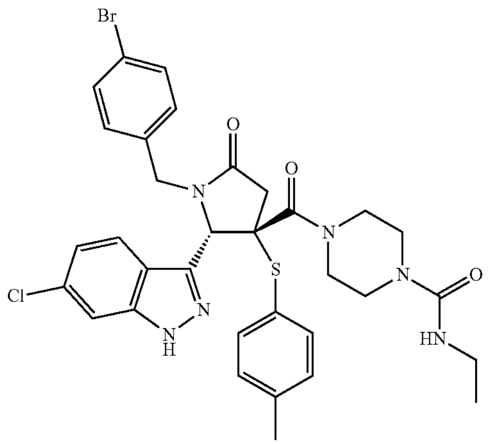
$C_{33}H_{34}BrClN_6O_3S$; MW: 710.10; found (HPLC MS): $[M + H^+]$ = 711.2; Yield: 6%; $IC_{50}$ = 5.0

-continued
PXN780-d1
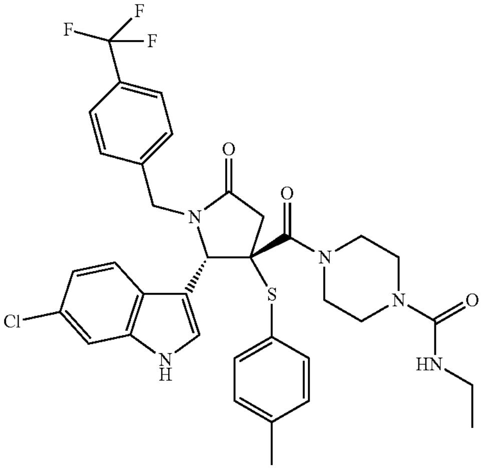
$C_{35}H_{35}ClF_3N_5O_3S$; MW: 698.21; found (HPLC MS): $[M+H^+] = 698.2$; $[M+Na^+] = 720.2$; Yield: 6%; $IC_{50} = 5.3$
PXN781-d1
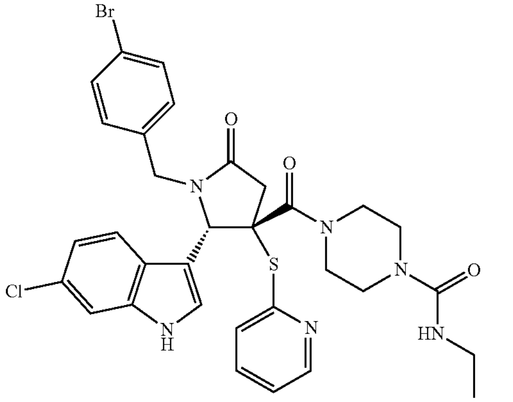
$C_{32}H_{32}BrClN_6O_3S$; MW: 696.07
PXN782-d1
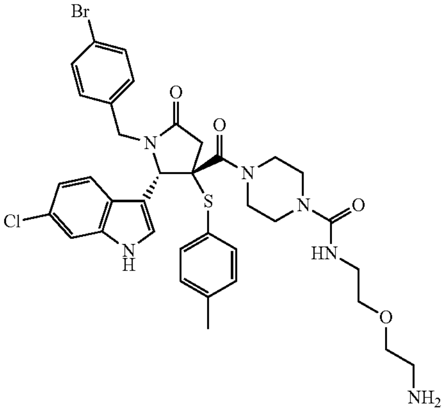
$C_{36}H_{40}BrClN_6O_4S$; MW: 768.18; found (HPLC MS): $[M+H^+] = 769.2$; Yield: 8%
PXN783-d1
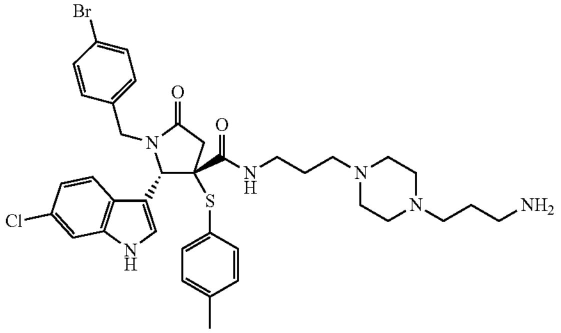
$C_{37}H_{44}BrClN_6O_2S$; MW: 752.22; found (HPLC MS): $[M+H^+] = 753.2$; Yield: 9%
PXN784-d1
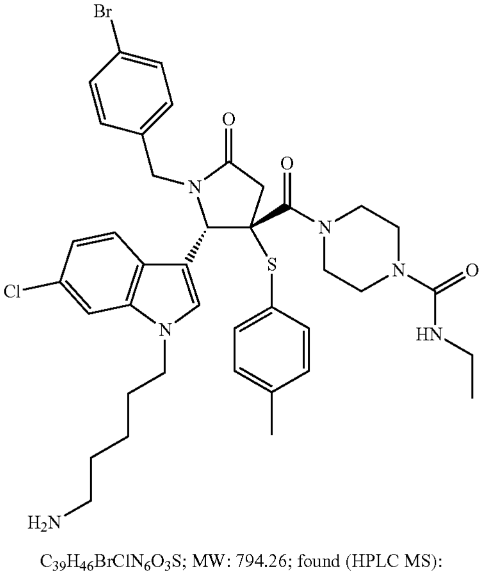
$C_{39}H_{46}BrClN_6O_3S$; MW: 794.26; found (HPLC MS): $[M+H^+] = 795.3$; Yield: 5%
PXN785-d1
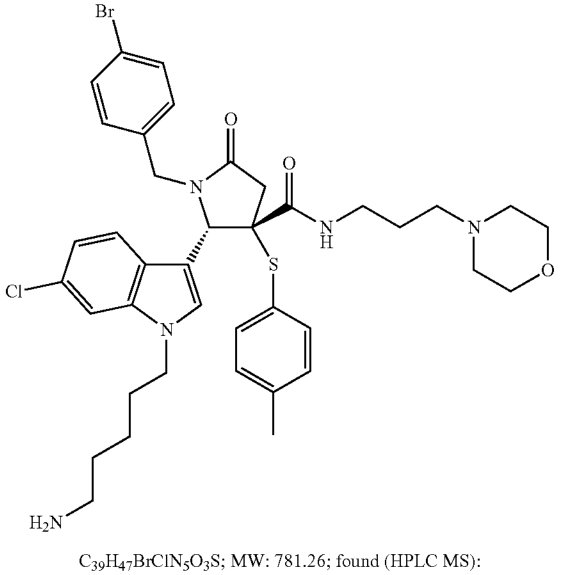
$C_{39}H_{47}BrClN_5O_3S$; MW: 781.26; found (HPLC MS): $[M+H^+] = 781.6$; $[M+Na^+] = 803.8$; Yield: 10%

-continued

PXN787-d1

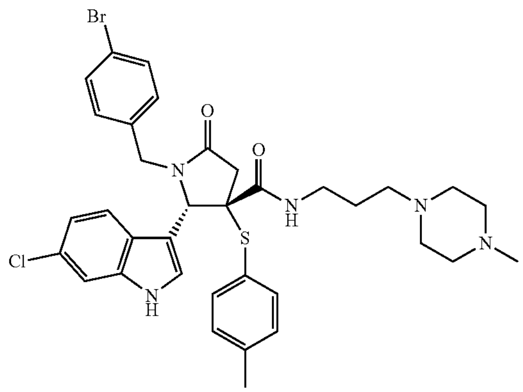

$C_{35}H_{39}BrClN_5O_2S$; MW: 709.15; found (HPLC MS): $[M + H^+] = 709.5$; Yield: 13%; $IC_{50} = 8.3$ PXN791-d1

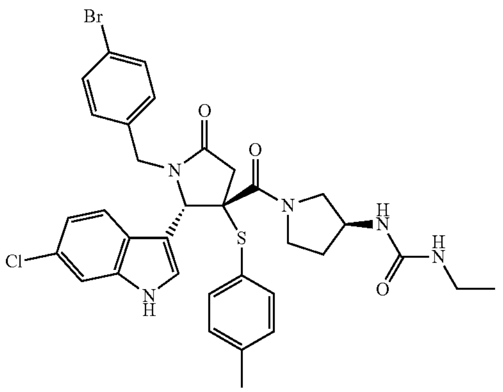

$C_{34}H_{35}BrClN_5O_3S$; MW: 709.11; found (HPLC MS): $[M + H^+] = 710.2$; $[M + Na^+] = 732.0$; Yield: 1%; $IC_{50} = 6.6$ PXN792-d1

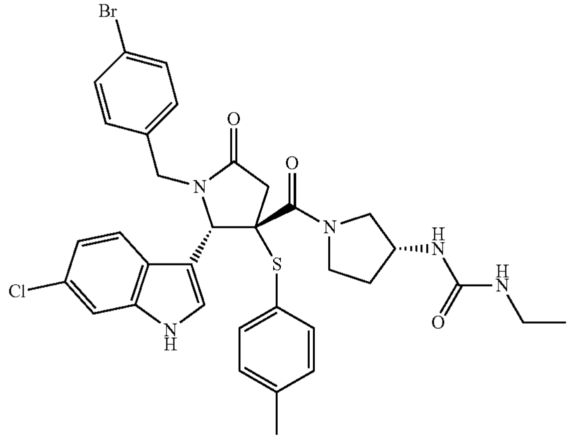

$C_{34}H_{35}BrClN_5O_3S$; MW: 709.11; found (HPLC MS): $[M + H^+] = 708.0$; $[M + Na^+] = 730.1$; Yield: 8%; $IC_{50} = 5.3$ PXN793-d1

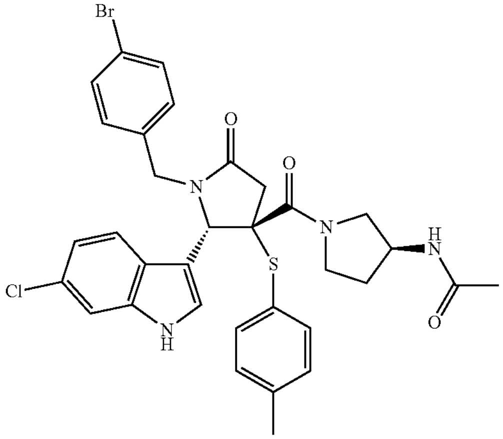

$C_{33}H_{32}BrClN_4O_3S$; MW: 680.07; found (HPLC MS): $[M + Na^+] = 703.1$; Yield: 6%; $IC_{50} = 4.7$ PXN794-d1

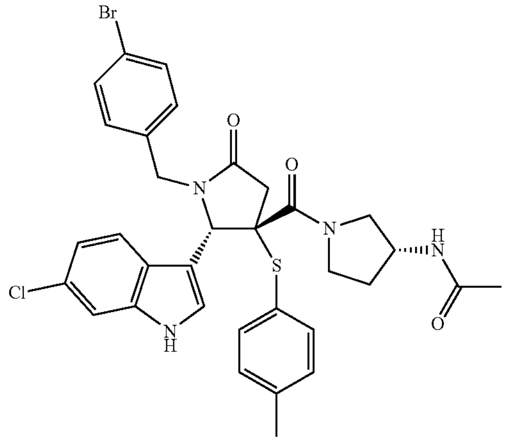

$C_{33}H_{32}BrClN_4O_3S$; MW: 680.07; found (HPLC MS): $[M + H^+] = 679.0$; $[M + Na^+] = 701.0$; Yield: 4%; $IC_{50} = 6.0$ PXN795-d1

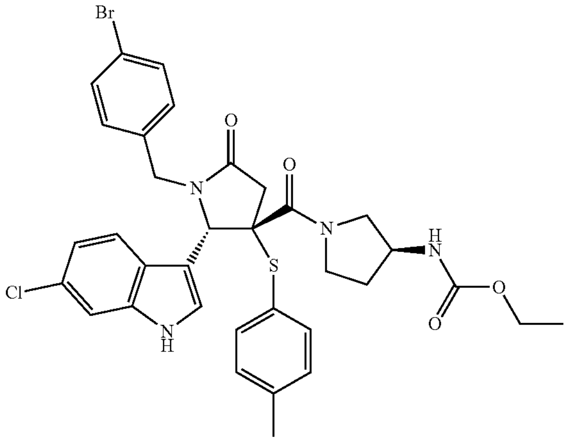

$C_{34}H_{34}BrClN_4O_4S$; MW: 710.10; found (HPLC MS): $[M + H^+] = 711.1$; $[M + Na^+] = 733.1$; Yield: 3%; $IC_{50} = 80.0$ -continued
PXN796-d1
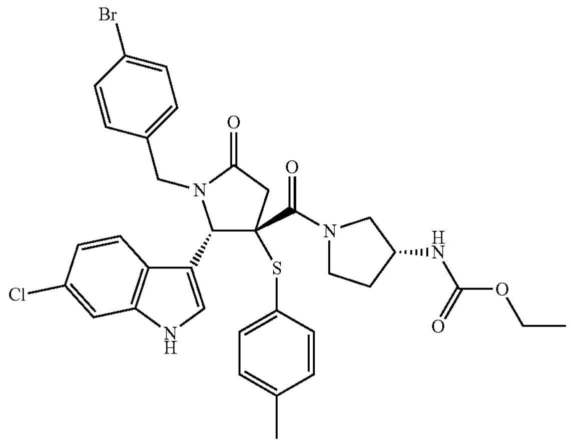
$C_{34}H_{34}BrClN_4O_4S$; MW: 710.10
PXN797-d1
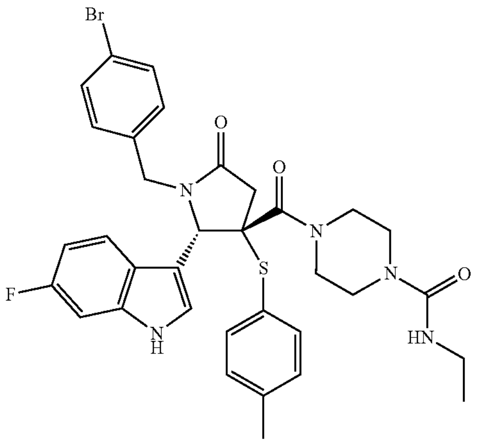
$C_{34}H_{35}BrFN_5O_3S$; MW: 692.66; found (HPLC MS): $[M + H^+] = 693.5$; $[M + Na^+] = 716.2$; Yield: 11%; CCA
PXN798-d1
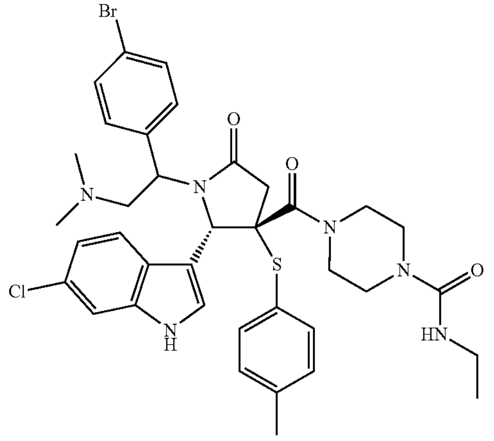
$C_{37}H_{42}BrClN_6O_3S$; MW: 766.21
PXN799-d1
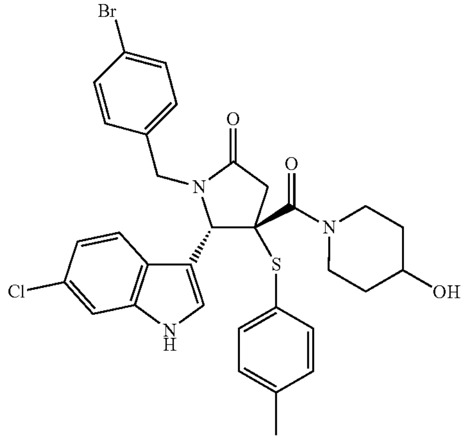
$C_{32}H_{31}BrClN_3O_3S$; MW: 653.04; found (HPLC MS): $[M + H^+] = 651.8$; $[M + Na^+] = 675.7$; Yield: 13%; $IC_{50} = 4.1$
PXN800-d1
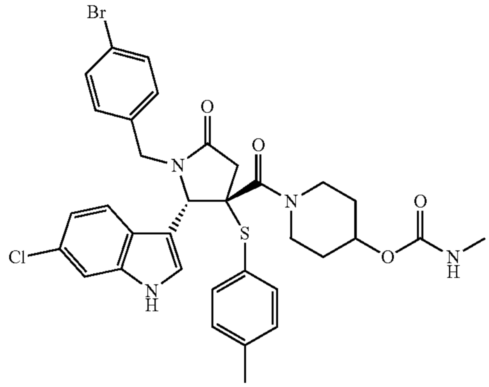
$C_{34}H_{34}BrClN_4O_4S$; MW: 710.10; found (HPLC MS): $[M + H^+] = 711.3$; $[M + Na^+] = 731.2$; Yield: 2%; $IC_{50} = 11.7$
PXN801-d1
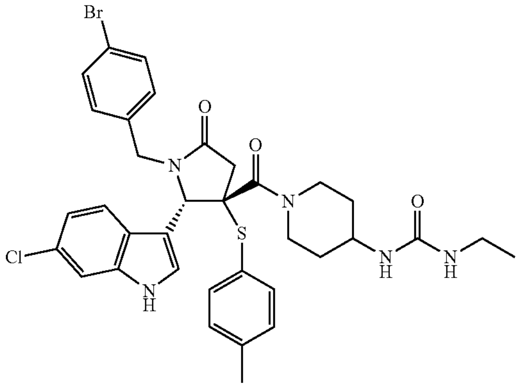
$C_{35}H_{37}BrClN_5O_3S$; MW: 723.14; found (HPLC MS): $[M + H^+] = 724.3$; $[M + Na^+] = 746.3$; Yield: 5%; $IC_{50} > 60$ -continued
PXN802-d1
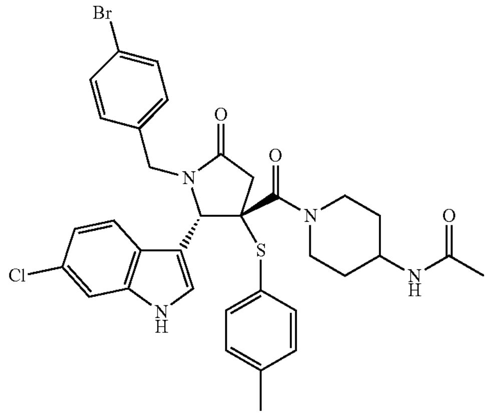
$C_{34}H_{34}BrClN_4O_3S$; MW: 694.10; found (HPLC MS): $[M + H^+]$ = 695.3; Yield: 6%; $IC_{50}$ = 4.5
PXN803-d1
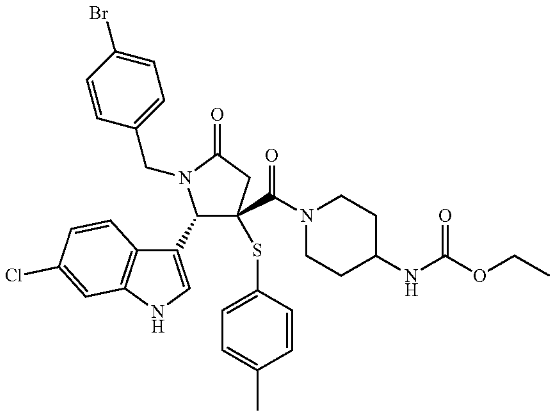
$C_{35}H_{36}BrClN_4O_4S$; MW: 724.12
PXN805-d1
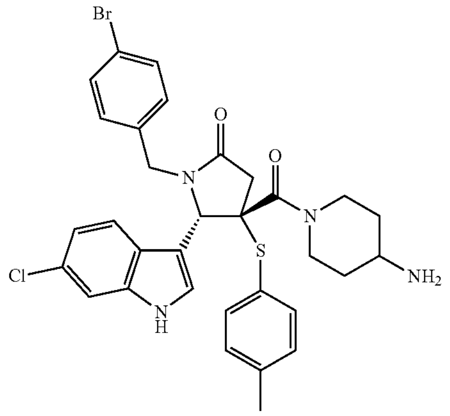
$C_{32}H_{32}BrClN_4O_2S$; MW: 652.06; found (HPLC MS): $[M + H^+]$ = 653.4; $[M + Na^+]$ = 675.4; Yield: 7%; $IC_{50}$ = 5.5
PXN806-d1
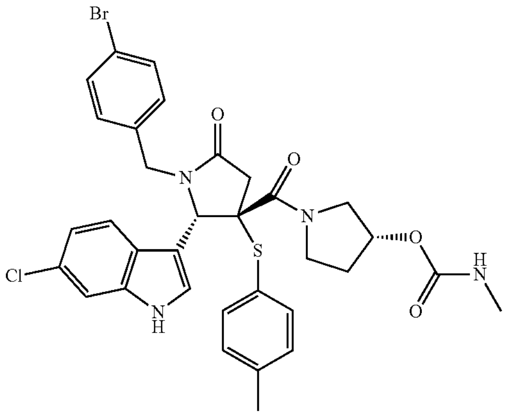
$C_{33}H_{32}BrClN_4O_4S$; MW: 696.07
PXN807-d1
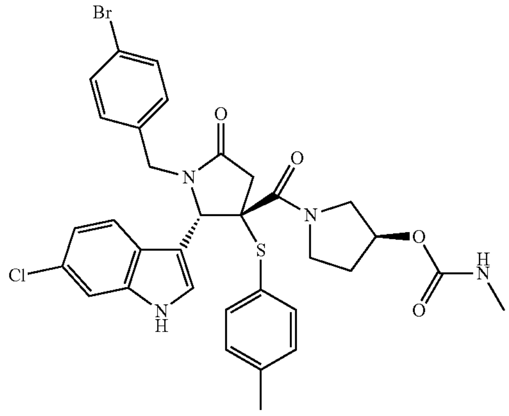
$C_{33}H_{32}BrClN_4O_4S$; MW: 696.07
PXN808-d1
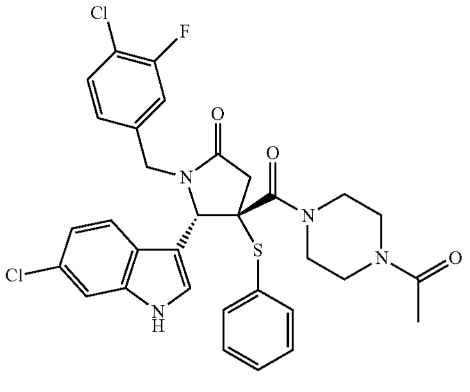
$C_{32}H_{29}Cl_2FN_4O_3S$; MW: 639.58; found (HPLC MS): $[M + H^+]$ = 639.2; $[M + Na^+]$ = 660.9; Yield: 16%; $IC_{50}$ = 1.3

-continued
PXN811-d1
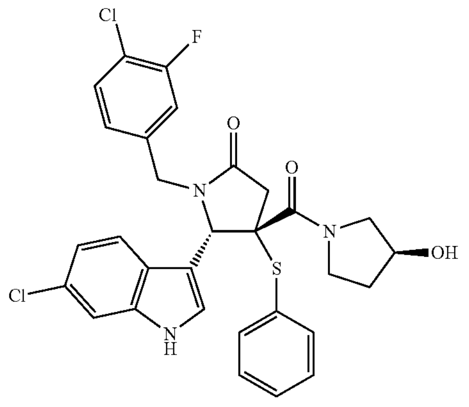
$C_{30}H_{26}Cl_2FN_3O_3S$; MW: 598.53; found (HPLC MS): $[M+H^+] = 598.1$; $[M+Na^+] = 620.0$; Yield: 7%; $IC_{50} = 5.6$
PXN813-d1
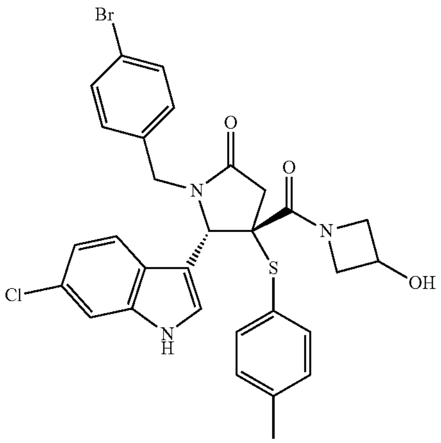
$C_{30}H_{27}BrClN_3O_3S$; MW: 624.99; found (HPLC MS): $[M+H^+] = 624.0$; $[M+Na^+] = 646.0$; Yield: 11%; $IC_{50} = 5.4$
PXN814-d1
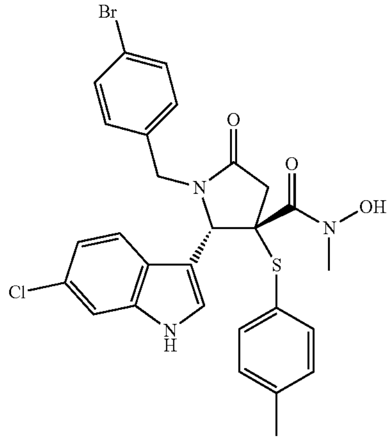
$C_{28}H_{25}BrClN_3O_3S$; MW: 598.95
PXN815-d1
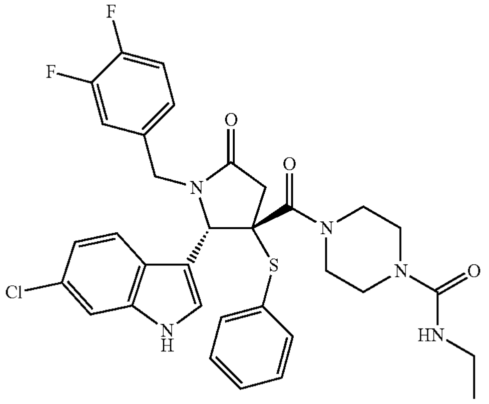
$C_{33}H_{32}ClF_2N_5O_3S$; MW: 652.17; found (HPLC MS): $[M+H^+] = 652.1$; $[M+Na^+] = 674.2$; Yield: 4%; $IC_{50} = 5.0$
PXN816-d1
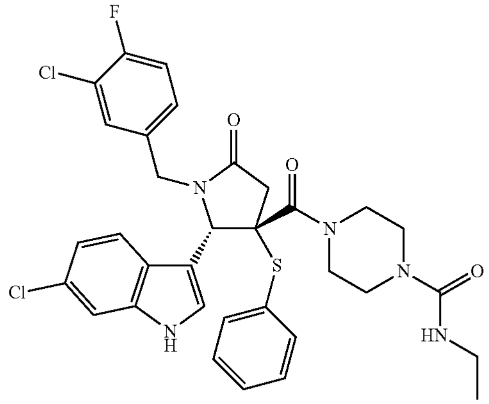
$C_{33}H_{32}Cl_2FN_5O_3S$; MW: 668.62; found (HPLC MS): $[M+H^+] = 668.2$; Yield: 5%; $IC_{50} = 3.2$
PXN817-d2
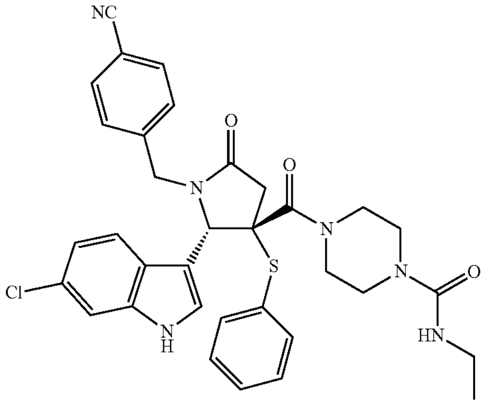
$C_{34}H_{33}ClN_6O_3S$; MW: 641.20; found (HPLC MS): $[M+H^+] = 641.1$; $[M+Na^+] = 663.2$; Yield: 1%; $IC_{50} = 1.0$ -continued PXN820-d1

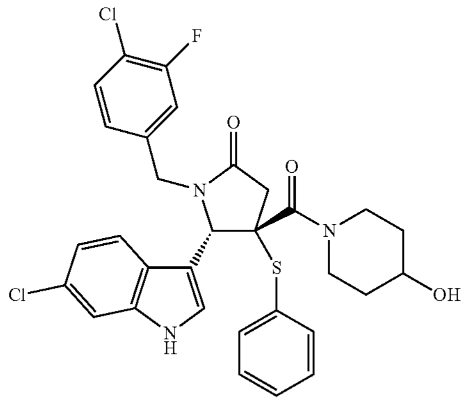

$C_{31}H_{28}Cl_2FN_3O_3S$; MW: 612.56; found (HPLC MS): $[M + H^+] = 612.1$; $[M + Na^+] = 634.1$; Yield: 20%; $IC_{50} = 3.7$ PXN821-d1

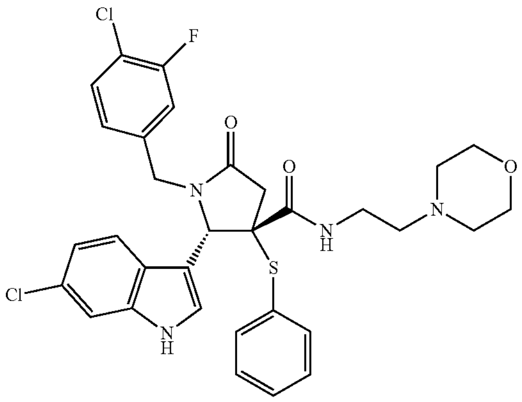

$C_{32}H_{31}Cl_2FN_4O_3S$; MW: 641.60; found (HPLC MS): $[M + H^+] = 641.2$; Yield: 19%; $IC_{50} = 8.6$ PXN822-d1

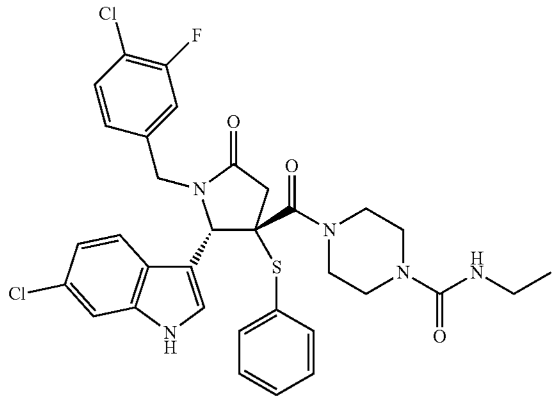

$C_{33}H_{32}Cl_2FN_5O_3S$; MW: 668.62; found (HPLC MS): $[M + H^+] = 668.2$; $[M + Na^+] = 690.1$; Yield: 16%; $IC_{50} = 1.2$ PXN825-d1

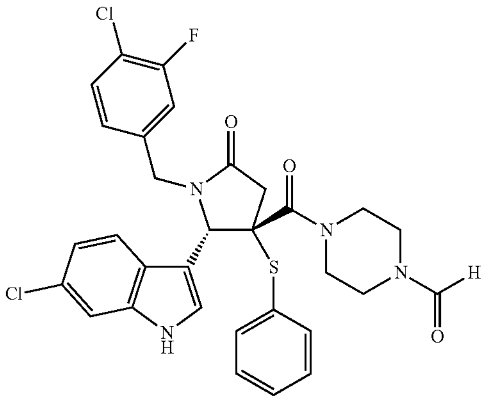

$C_{31}H_{27}Cl_2FN_4O_3S$; MW: 625.55; found (HPLC MS): $[M + H^+] = 627.2$; $[M + Na^+] = 647.1$; Yield: 23%; $IC_{50} = 1.5$ PXN826-d1

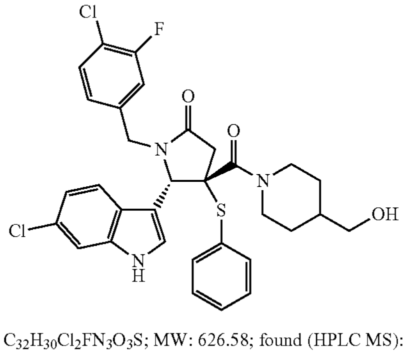

$C_{32}H_{30}Cl_2FN_3O_3S$; MW: 626.58; found (HPLC MS): $[M + Na^+] = 648.1$; Yield: 19%; $IC_{50} = 3.5$ PXN833-d1

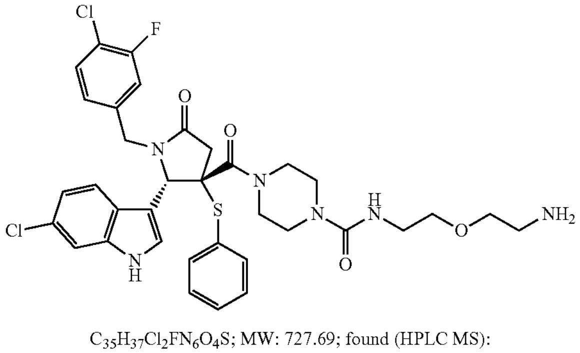

$C_{35}H_{37}Cl_2FN_6O_4S$; MW: 727.69; found (HPLC MS): $[M + H^+] = 727.2$; Yield: 5%

-continued
PXN834-d1
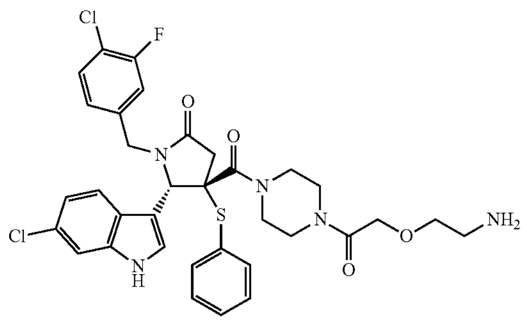
$C_{34}H_{34}Cl_2FN_5O_4S$; MW: 698.65; found (HPLC MS): [M + H$^+$] = 698.1; Yield: 23%
PXN835-d1
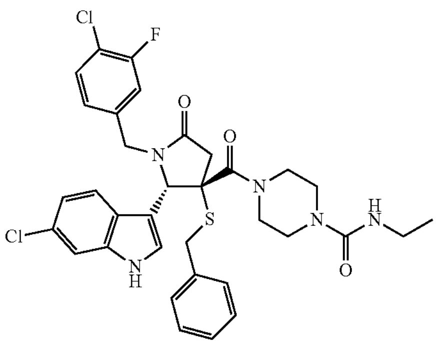
$C_{34}H_{34}Cl_2FN_5O_3S$; MW: 682.65; found (HPLC MS): [M + H$^+$] = 684.3; [M + Na$^+$] = 703.9; Yield: 5%; $IC_{50}$ = 3.4
PXN836-d2
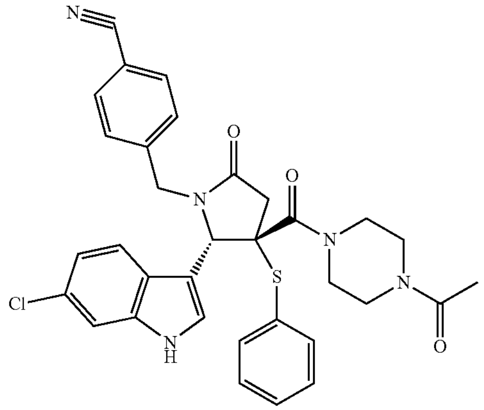
$C_{33}H_{30}ClN_5O_3S$; MW: 612.16; found (HPLC MS): [M + H$^+$] = 612.5; [M + Na$^+$] = 634.5; Yield: 3%
PXN849-d1
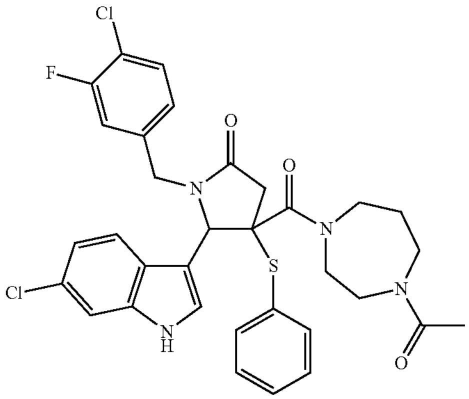
$C_{33}H_{31}Cl_2FN_4O_3S$; MW: 653.61; found (HPLC MS): [M + H$^+$] = 653.4; [M + Na$^+$] = 677.4; Yield: 6%
PXN850-d1
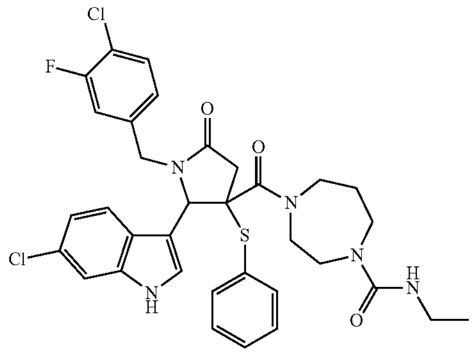
$C_{34}H_{34}Cl_2FN_5O_3S$; MW: 682.65; found (HPLC MS): [M + H$^+$] = 682.4; Yield: 11%
PXN670-d1
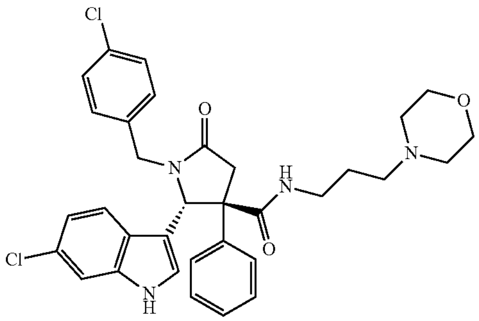
$C_{33}H_{34}Cl_2N_4O_3$; MW: 605.57; found (HPLC MS): [M + H$^+$] = 605.0; Yield: 6%; $IC_{50}$ = 12.5

-continued
PXN670-d2
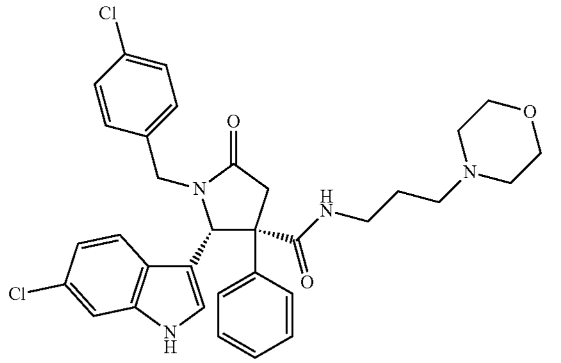
$C_{33}H_{34}Cl_2N_4O_3$; MW: 605.57; found (HPLC MS): $[M + H^+] = 605.0$; Yield: 7%; $IC_{50} = 11.2$
PXN778-d1
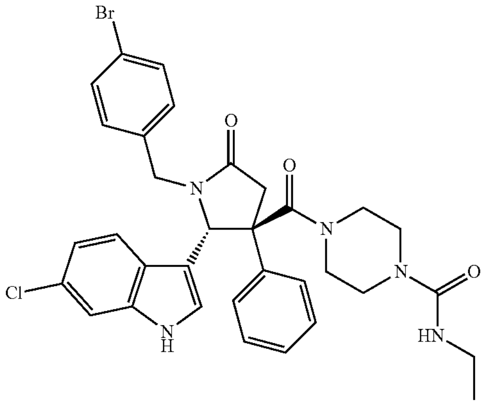
$C_{33}H_{33}BrClN_5O_3$; MW: 663.02; found (HPLC MS): $[M + H^+] = 664.1$; Yield: 11%; $IC_{50} = 8.1$
PXN788-d1
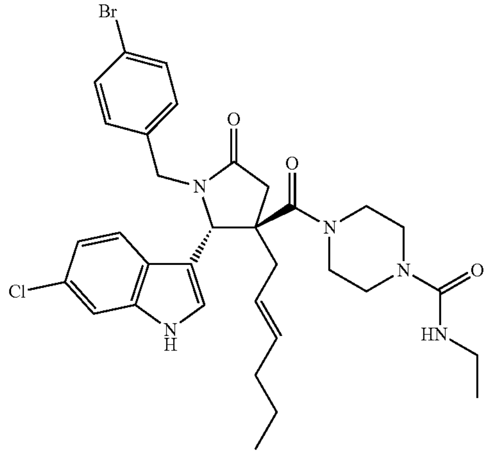
$C_{33}H_{39}BrClN_5O_3$; MW: 669.07; found (HPLC MS): $[M + H^+] = 670.3$; $[M + Na^+] = 692.2$; Yield: 1%; $IC_{50} = 6.6$
PXN790-d1
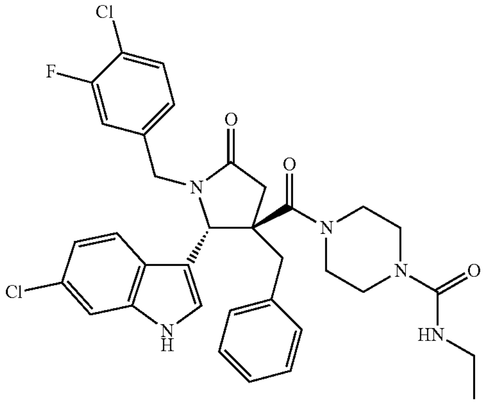
$C_{34}H_{34}Cl_2FN_5O_3$; MW: 650.59; found (HPLC MS): $[M + H^+] = 650.1$; $[M + Na^+] = 672.1$; Yield: 1%; $IC_{50} = 3.0$
PXN804-d1
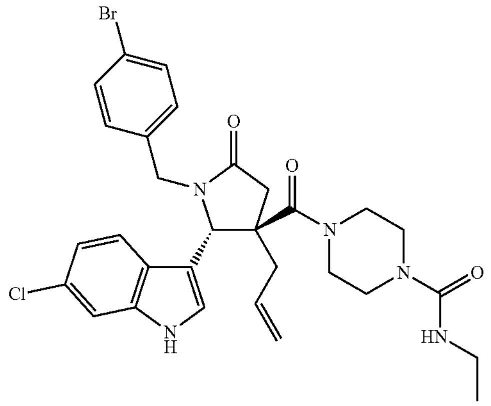
$C_{30}H_{33}BrClN_5O_3$; MW: 626.99; found (HPLC MS): $[M + H^+] = 628.2$; $[M + Na^+] = 650.2$; Yield: 9%; $IC_{50} = 9.0$
PXN809-d1
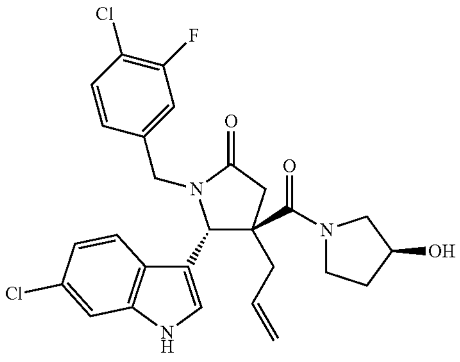
$C_{27}H_{26}Cl_2FN_3O_3$; MW: 530.43

-continued
PXN810-d1
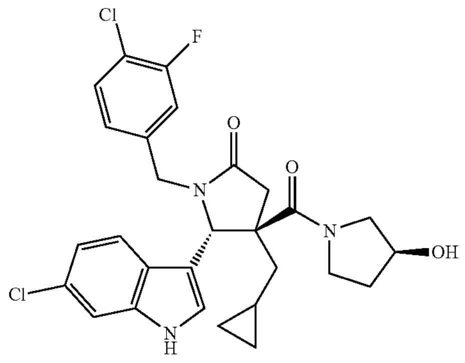
$C_{28}H_{28}Cl_2FN_3O_3$; MW: 544.46
PXN812-d1
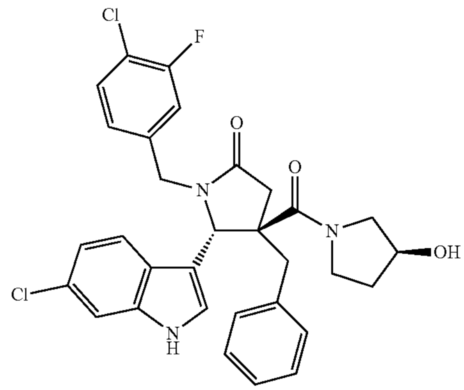
$C_{31}H_{28}Cl_2FN_3O_3$; MW: 580.49; found (HPLC MS): $[M + H^+] = 580.1$; $[M + Na^+] = 602.1$; Yield: 4%; $IC_{50} = 11.9$
PXN823-d1
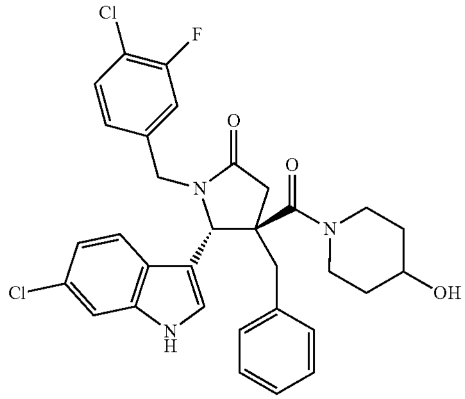
$C_{32}H_{30}Cl_2FN_3O_3$; MW: 594.52
PXN824-d1
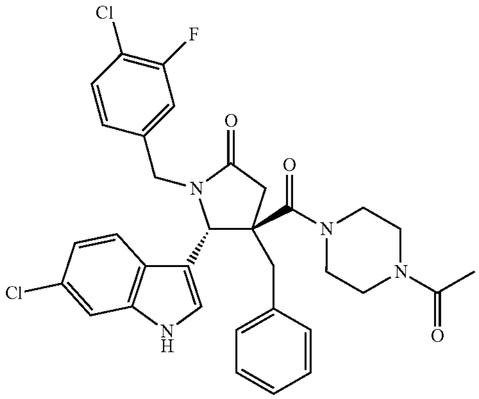
$C_{33}H_{31}Cl_2FN_4O_3$; MW: 621.54
PXN827-d1
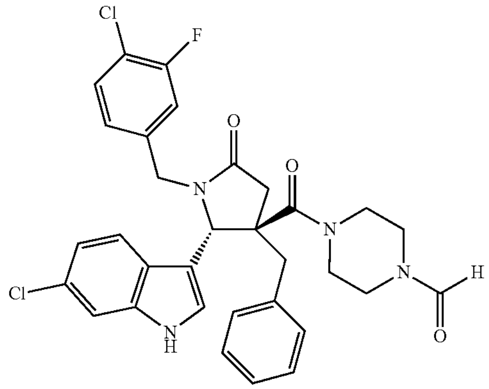
$C_{32}H_{29}Cl_2FN_4O_3$; MW: 607.52
PXN828-d1
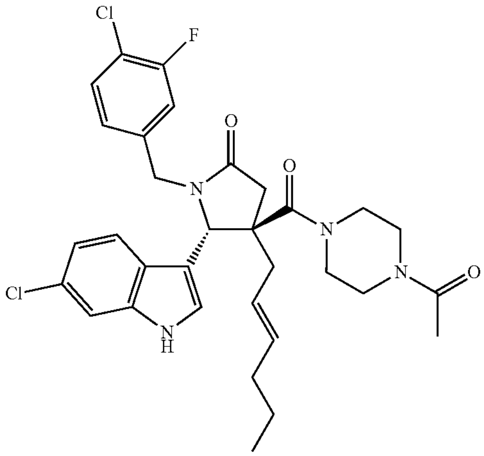
$C_{32}H_{35}Cl_2FN_4O_3$; MW: 613.57

-continued

PXN829-d1

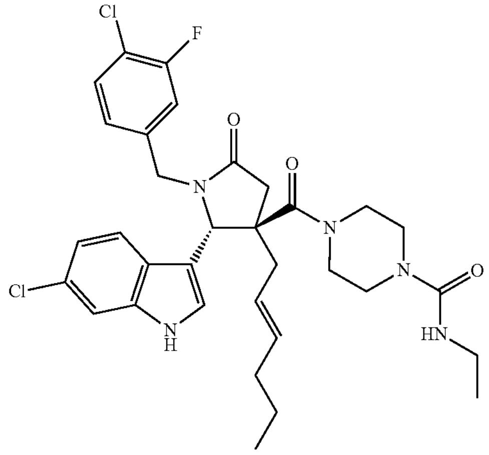

$C_{33}H_{38}Cl_2FN_5O_3$; MW: 642.61; found (HPLC MS): $[M + H^+] = 642.2$; $[M + Na^+] = 664.2$; Yield: 1%; $IC_{50} = 12.5$ PXN830-d1

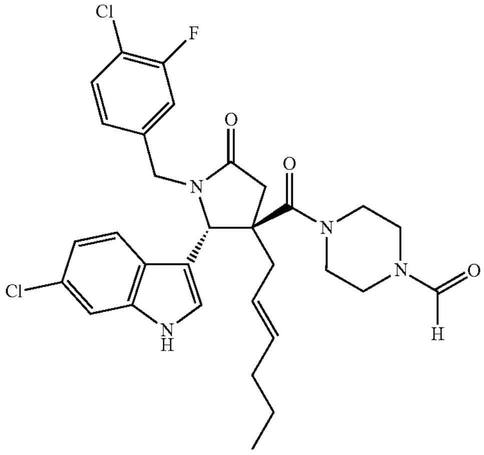

$C_{31}H_{33}Cl_2FN_4O_3$; MW: 599.54; found (HPLC MS): $[M + H^+] = 599.2$; $[M + Na^+] = 621.2$; Yield: 1%; $IC_{50} = 10.2$ PXN831-d1

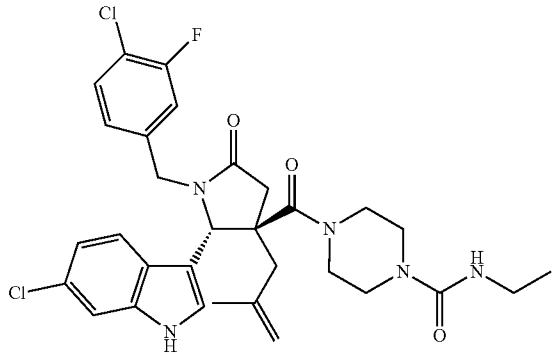

$C_{31}H_{34}Cl_2FN_5O_3$; MW: 614.55; found (HPLC MS): $[M + H^+] = 614.2$; $[M + Na^+] = 636.2$; Yield: 1%; $IC_{50} = 4.9$ PXN832-d1

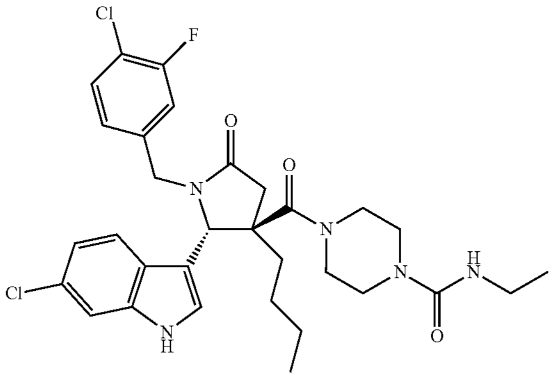

$C_{31}H_{36}Cl_2FN_5O_3$; MW: 616.57; found (HPLC MS): $[M + H^+] = 616.3$; Yield: 1%; $IC_{50} = 7.9$ PXN789-d1

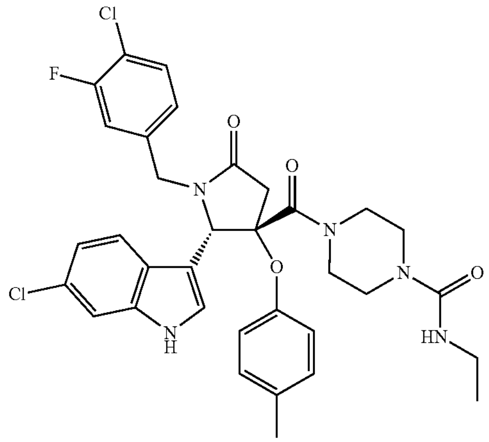

$C_{34}H_{34}Cl_2FN_5O_4$; MW: 666.59; found (HPLC MS): $[M + H^+] = 666.1$; Yield: 1%; $IC_{50} = 11.7$ PXN723-d1

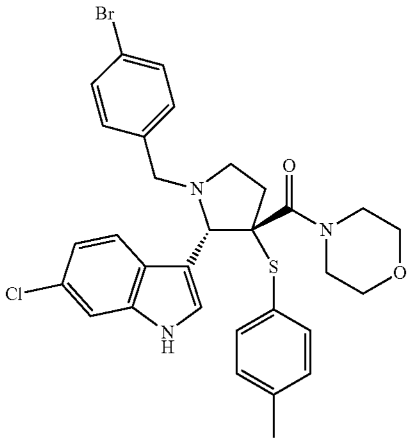

$C_{31}H_{31}BrClN_3O_2S$; MW: 625.03; found (HPLC MS): $[M + H^+] = 626.2$; Yield: 2%; $IC_{50} = 15.1$ -continued
PXN724-d1
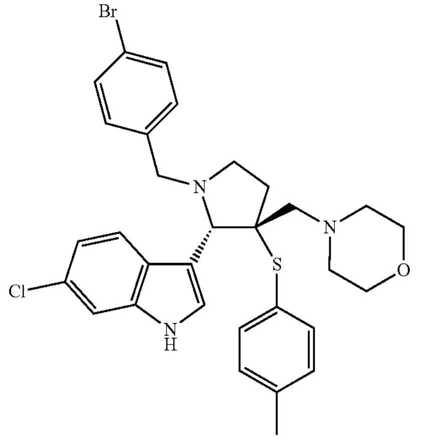
$C_{31}H_{33}BrClN_3OS$; MW: 611.05; found (HPLC MS): $[M + H^+] = 612.3$; Yield: 1%; $IC_{50} = 20.6$
PXN818-d1
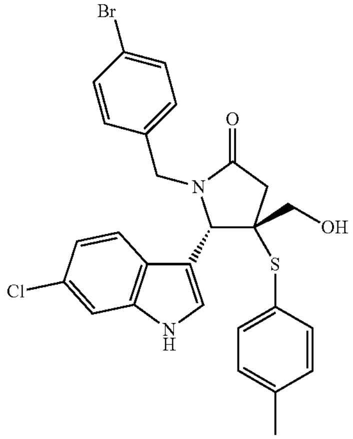
$C_{27}H_{24}BrClN_2O_2S$; MW: 555.93; found (HPLC MS): $[M + H^+] = 556.9$; $[M + Na^+] = 577.1$; Yield: 10%; $IC_{50} = 8.4$
PXN819-d1
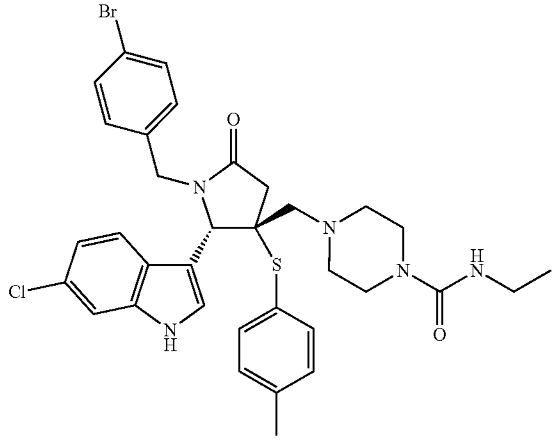
$C_{34}H_{37}BrClN_5O_2S$; MW: 695.13
PXN837-d1
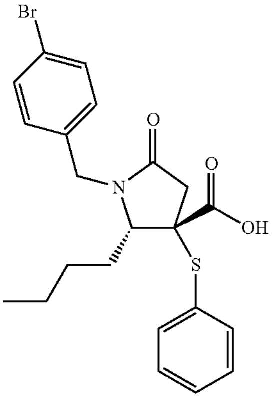
$C_{22}H_{24}BrNO_3S$; MW: 462.41; found (HPLC MS): $[M + H^+] = 464.2$; Yield: 5%
PXN838-d1
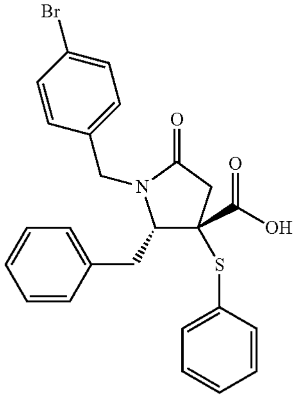
$C_{25}H_{22}BrNO_3S$; MW: 496.43; found (HPLC MS): $[M + H^+] = 496.9$; Yield: 2%
PXN839-d1
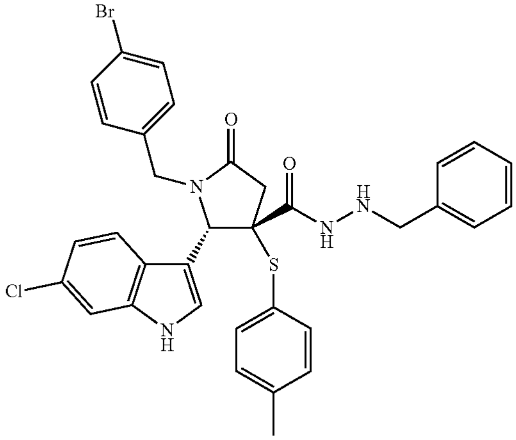
$C_{34}H_{30}BrClN_4O_2S$; MW: 674.06; found (HPLC MS): $[M + H^+] = 675.4$; $[M + Na^+] = 696.9$; Yield: 10%

-continued

PXN840-d1

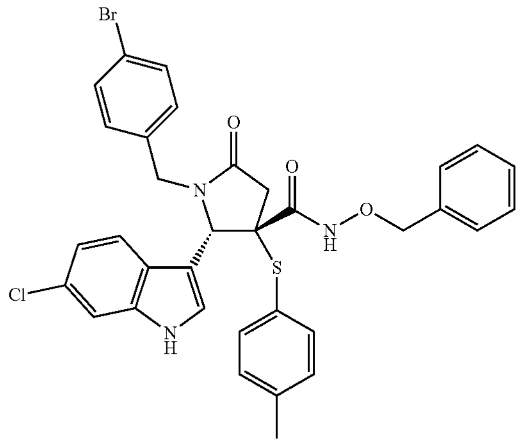

$C_{34}H_{29}BrClN_3O_3S$; MW: 675.05; found (HPLC MS): $[M+H^+]$ = 676.7; $[M+Na^+]$ = 698.3; Yield: 9%

PXN841-d1

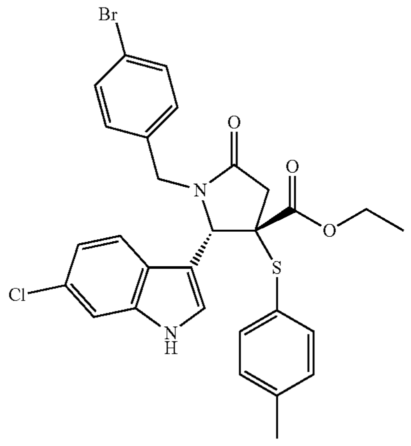

$C_{29}H_{26}BrClN_2O_3S$; MW: 597.96; found (HPLC MS): $[M+H^+]$ = 599.3; $[M+Na^+]$ = 620.9; Yield: 11%

PXN842-d1

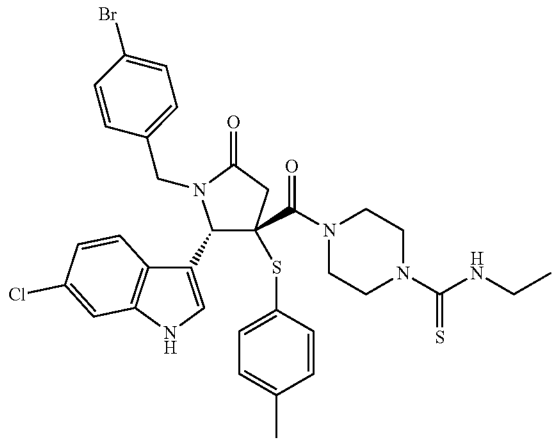

$C_{34}H_{35}BrClN_5O_2S_2$; MW: 725.18; found (HPLC MS): $[M+H^+]$ = 726.5; $[M+Na^+]$ = 749.7; Yield: 9%

PXN843-d1

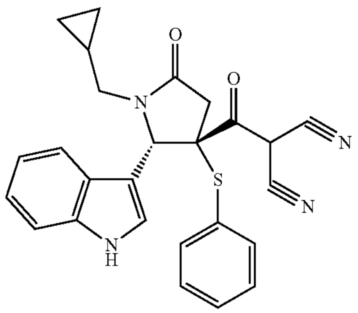

$C_{26}H_{22}N_4O_2S$; MW: 454.55; found (HPLC MS): $[M+H^+]$ = 455.3; $[M+Na^+]$ = 477.2; Yield: 22%

PXN844-d1

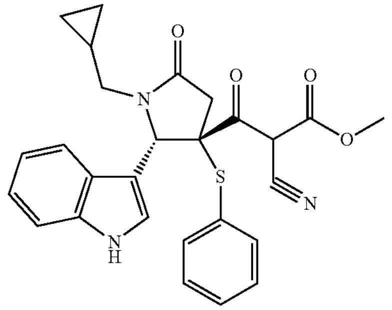

$C_{27}H_{25}N_3O_4S$; MW: 487.58; found (HPLC MS): $[M+H^+]$ = 488.2; $[M+Na^+]$ = 510.3; Yield: 22%

PXN845-d1

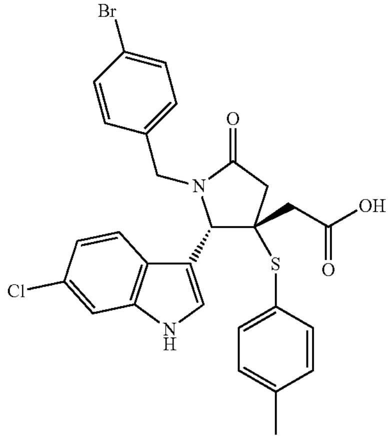

$C_{28}H_{24}BrClN_2O_3S$; MW: 583.94; found (HPLC MS): $[M+H^+]$ = 585.2; $[M+Na^+]$ = 607.4; Yield: 5%

-continued
PXN846-d1
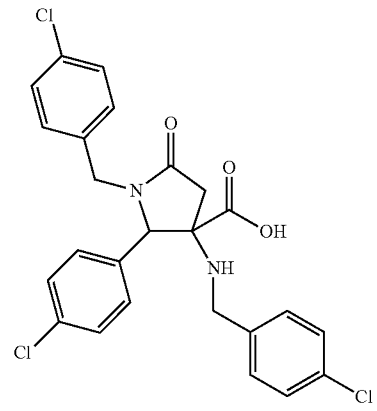
$C_{25}H_{21}Cl_3N_2O_3$; MW: 503.82; found (HPLC MS): $[M + H^+]$ = 505.2; Yield: 4%
PXN847-d1
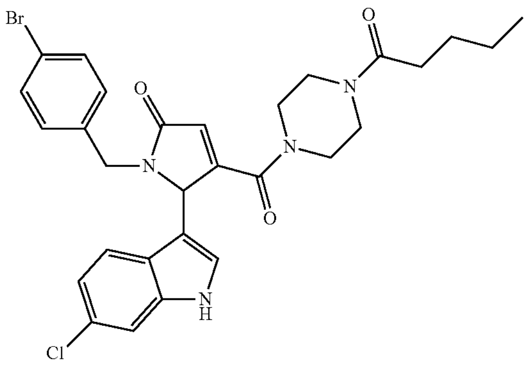
$C_{29}H_{30}BrClN_4O_3$; MW: 597.94; found (HPLC MS): $[M + H^+]$ = 597.3; Yield: 7%
PXN848-d1
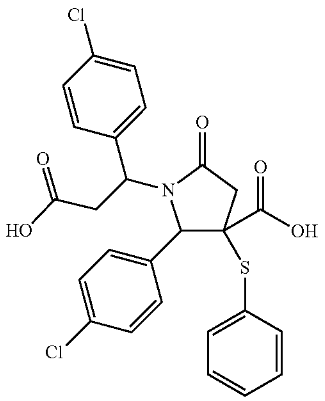
$C_{26}H_{21}Cl_2NO_5S$; MW: 530.43; found (HPLC MS): $[M + H^+]$ = 530.2; $[M + Na^+]$ = 552.4; Yield: 13%
PXN 1000
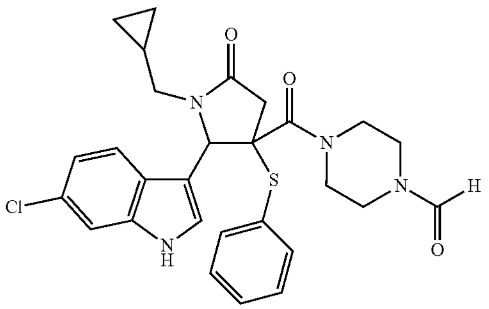
$C_{28}H_{29}ClN_4O_3S$; MW: 537.1; found (HPLC MS): $[M + H^+]$ = 537.1; Yield: 9%
PXN 1001
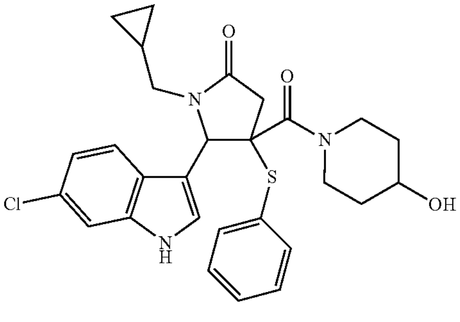
$C_{28}H_{30}ClN_3O_3S$; MW: 524.1; found (HPLC MS): $[M + Na^+]$ = 546.2; Yield: 19%
PXN 1002
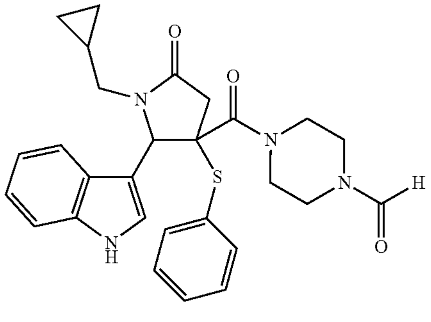
$C_{28}H_{30}N_4O_3S$; MW: 502.64; found (HPLC MS): $[M + H^+]$ = 503.2, $[M + Na^+]$ = 525.2; Yield: 11%

-continued

PXN 1003

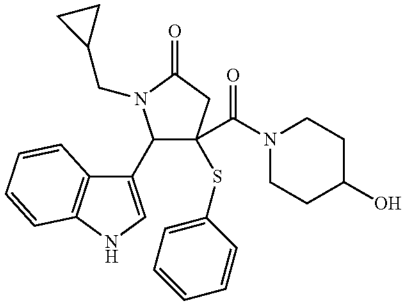

$C_{28}H_{31}N_3O_3S$; MW: 489.64; found (HPLC MS): $[M + H^+] = 490.5$, $[M + Na^+] = 512.2$; Yield: 12%

PXN 1004

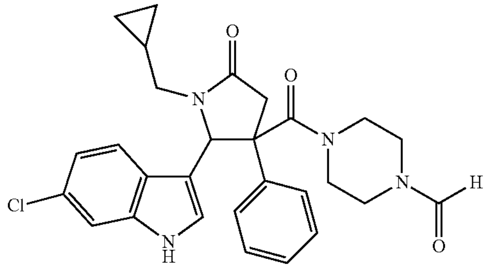

$C_{28}H_{29}ClN_4O_3$; MW: 505.02; found (HPLC MS): $[M + H^+] = 505.2$; Yield: 11%

PXN 1005

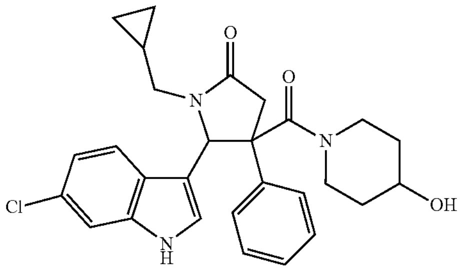

$C_{28}H_{30}ClN_3O_3$; MW: 492.02; found (HPLC MS): $[M + H^+] = 492.2$; Yield: 13%

PXN 1006

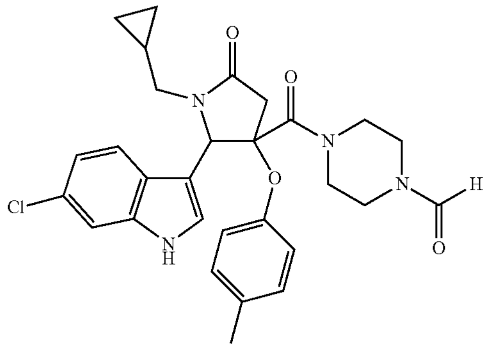

$C_{29}H_{31}ClN_4O_4$; MW: 535.05

PXN 1007

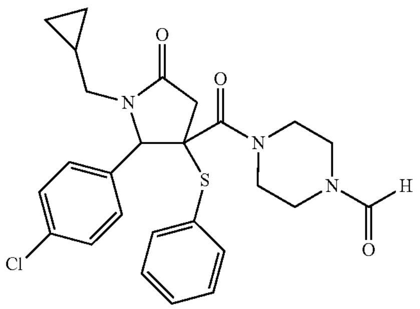

$C_{26}H_{28}ClN_3O_3S$; MW: 498.05; found (HPLC MS): $[M + H^+] = 498.3$; Yield: 5%

PXN 1008

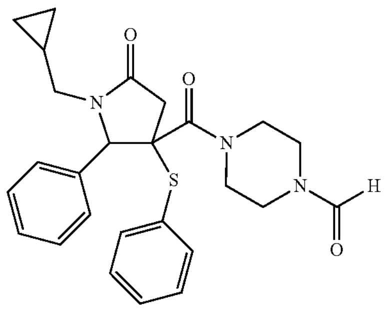

$C_{26}H_{29}N_3O_3S$; MW: 463.60; found (HPLC MS): $[M + H^+] = 464.3$; Yield: 31%

PXN 1009

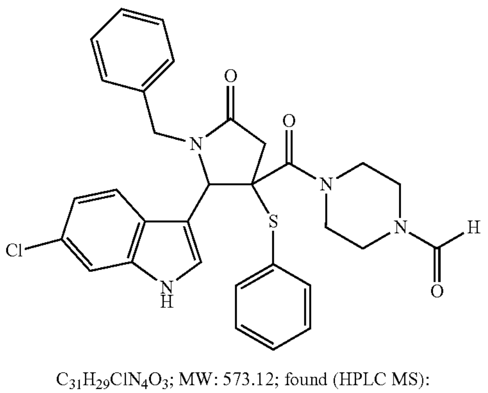

$C_{31}H_{29}ClN_4O_3$; MW: 573.12; found (HPLC MS): $[M + H^+] = 574.4$, $[M + Na^+] = 595.4$; Yield: 1%

PXN 1010

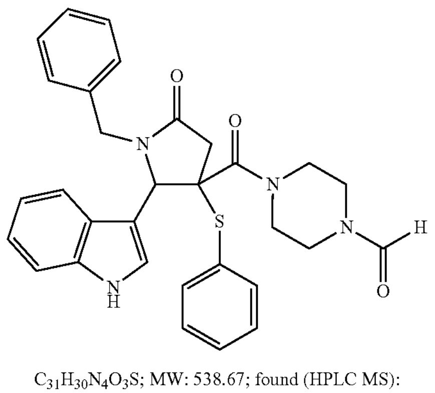

$C_{31}H_{30}N_4O_3S$; MW: 538.67; found (HPLC MS): $[M + H^+] = 539.4$; Yield: 3%

-continued
PXN 1011
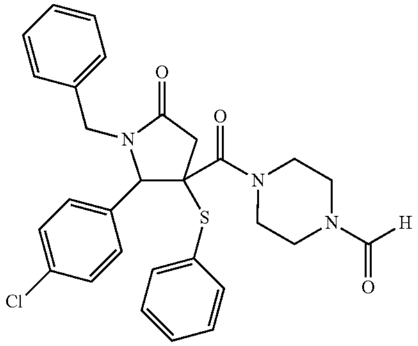
$C_{29}H_{28}ClN_3O_3S$; MW: 534.08; found (HPLC MS): $[M + H^+]$ = 534.3; Yield: 13%
PXN 1012
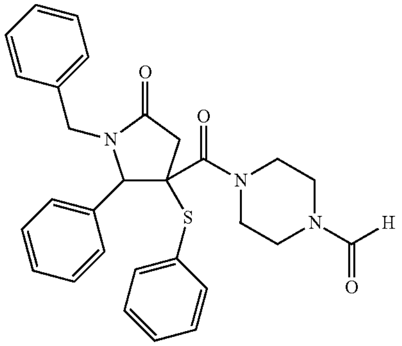
$C_{29}H_{29}N_3O_3S$; MW: 499.64; found (HPLC MS): $[M + H^+]$ = 500.3; Yield: 31%
PXN 1013
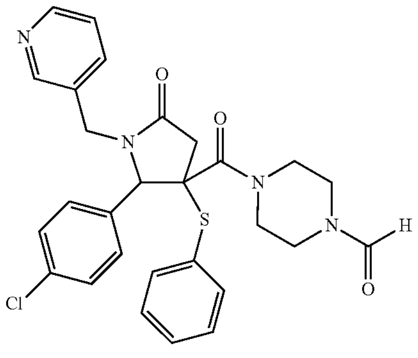
$C_{28}H_{27}ClN_4O_3S$; MW: 535.07; found (HPLC MS): $[M + H^+]$ = 535.3; Yield: 2%
PXN 1014
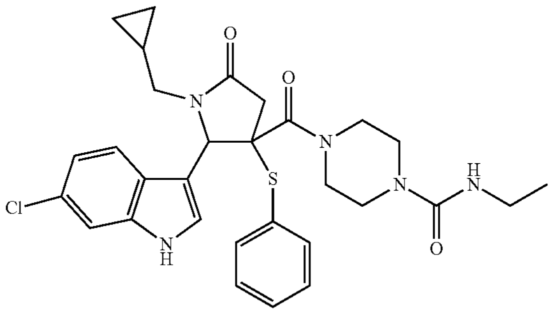
$C_{30}H_{34}ClN_5O_3S$; MW: 580.2; found (HPLC MS): $[M + Na^+]$ = 602.4; Yield: 14%
PXN 1015
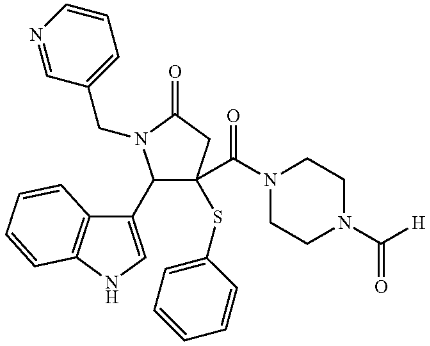
$C_{30}H_{29}N_5O_3S$; MW: 539.66; found (HPLC MS): $[M + H^+]$ = 540.4; Yield: 1%
PXN 1016
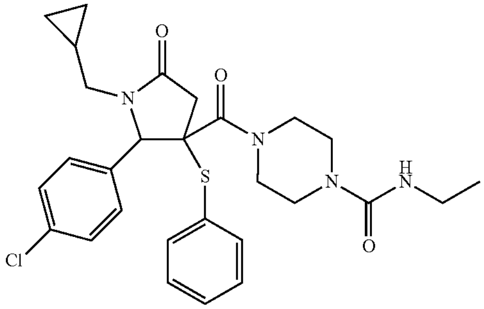
$C_{28}H_{33}ClN_4O_3S$; MW: 541.12; found (HPLC MS): $[M + H^+]$ = 541.4; Yield: 4%

-continued
PXN 1017
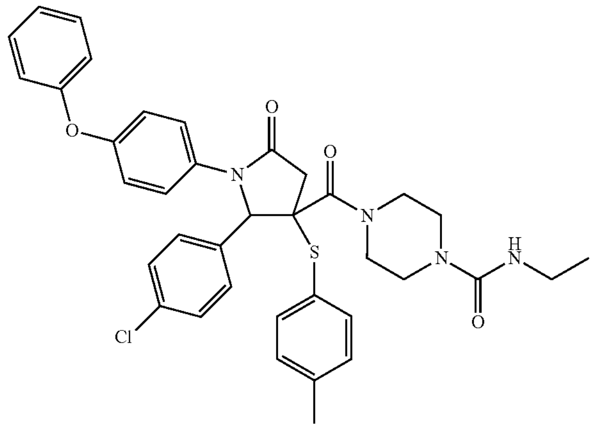
$C_{37}H_{37}ClN_4O_4S$; MW: 669.2; found (HPLC MS): [M + H$^+$] = 671.7, [M + Na$^+$] = 691.3; Yield: 3%
PXN 1018
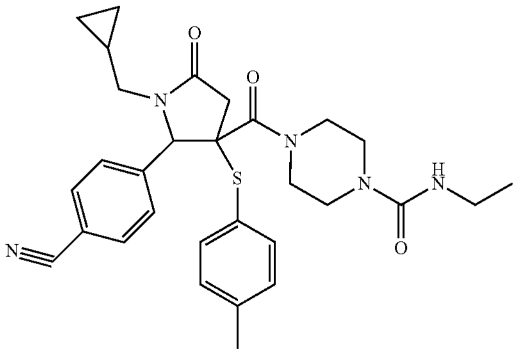
$C_{30}H_{35}N_5O_3S$; MW: 545.7; found (HPLC MS): [M + H$^+$] = 546.3; Yield: 18%
PXN 1019
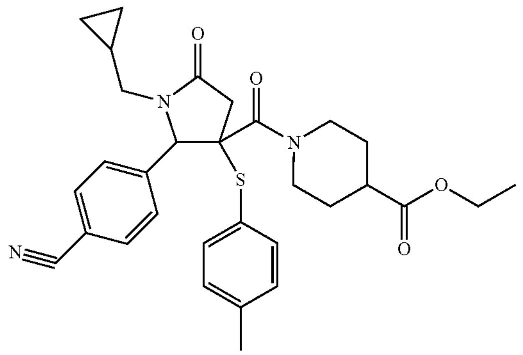
$C_{31}H_{35}N_3O_4S$; MW: 545.7; found (HPLC MS): [M + H$^+$] = 546.3, [M + Na$^+$] = 568.3; Yield: 27%
PXN 1020
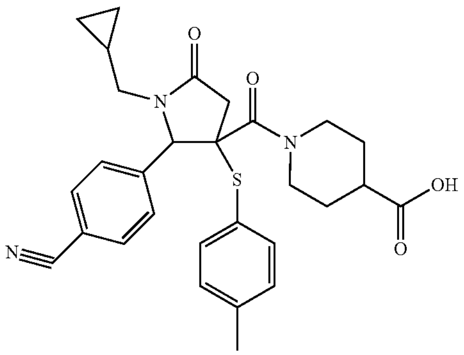
$C_{29}H_{31}N_3O_4S$; MW: 517.7
PXN 1021
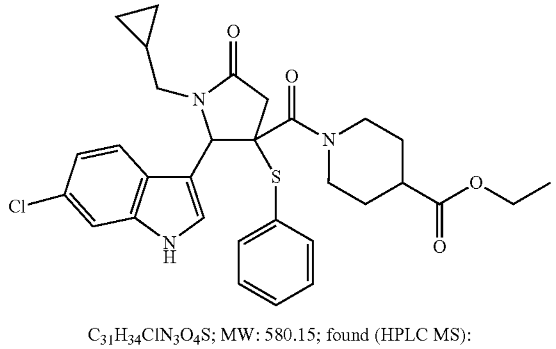
$C_{31}H_{34}ClN_3O_4S$; MW: 580.15; found (HPLC MS): [M + H$^+$] = 580.3; Yield: 20%
PXN 1022
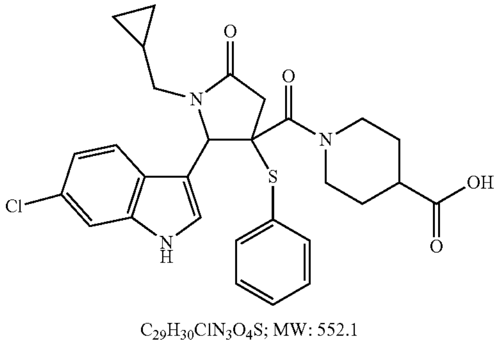
$C_{29}H_{30}ClN_3O_4S$; MW: 552.1

-continued

PXN 1023

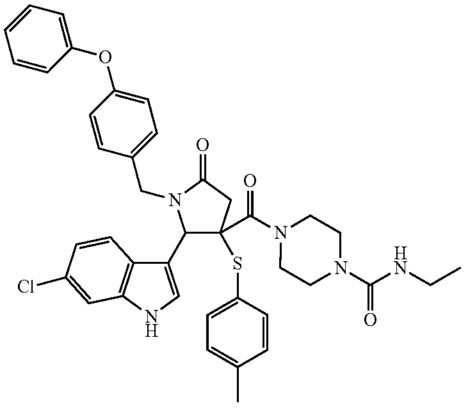

$C_{40}H_{40}ClN_5O_4S$; MW: 722.3; found (HPLC MS): $[M+H^+] = 722.6$, $[M+Na+] = 744.3$; Yield: 4%

PXN 1024

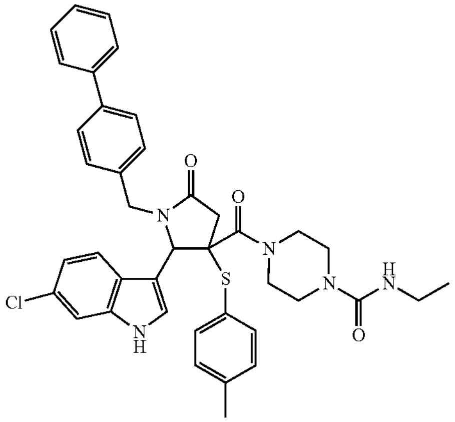

$C_{40}H_{40}ClN_5O_3S$; MW: 706.3; found (HPLC MS): $[M+H^+] = 708.2$; Yield: 1%

Further modifications of the pyrrolidin-2-one scaffold are possible by using the following procedures:

1) Redox Variations:

Scheme 1

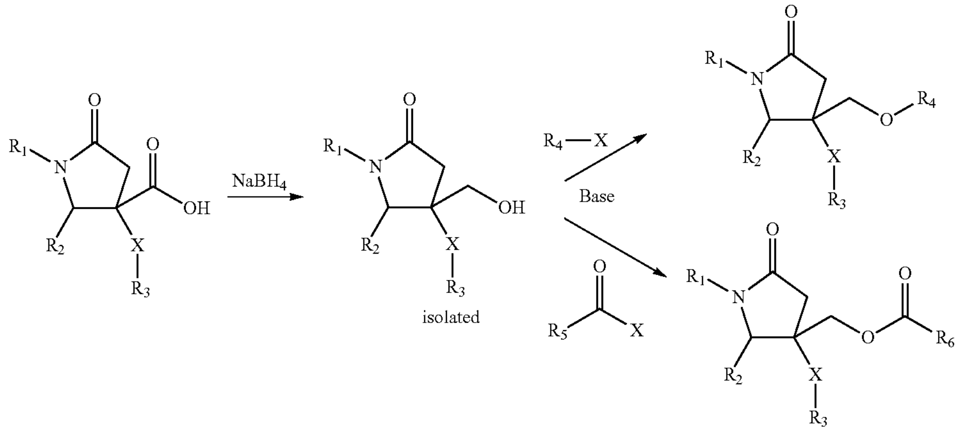

In the presence of $NaBH_4$, it is possible to reduce the carboxylic acid function of the MCR-product to the corresponding alcohol (see PXN818-d1). The isolated alcohol can be further converted to the corresponding ether (alkylation with various halogens) or to the corresponding ester (acylation with acyl chloride) (Scheme I).

Furthermore, the obtained alcohol can be oxidized to the corresponding aldehyde (Swern oxidation). Alternatively, this aldehyde can also be obtained by selective reduction of the carboxylic acid. The aldehyde can be converted to numerous further compounds.

Scheme 2

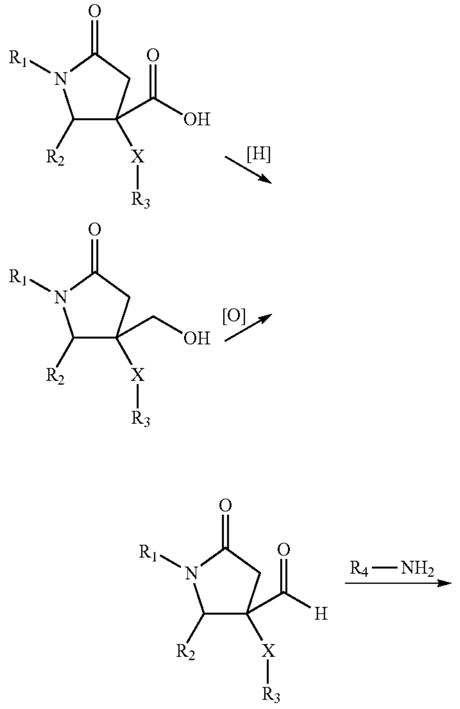

aldehyde

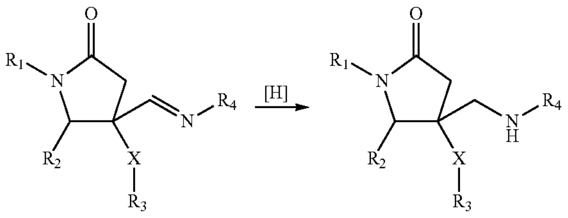

reductive amination

As can be seen from scheme 2, amines are accessible via a reductive amination process. Further, a Knoevenagel condensation is also possible for modification yielding new substituted pyrrolidin-2-ones as shown in Scheme 3.

Scheme 3

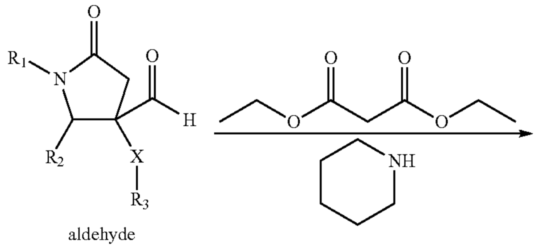

aldehyde

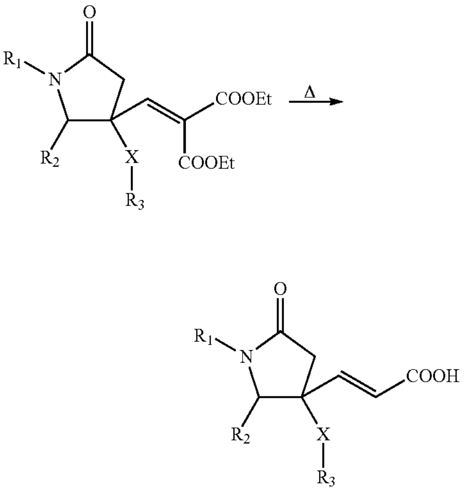

2) Amide Variations

Different amides have been synthesized by aminolysis of the pentafluorophenyl ester using various amines. Other nucleophilic compounds are also suitable to attack the activated carbone of the pentafluorophenyl ester, leading to new pyrrolidin-2-one derivatives as shown in Scheme 4, Scheme 4

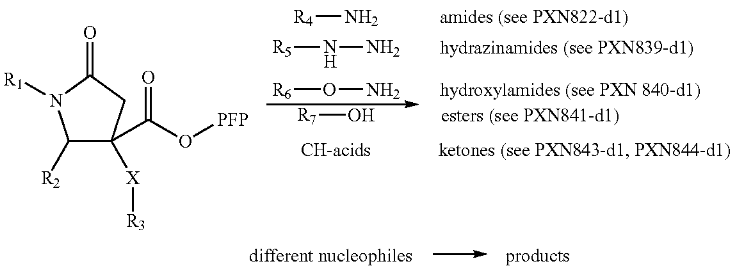

3) Reduction of Amide

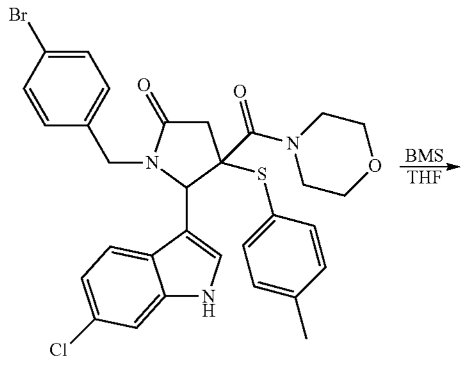

PXN717-d1

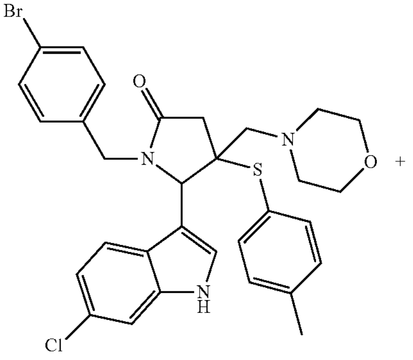

PXN723-d1

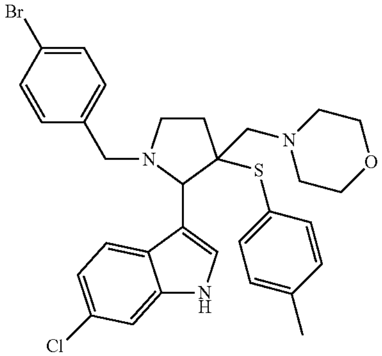

PXN724-d1

PXN717-d1 has been treated with BMS (dimethylsulfide borane) yielding a mixture of the two compounds PXN723-d1 and PXN724-d1.

4) Homologation of Carboxylic Acids (Arndt-Eistert Reaction)

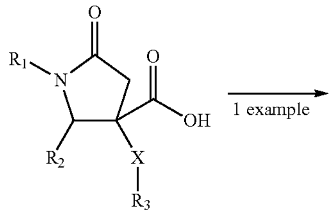

-continued

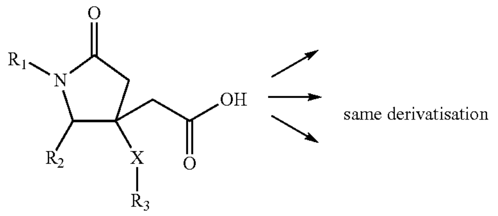

Under the conditions of the Arndt-Eistert homologation reaction, formation of the desired product has been observed through HPLC-MS analysis (see PXN845-d1), The obtained carboxylic acid can be further modified as described above.

Using a substituted succinic anhydride in the multicomponent reaction, compounds of formula (I) can be prepared wherein $R^7$ and/or $R^8$ are other than hydrogen (see also Org. Lett. 2007, 9(20), 4077-4080).

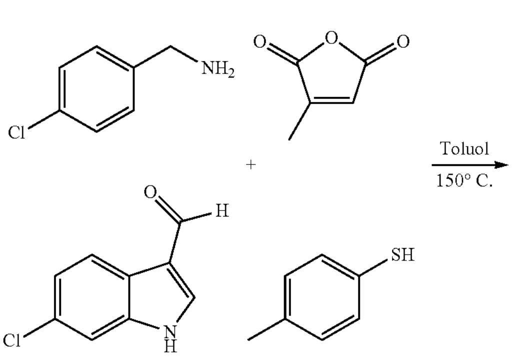

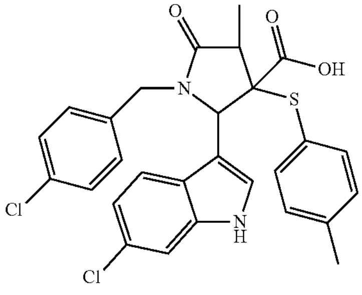

PXN687
Product observed
(as a mixture of diatereoisomers)

5) Elimination

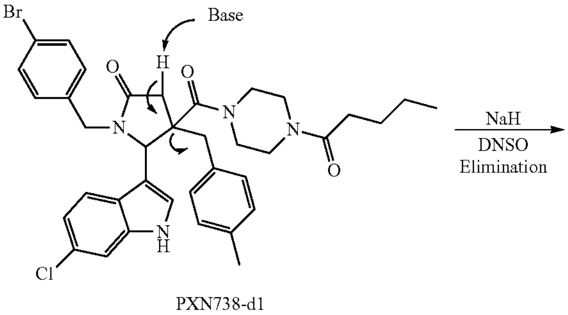

PXN738-d1

-continued

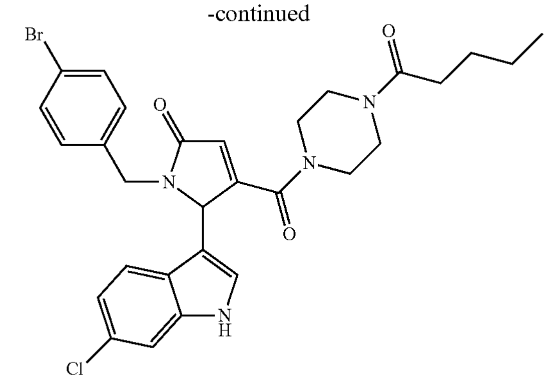

PXN847-d1

PXN736-d1 has been treated with 1.1 eq of natrium hydride at room temperature. Thereby, elimination product PXN847-d1 has been isolated and characterized by HPLC-MS. This Product can be used for further modifications (for example Michael-addition).

6) Synthesis of Compounds Wherein X is N

These compounds may be prepared according to the following scheme:

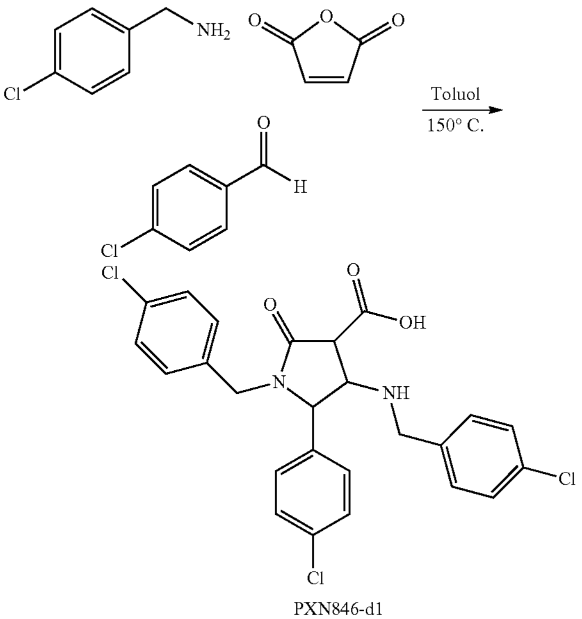

PXN846-d1

In addition, compounds of formulas (I), (Ia), (Ic), (Id), (Ie) and (If) may be prepared following the procedures described e.g. in: Synlett, (11), 1883-1885, 2002; Organic Letters, 9(20), 4077-4080, 2007; Organic Letters, 8(18), 3999-4002, 2006; Tetrahedron, 50(36), 10701-8, 1994; Journal of the Chemical Society, Chemical Communications, (5), 386-7, 1987; Journal of the Chemical Society, Chemical Communications, (5), 386-7, 1987; Tetrahedron Letters, 49(35), 5217-5219, 2008 and Journal of Organic Chemistry, 73(14), 5566-5569, 2008.

Synthesis of the Starting Material 6-chloro-1H-indole-3-carbaldehyde

This Vilsmeyer reaction was performed according to H. G. O. Becker, Organikum, pp. 364-365, Johann Ambrosius Barth Verlag, Heidelberg-Leipzig (1996). To 5 mL DMF in a three-necked flask equipped with a thermometer, 1.8 mL $POCl_3$ was added dropwise in a temperature range between 15° C. and 20° C. Then, a solution of 1 g (6.6 mMol) of 6-chloro-1H-indole in 2 mL DMF was added dropwise in a temperature range between 20° C. and 30° C. The reaction mixture was stirred for 45 minutes at 37° C. Afterwards, the reaction mixture was poured in a mixture of 15 g ice in 10 mL water under stirring. 3.4 g NaOH in 18 mL were added between in a temperature range between 20 and 30° C. The resulting mixture was then refluxed for 5 minutes. After cooling to room temperature, the precipitate was filtered off and washed with 10 mL cold water. Crystallization from ethanol yielded 6-chloro-1H-indole-3-carbaldehyde as a white solid (1.04 g, 88%).

Proliferation Assay:

5000 PA-1 or PA-1/E6 cells were plated in each well of 96-well flat bottom plates, and incubated overnight at 37° C. in 5% $CO_2$. The growth of plated cells was measured by adding 7.5 microMol of WST-1 reagent (Roche Applied Sciences, Germany) to 3 control wells and measuring the $OD_{650}$ and $OD_{450}$ absorbances with a SpectraMax250 plate reader. If the $M_{650}$-$OD_{450}$ values were above 0.5, the remainder of the plate was used for incubation with the compounds of formula (I), (Ia), (Ic), (Id), (Ie) or (If), other pharmacological agents or solvent controls for 48 hours. After this incubation, the WST-1 reagent was added to the wells of the plate and $OD_{650}$-$OD_{450}$ values were calculated as before. Triplicate wells were assayed for each conditions and standard deviation was determined: all experiments were performed at least three times independently.

Apoptosis Annexin V and Tunel Assay:

Annexin V and BrdU-incorporation levels were determined with Guava Nexin and Guava Tunel kits using a Guava Personal Cell Analysis System (PCAS, Guava Technologies, Hayward, Calif.) according to the manufacturer's instruction. $1\times10^6$ PA-1 and PA-1/E6 cells were cultured in BME media supplemented with 10% FBS and various concentrations of the compounds of formula (I) or DMSO for 24 h. Nutlin-3, racemic (Calbiochem, Roche) at 10 μM was applied as positive control. For the Guava Nexin assay, cells were trypsinized and collected by centrifuging at 1000 rpm for 5 min at 4° C. After washing with ice-cold 1× Nexin buffer, cells were resuspended in the same buffer, labeled with Annexin V-PE and 7-aminoactinomycin D in the dark on ice for 20 min, and then analyzed with the PCAS. According to the manufacturer protocol for Guava Tunel assay cells were resuspended in 1% paraformaldehyde, incubated on ice for 60 min, washed in ice-cold PBS buffer. Than cells were fixed in ice-cold 70% ethanol for at least 16 h at −20° C. After incubation, cells were labeled with BrdU DNA labeling mix for 60 min at 37° C., collected by centrifugation at 1000 rpm for 5 min. Cells were resuspended in anti-BrdU staining mix and incubated at room temperature for 45 min in the dark, and then analyzed with the PCAS.

Apoptosis Assays

Temperature-sensitive H1299 clones were seeded onto 6-well plates at a density of 50,000 cells/well. Saos2 cells were plated at $1\times10^6$ cells/100-mm plate. Cells were shifted to 32° C. and harvested at the times indicated after temperature shift. Control cells were maintained at 39° C. TUNEL and multi-caspase assays were conducted using the Guava Personal Cytometer (Guava Technologies) using the Guava TUNEL and multi-caspase detection kits, using protocols provided by the manufacturer (Guava Technologies) with the compounds of formula (I), (Ia), (Ic), (Id), (Ie) or (If),

What is claimed is:

1. A compound of formula (I):

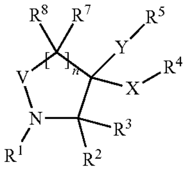

(I)

wherein

V is C═O;

X is oxygen or a group of formula $CH_2$, $CR^{4b}R^{4c}$, NH, $NR^{4b}$, SO, $SO_2$ or a bond;

Y is a group of formula $CONR^6$, $CH_2NR^6$, $CH_2O$, $SO_2NR^6$, $NR^6CO$, $NR^6SO_2$, $NR^{5a}CONR^6$, $NR^6COO$, $OCONR^6$, $CONR^{5a}NR^6$, $CONR^{5a}OR^6$, $CH_2CO$ $CH_2CONR^6$, $CH_2COO$, or $COCR^{5a}R^6$;

n is 1;

$R^1$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^2$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^3$ is an optionally substituted heteroaryl residue having two rings and a total of 9 ring atoms including 1, 2, 3, or 4 heteroatoms selected from O, S, and N;

$R^4$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4b}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4c}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^5$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{5a}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^6$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^7$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^8$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

or the radicals $R^5$ and $R^6$ together are part of an optionally substituted heterocycloalkyl, heteroalkylcycloalkyl, heteroaryl, or heteroarylalkyl ring system, and/or $R^2$ and $R^3$ together are part of an optionally substituted cycloalkyl, alkylcycloalkyl, heterocycloalkyl, heteroalkylcycloalkyl, aralkyl, or heteroaralkyl ring system;

or a pharmaceutically acceptable salt, ester or a pharmaceutically acceptable formulation thereof.

2. The compound of claim 1, wherein $R^1$ is an aryl, heteroaryl, aralkyl or heteroaralkyl radical.

3. The compound of claim 1, wherein $R^1$ is a group of formula -A-Ar or A-Cy wherein A is a bond, $C_1$-$C_4$ alkyl or $C_1$-$C_6$ heteroalkyl or wherein A is a group of formula —$CHR^{1a}$— wherein $R^{1a}$ is a $C_1$-$C_6$ heteroalkyl group, Cy is an optionally substituted $C_3$-$C_7$ cycloalkyl group or an optionally substituted heterocycloalkyl group containing from 3 to 7 ring atoms and Ar is an optionally substituted phenyl ring or an optionally substituted heteroaryl ring containing 5 or 6 ring atoms.

4. The compound of claim 3, wherein Ar is an optionally substituted phenyl or an optionally substituted pyridyl residue.

5. The compound of claim 1, wherein $R^2$ is hydrogen.

6. The compound of claim 1, wherein $R^4$ is $C_1$-$C_6$ alkyl, $C_2$-$C_6$ alkenyl, optionally substituted $C_1$-$C_4$ alkyl-$C_3$-$C_7$ cycloalkyl, an optionally substituted phenyl ring, an optionally substituted benzyl group or an optionally substituted heteroaryl ring having 5 or 6 ring atoms and including from 1 to 3 heteroatoms selected from O, S and N.

7. The compound of claim 1, wherein $R^5$ is an alkyl, heteroalkyl, heterocycloalkyl, heteroalkylcycloalkyl or heteroaralkyl group, all of which groups may be substituted.

8. The compound of claim 1, wherein $R^5$ is selected from the following groups:

$C_1$-$C_6$ alkyl;

heteroalkyl containing 1-6 carbon atoms and 1, 2 or 3 heteroatoms selected from O, S and N;

heteroalkylcycloalkyl comprising a $C_1$-$C_4$ alkyl group or a $C_1$-$C_4$ heteroalkyl group and an optionally substituted heterocycloalkyl group containing 5 or 6 ring atoms and 1, 2 or 3 heteroatoms selected from O, S and N;

heteroaralkyl comprising a $C_1$-$C_4$ alkyl group or a $C_1$-$C_4$ heteroalkyl group and an optionally substituted heteroaryl group containing 5 or 6 ring atoms and 1, 2 or 3 heteroatoms selected from O, S and N;

optionally substituted heteroaryl containing 5 or 6 ring atoms and 1, 2 or 3 heteroatoms selected from O, S and N; and optionally substituted heterocycloalkyl containing 5 or 6 ring atoms and 1, 2 or 3 heteroatoms selected from O, S and N.

9. The compound of claim 1, wherein $R^6$ is hydrogen or $C_1$-$C_4$ alkyl.

10. The compound of claim 1, wherein $R^5$ and $R^6$ together are part of an optionally substituted heterocycloalkyl ring containing 4, 5, 6 or 7 ring atoms and 1, 2 or 3 heteroatoms selected from O, S and N.

11. The compound of claim 1, wherein $R^5$ and $R^6$ together are part of an optionally substituted piperazine or piperidine ring.

12. A compound of formula (I):

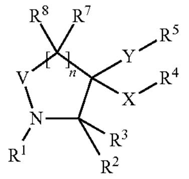

(I)

wherein

V is C═O;

X is oxygen or a group of formula $CH_2$, $CR^{4b}R^{4c}$, NH, $NR^{4b}$, SO, $SO_2$ or a bond;

Y is a group of formula $CONR^6$, $CH_2NR^6$, $CH_2O$, $SO_2NR^6$, $NR^6CO$, $NR^6SO_2$, $NR^{5a}CONR^6$, $NR^6COO$, $OCONR^6$, $CONR^{5a}NR^6$, $CONR^{5a}OR^6$, $CH_2CO$ $CH_2CONR^6$, $CH_2COO$, or $COCR^{5a}R^6$;

n is 1;

$R^1$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^2$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^3$ has the following structure

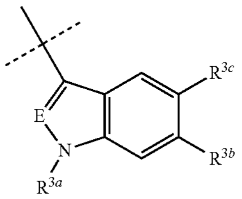

wherein E is N or CH, $R^{3a}$ is H, $C_1$-$C_6$ alkyl or $C_1$-$C_6$ heteroalkyl, $R^{3b}$ is H, F, Cl, Br, $CH_3$, $OCH_3$ or $CF_3$ and $R^{3c}$ is H, F, Cl, Br, $CH_3$, $OCH_3$ or $CF_3$;

$R^4$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4b}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{4c}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^5$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^{5a}$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^6$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^7$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^8$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

or the radicals $R^5$, and $R^6$ together are part of an optionally substituted heterocycloalkyl, heteroalkylcycloalkyl, heteroaryl, or heteroarylalkyl ring system, and/or $R^2$ and $R^3$ together are part of an optionally substituted cycloalkyl, alkylcycloalkyl, heterocycloalkyl, heteroalkylcycloalkyl, aralkyl, or heteroaralkyl ring system;

or a pharmaceutically acceptable salt, ester or a pharmaceutically acceptable formulation thereof.

13. A pharmaceutical composition comprising the compound of claim 1, or a pharmaceutically acceptable ester, prodrug, or salt thereof, optionally in combination with a pharmaceutically acceptable carrier.

* * * * *